United States Patent
Tang et al.

(10) Patent No.: US 6,824,973 B2
(45) Date of Patent: Nov. 30, 2004

(54) METHOD OF PROMOTING STEM CELL PROLIFERATION OR SURVIVAL BY CONTACTING A CELL WITH A STEM CELL FACTOR-LIKE POLYPEPTIDE

(75) Inventors: Y. Tom Tang, San Jose, CA (US); Ivan Labat, Mountain View, CA (US); Radoje T. Drmanac, Palo Alto, CA (US); Nancy Mize, Mountain View, CA (US); Mitsuo Nishikawa, Gunma (JP); Cheng-Chi Chao, Cupertino, CA (US)

(73) Assignees: Kirin Beer Kabushiki Kaisha, Tokyo (JP); Nuvelo Inc., Synnyvale, CA (US)

( * ) Notice: Subject to any disclaimer, the term of this patent is extended or adjusted under 35 U.S.C. 154(b) by 0 days.

(21) Appl. No.: 09/894,912

(22) Filed: Jun. 28, 2001

(65) Prior Publication Data

US 2003/0044792 A1 Mar. 6, 2003

Related U.S. Application Data

(63) Continuation-in-part of application No. 09/757,562, filed on Jan. 9, 2001, now abandoned, which is a continuation of application No. 09/543,774, filed on Apr. 5, 2000, now abandoned, which is a continuation-in-part of application No. 09/496,914, filed on Feb. 3, 2000, now abandoned.

(60) Provisional application No. 60/282,397, filed on Apr. 5, 2001, now abandoned, provisional application No. 60/266,614, filed on Feb. 5, 2001, and provisional application No. 60/215,733, filed on Jun. 28, 2000, now abandoned.

(51) Int. Cl.[7] .............................. C12Q 1/00; C12N 5/00; C07K 14/475; C07K 14/52
(52) U.S. Cl. ........................... 435/4; 435/325; 435/375; 530/350; 530/351; 530/399
(58) Field of Search ................................. 530/300, 350, 530/351, 399; 514/2, 12; 424/85.1, 198.1; 536/23.1, 23.5; 435/4, 7.1, 375, 377, 325

(56) References Cited

FOREIGN PATENT DOCUMENTS

| WO | WO 98/49302 | 11/1998 |
| WO | WO 00/56755 | 9/2000 |

OTHER PUBLICATIONS

Brenner, S.E. Errors in genome function. Trends in Genetics 15(4): 132–133, 1999.*
Bork et al. Go hunting in sequence databases but watch out for the traps. Trends in Genetics. 12(10): 425–427, 1996.*
Wells. J.A. Additivity of mutational effects in proteins. Biochemistry 29 (37): 8509–8517, 1990.*
Ngo et al. Computational complexity, protein structure prediction, and the Levinthal paradox. The Protein Folding Problem and Tertiary Structure Prediction, pp. 492–495, 1994.*
Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*

* cited by examiner

Primary Examiner—Brenda Brumback
Assistant Examiner—Bridget E. Bunner
(74) Attorney, Agent, or Firm—Marshall, Gerstein & Borun LLP

(57) ABSTRACT

The invention provides novel polynucleotides and polypeptides encoded by such polynucleotides and mutants or variants thereof that correspond to a novel human stem cell growth factor-like protein. These polynucleotides comprise nucleic acid sequences isolated from cDNA libraries from human testis cells (Hyseq clone identification numbers 2880984 and 2881695), from human fetal skin (Hyseq clone identification number 15375176), adult spleen (Hyseq clone identification number 14856094), and human endothelial cells (Hyseq clone identification numbers 13804756, 13687487, 13804756). Other aspects of the invention include vectors containing processes for producing novel human stem cell growth factor-like polypeptides, and antibodies specific for such polypeptides.

7 Claims, 6 Drawing Sheets

BLASTP ALIGNMENT OF SEQ ID NO: 10, STEM CELL GROWTH FACTOR-LIKE POLYPEPTIDE WITH MOUSE THROMBOSPONDIN TYPE 1 DOMAIN POLYPEPTIDE SEQ ID NO: 25

```
Query: Stem cell growth factor-like plypeptide (SEQ ID NO: 10)
Sbjct: dbj|BAA75640.1| (AB016768) thrombospordin type 1 domain (Mus musculus) (SEQ ID NO: 25)
Length = 265

Score = 634 (228.2 bits), Expect = 7.8e-62, P = 7.8e-62
Identities = 112/237 (47%), Positives = 152/237 (64%)

Query:   19 IGSQNASRGRHRQRRMHPNVSQGCQGGCATCSDYNGCLSCKPKLFFALEKIGMKQIGVCLS  78
             +GS+  +G+RQRR+        SQ C  GC   CS+ NGCL C P+LF  L+R ++Q+GVCL
Sbjct:   19 VGSRGI-KGKRQERISAEGSQACAKGCELCSEVNGCLKCSPKLFILERND=RQVGVCLP   77

Query:   79 SCPSGYYGTRYPDINKCTKCKAD-CDTCFNKYFCTKCKSGFYLHGKCLDNCPEGLEARN  137
             SCP GY+  R  PD+NKC KCK  + C+ C?+ NFC+KC+   Y+H G+C   CPEG  A N
Sbjct:   78 SCPGYFDARYPDMNKCZKCKIBECEACFSHNFCTKCQEALYLHKGRCYPACPEGSTAAN  137

Query:  138 HTMECVSIVHCEVSEWNPWSPCTKKGKTC9FKRGTETRVREIIQHPSAKGNLCPPTKETR  197
             TMEC S   CE+SEW+PW PC+KK K CGF++G+E R +++  P    C T ETR
Sbjct:  138 STMECGSPAQCEMSEWSPKGPCSKKRKLCGPRKGSEERTRGVLHAPGDPTTCSDTKETR  197

Query:  298 KCTVQRKKCCKGERGKKGRERKRKKPNKGESKEAIPDSKSLESSKEIPEQRENKQQQ  254
             KCCTV+R  C  +G++ +KG + +R+  N+ +++  +SK   S+   +R  QQQ
Sbjct:  198 KCCTVRRTPCPEGQKRRKGGQQSRRZNANTRHPARK---NSKEPRSNS----RRHKGQQQ  247
```

FIG. 2

BLASTP ALIGNMENT OF SEQ ID NO: 10, STEM CELL GROWTH FACTOR-LIKE POLYPEPTIDE WITH HUMAN SECRETED PROTEIN CLONE DA228_6 POLYPEPTIDE SEQ ID NO: 26

```
Query: Stem cell growth factor-like polypeptide (SEQ ID NO: 10)
Sbjct: sp|W85607|W85607 Secreted protein clone da228_6 (SEQ ID NO: 26)
Length = 292

Score = 1477 (525.0 bits), Expect = 2.1e-151, P = 2.1e-151
Identities = 265/265 (100%), Positives = 265/265 (100%)

Query:   1  MHLRLISWLFIILNFMEYIGSQNASRGRRQRRJGPNVSQGCQGGCATCSDYNGCLSCKPR   60
            MHLRLISWLFIILNFMEYIGSQNASRGRRQRRMHPNVSQGCQGGCATCSDYNGCLSCKPR
Sbjct:   1  MHLRLISWLFIILNFMEYIGSQNASRGRRQRRMHPNVSQGCQGGCATCSDYNGCLSCKPR   60

Query:  61  LFFALERIGMKQIGVCLSSCPSGYYGTRYPDINKCTKCKADCDTCFNKNFCTKCCKSGFYL  120
            LFFALERIGMKQIGVCLSSCPSGYYGTRYPDINKCTKCKADCDTCFNKNFCTKCCKSGFYL
Sbjct:  61  LFFALERIGMKQIGVCLSSCPSGYYGTRYPDINKCTKCKADCDTCFNKNFCTKCCKSGFYL  120

Query: 121  HLGKCLDNCPEGLEANNHTMECVSIVHCEVSEWNPWSPCTKKGKTCGFKRGTETRVREII  180
            HLGKCLDNCPEGLEANNHTMECVSIVHCEVSEWNPWSPCTKKGKTCGFKRGTETRVREII
Sbjct: 121  HLGKCLDNCPEGLEANNHTMECVSIVHCEVSEWNPWSPCTKKGKTCGFKRGTETRVREII  180

Query: 181  QHPSAKGNLCPPTNETRKCTVQRKKCQKGERGKKGRERKRKKPNKGESKEAIPDSKSLES  240
            QHPSAKGNLCPPTNETRKCTVQRKKCQKGERGKKGRERKRKKPNKGESKEAIPDSKSLES
Sbjct: 181  QHPSAKGNLCPPTNETRKCTVQRKKCQKGERGKKGRERKRKKPNKGESKEAIPDSKSLES  240

Query: 241  SKEIPEQRENKQQQKKRKVQDKQKS  265
            SKEIPEQRENKQQQKKRKVQDKQKS
Sbjct: 241  SKEIPEQRENKQQQKKRKVQDKQKS  265
```

FIG. 3

METHOD OF PROMOTING STEM CELL PROLIFERATION OR SURVIVAL BY CONTACTING A CELL WITH A STEM CELL FACTOR-LIKE POLYPEPTIDE

1. CROSS REFERENCE TO RELATED APPLICATIONS

This application claims priority of U.S. Provisional Application Ser. No. 60/282,397 filed Apr. 5, 2001, and U.S. Provisional Application Ser. No. 60/215,733, filed Jun. 28, 2000, and U.S. Provisional Application Ser. No. 60/266,614 filed Feb. 5, 2001, now abandoned, is a continuation-in-part application of U.S. application Ser. No. 09/757,562 filed Jan. 9, 2001, now abandoned, entitled "Methods and Materials Relating to Novel Stem Cell Growth Factor-Like Polypeptides and Polynucleotides", which in turn is a continuation application of U.S. application Ser. No. 09/543,774 filed Apr. 5, 2000, now abandoned, entitled "Methods and Materials Relating to Novel Stem Cell Growth Factor-Like Polypeptides and Polynucleotides", which in turn is a continuation-in-part application of U.S. application Ser. No. 09/496,914 filed Feb. 03, 2000, now abandoned, entitled "Novel Contigs Obtained from Various Libraries", all of which are incorporated herein by reference in their entirety.

2. TECHNICAL FIELD

The present invention provides novel polynucleotides and proteins encoded by such polynucleotides, along with uses for these polynucleotides and proteins, for example in therapeutic, diagnostic and research methods. In particular, the invention relates to a novel human stem cell growth factor-like protein.

2.1 Background Art

Technology aimed at the discovery of protein factors (including e.g., cytokines, such as lymphokines, interferons, circulating soluble factors, chemokines, and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization-based cloning techniques, have advanced the state of the art by making available large numbers of DNA/amino acid sequences for proteins that are known to have biological activity, for example, by virtue of their secreted nature in the case of leader sequence cloning, by virtue of their cell or tissue source in the case of PCR-based techniques, or by virtue of structural similarity to other genes of known biological activity.

Identified polynucleotide and polypeptide sequences have numerous applications in, for example, diagnostics, forensics, gene mapping; identification of mutations responsible for genetic disorders or other traits, to assess biodiversity, and to produce many other types of data and products dependent on DNA and amino acid sequences.

3. SUMMARY OF THE INVENTION

The present invention provides an isolated polynucleotide encoding a polypeptide having stem cell growth factor activity, said polynucleotide comprising the nucleotide sequence of SEQ ID NO: 9, 11, 12, 31 or 33 or the mature protein coding portion thereof, or a fragment, analog, variant or derivative thereof that encodes a polypeptide retaining stem cell growth factor activity. These polypeptides include those which hybridize to the complement of the nucleotide sequence of SEQ ID NO: 9, 11, 12, 31 or 33 under stringent hybridization conditions, those which comprise a nucleotide sequence having greater than about 85% sequence identity with the nucleotide sequence of SEQ ID NO:9, 11, 12, 31 or 33, those which comprise a nucleotide sequence having greater than about 90% sequence identity with the nucleotide sequence of SEQ ID NO:9, 11, 12, 31 or 33 and those polypeptides which comprise a nucleotide sequence having greater than about 92% sequence identity with the nucleotide sequence of SEQ ID NO:9, 11, 12, 31 or 33. 14. The polynucleotides may be a DNA. The present invention also encompasses polynucleotides which comprise the complement of these polynucleotides.

The present invention provides for isolated polynucleotide encoding a polypeptide having stem cell growth factor activity, said polynucleotide comprising the nucleotide sequence of SEQ ID NO: 9, 11, 12, 31 or 33 or the mature protein coding portion thereof, or a fragment, analog, variant or derivative thereof that encodes a polypeptide retaining stem cell growth factor activity with the proviso that said polynucleotide sequence does not consist of the nucleotide sequence of SEQ ID NO: 47. These polypeptides include those which hybridize to the complement of the nucleotide sequence of SEQ ID NO: 9, 11, 12, 31 or 33 under stringent hybridization conditions and with the proviso that said polynucleotide sequence does not consist of the nucleotide sequence of SEQ ID NO: 47, those which comprise a nucleotide sequence having greater than about 85% sequence identity with the nucleotide sequence of SEQ ID NO:9, 11, 12, 31 or 33 and with the proviso that said polynucleotide sequence does consist of the nucleotide sequence of SEQ ID NO: 47, those which comprise a nucleotide sequence having greater than about 90% sequence identity with the nucleotide sequence of SEQ ID NO:9, 11, 12, 31 or 33 and with the proviso that said polynucleotide sequence does not consist of the nucleotide sequence of SEQ ID NO: 47, and those polypeptides which comprise a nucleotide sequence having greater than about 92% sequence identity with the nucleotide sequence of SEQ ID NO:9, 11, 12, 31 or 33 and with the proviso that said polynucleotide sequence does not consist of the nucleotide sequence of SEQ ID NO: 47.

The present invention provides for an isolated polynucleotide that comprises the mature protein coding sequence of SEQ ID NO: 9, 11, 12,31 or 33. The invention also provides for an isolated polynucleotide that comprises the nucleotide sequence of SEQ ID NO: 9, 11, 12, 31 or 33.

The invention provides for a DNA encoding a polypeptide having stem cell growth factor activity, said polynucleotide comprising the nucleotide sequence of SEQ ID NO: 9, 11, 12, 31 or 33 or the mature protein coding portion thereof, or a fragment, analog, variant or derivative thereof that encodes a polypeptide retaining stem cell growth factor activity wherein the encoded polypeptide has an amino acid sequence comprising at least amino acid residues 22 to 279 of SEQ ID NO: 32, or an amino acid sequence comprising at least amino acid residues 22 to 272 of SEQ ID NO: 34; or the encoded polypeptide has an amino acid sequence including deletion, substitution or insertion of one or several amino acids in the amino acid sequence comprising at least amino acid residues 22 to 279 of SEQ ID NO: 32, or an amino acid sequence comprising at least amino acid residues 22 to 272 of SEQ ID NO: 34, and which has an activity to support proliferation or survival of hermatopoietic stem cell or hematopoietic progenitor cell, with a proviso that C-terminal amino acid sequence does not comprise the amino acid sequence of SEQ ID NO: 46.

The invention provides for a DNA encoding comprising the nucleotide stem cell growth factor activity, said polynucleotide comprising the nucleotide sequence of SEQ ID NO: 9, 11, 12, 31 or 33 or the mature protein coding portion thereof, or a fragment, analog, variant or derivative thereof that encodes a polypeptide retaining stem cell growth factor activity, which is a DNA which comprises at least nucleotides 574 to 1347 of SEQ ID NO: 31; or a DNA which is hybridizable with the nucleotide sequence of SEQ ID NO: 31 or a probe prepared from said sequence, under stringent conditions, and which has an activity to support proliferation or survival of hematopoietic stem cell or hematopoietic progenitor cell. These include DNAs which hybridize under the following stringent conditions: 6×SSC,5×Denhardt, 0.5% SDS and 68° C. (SSC 3M NaCl, 0.3M sodium citrate, 50×Denhardt/1% BSA/1% polyvinyl pyrrolidone, 1% Ficoll 400/, or 6×SSC, 5×Denhardt, 0.5% SDS, 50% formamide and 42° C.

The invention provides for a DNA encoding a polynucleotide encoding a polypeptide having stem cell growth factor activity, said polynucleotide comprising the nucleotide sequence of SEQ ID NO: 9, 11, 12, 31 or 33 or the mature protein coding portion thereof, or a fragment, analog, variant or derivative thereof that encodes a polypeptide retaining stem cell growth factor activity, which is a DNA which comprises at least nucleotides 321 to 1074 of SEQ ID NO: 33; or DNA which is hybridizable with the nucleotide sequence of SEQ ID NO: 33 or a prove prepared from said sequence, under stringent conditions, and which has an activity to support proliferation or survival of hematopoietic stem cell or hematopoietic progenitor cell. These include DNAs which hybridize under the following stringent conditions: 6×SSC/5×Denhardt, 0.5% SDS and 68° C. (SSC 3M NaCl, 0.3M sodium citrate, 50×Denhardt/1% BSA/1% polyvinyl pyrrolidone, 1% Ficoll 400, or 6×SSC, 5×Deanhardt, 0.5% SDS, 50% Formamide and 42° C.

The invention also provides for vectors, including expression vectors, comprising the polynucleotide of the present invention. The invention futher provides for host cells genetically engineered to express a polynucleotide of the present invention. The invention provides for host cells genetically engineered to contain a polynucleotide of the present invention in operative association with a regulatory sequence that controls expression of the polynucleotide in the host cell. These host cells include those which have been genetically engineered to contain a heterologous regulatory sequence that increases expression of an endogenous polynucleotide.

The invention provides for a method of producing a polypeptide having stem cell growth factor activity comprising growing these host cells in a culture medium under conditions that permit expression of said polypeptide and isolating said polypeptide from said host cell or said culture medium The invention also encompasses a polypeptide produced by this method.

The invention provides for an isolated polypeptide comprising the amino acid sequence of SEQ ID NO: 10, 13, 16, 32 or 34, or the mature protein portion thereof, or a fragment, analog, variant or derivative thereof that retains stem cell growth factor activity. These polypeptides include polypeptides which are encoded by an isolated polynucleotide encoding a polypeptide having stem cell growth factor activity, said polynucleotide comprising the nucleotide sequence of SEQ ID NO: 9, 11, 12, 31 or 33 or the mature protein coding portion thereof, or a fragment, analog, variant or derivative thereof that encodes a polypeptide retaining stem cell growth factor activity and which hybridizes to the complement of the nucleotide sequence of SEQ ID NO: 9, 11, 12, 31 or 33 under stringent hybridization conditions.

The invention provides for an isolated polypeptide comprising the amino acid sequence of SEQ ID NO: 10, 13, 16, 32 or 34, or the mature protein portion thereof, or a fragment, analog, variant or derivative thereof that retains stem cell growth factor activity which comprises an amino acid sequence having greater than about 85% sequence identity with the nucleotide sequence of SEQ ID NO: 10, 13, 16, 32 or 34, an amino acid sequence having greater than about 92% sequence identity with the nucleotide sequence of SEQ ID NO: 10, 13, 16, 32 or 34, with the proviso that said polypeptide sequence does not consist of the amino acid sequence of SEQ ID NO: 48.

The invention also provides for an isolated polypeptide comprising the mature protein portion of SEQ ID NO: 10, 13, 16, 32 or 34.

The invention provides for an isolated polypeptide comprising the amino acid sequence of SEQ ID NO: 10, 13, 16, 32 or 34, or the mature protein portion thereof, or a fragment, analog, variant or derivative thereof that retains stem cell growth factor activity, wherein the polypeptide comprises one or more motifs selected from the group of a laminin-type EGF-like domain, a membrane attack complex component/perforin domain, and neurohypophysial hormone signature.

The invention provides for polypeptides which are an expression product of a DNA of the present invention, where these polypeptide which have an activity to support proliferation or survival of hematopoietic stem cell or hematopoietic progenitor cell, with the proviso that the C-terminal amino acid sequence does not comprise the amino acid sequence of SEQ ID NO: 46.

The invention provides for an isolated polynucleotide that comprises the nucleotide sequence of SEQ ID NO: 9, 11, 12, 31 or 33, which has an amino acid sequence comprising at least amino acid residues 22 to 279 of SEQ ID NO: 32, or an amino acid sequence including deletion, substitution or insertion of one or several amino acids in the amino acid sequence comprising at least amino acid residues 22 to 279 of SEQ ID NO: 32

The invention provides an isolated polypeptide comprising the amino acid sequence of SEQ ID NO: 10, 13, 16, 32 or 34, or the mature protein portion thereof, or a fragment, analog, variant or derivative thereof that retains stem cell growth factor activity polypeptide, which has an amino acid sequence comprising at least amino acid residues 22 to 272 of SEQ ID NO: 34, or an amino acid sequence including deletion, substitution or insertion of one or several amino acids in the amino acid sequence comprising at least amino acid residues 22 to 272 of SEQ ID NO: 34.

The invention also provides for an isolated polypeptide comprising the amino acid sequence of SEQ ID NO: 10, 13, 16, 32 or 34, or the mature protein portion thereof, or a fragment, analog, variant or derivative thereof that retains stem cell growth factor activity, which is modified with one or more modifying agent selected from the group consisting of polyethylene glycol (PEG), dextran, poly(N-vinyl-pyrrolidone), polypropylene glycol homopolymer, copolymer of polypropylene oxide/ethylene oxide, polyoxyethylated polyol and polyvinyl alcohol.

The invention provides for an isolated polypeptide comprising the amino acid sequence of SEQ ID NO: 10, 13, 16, 32 or 34, or the mature protein portion thereof, or a fragment, analog, variant or derivative thereof that retains stem cell growth factor activity which comprises at least ten consecutive amino acids from SEQ ID NO: 10 or 13.

The invention also provides for an isolated polypeptide comprising the amino acid sequence of SEQ ID NO: 10, 13, 16, 32 or 34, or the mature protein portion thereof, or a fragment, analog, variant or derivative thereof that retains stem cell growth factor activity, which comprises at least ten consecutive amino acids from the C-terminal seventeen amino acids of SEQ ID NO: 10 or 13.

The invention provides for a polypeptide with biological activity, said polypeptide comprising at least 272 amino acids and having at least 98% identity with SEQ ID NO: 10. The invention also provides for an isolated polypeptide with stem cell growth factor activity having at least 90% identity with SEQ ID NO: 10, 13, or 16 and lacking amino acid sequence GIEVTLAEGLTSVSQRTQPTPCRRRYL (SEQ ID NO: 29) wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine.

The invention also provides for an isolated polypeptide with stem cell growth factor activity having at least 90% identity with SEQ ID NO: 10, 13, or 16 and lacking any 10 consecutive amino acids from a amino acid sequence GIEVTLAEGLTSVSQRTQPTPCRRRYL (SEQ ID NO: 29), wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine.

The invention provides for an isolated polypeptide with stem cell growth factor activity having at least an amino acid sequence SVSVSTVH (SEQ ID NO: 27) or VSVSTVH (SEQ ID NO: 28), wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine.

The invention encompasses a polynucleotide which encodes any of the polypeptides of the present invention.

The invention provides for a kit comprising an isolated polypeptide comprising the amino acid sequence of SEQ ID NO: 10, 13, 16, 32 or 34, or the mature protein portion thereof, or a fragment, analog, variant or derivative thereof that retains stem cell growth factor activity.

The invention further provides for a culture medium comprising an amount of an isolated polypeptide comprising the amino acid sequence of SEQ ID NO: 10, 13, 16, 32 or 34, or the mature protein portion thereof, or a fragment, analog, variant or derivative thereof that retains stem cell growth factor activity polypeptide, wherein the amount is effective to maintain survival of or promote proliferation of a stem cell or germ cell.

The composition comprising an isolated polypeptide comprising the amino acid sequence of SEQ ID NO: 10, 13, 16, 32 or 34, or the mature protein portion thereof, or a fragment, analog, variant or derivative thereof that retains stem cell growth factor activity and a pharmaceutically acceptable carrier or diluent. These compositions can be pharmaceutical compositions including those having an effect to support proliferation or survival of hematopoietic stem cell or hematopoietic progenitor cell, which comprises a polypeptide which has an amino acid sequence comprising at least amino acid residues 22 to 279 of SEQ ID NO: 32, or an amino acid sequence comprising at least amino acid residues 22 to 272 of SEQ ID NO: 34; or a polypeptide which has an amino acid sequence including deletion, substitution or insertion of one or several amino acids in the amino acid sequence comprising at least amino acid residues 22 to 279 of SEQ ID NO: 32, or an amino acid sequence comprising at least amino acid residues 22 to 272 of SEQ ID NO: 34, and which has an activity to support proliferation or survival of hematopoietic stem cell or hematopoietic progenitor cell.

The invention provides for an antibody that binds to an isolated polypeptide comprising the amino acid sequence of SEQ ID NO: 10, 13, 16, 32 or 34, or the mature protein portion thereof, or a fragment, analog, variant or derivative thereof that retains stem cell growth factor activity. The antibodies of the present invention may specifically binds to a polypeptide having the amino acid sequence of SEQ ID NO: 10, 13, 16, 32 or 34 including those which do not bind to a polypeptide having the amino acid sequence of SEQ ID NO: 48. The antibodies of the present invention include polyclonal antibodies, monoclonal antibodies, antibody fragments, chimeric antibodies, and humanized antibodies. Further, the invention encompasses kits comprising the antibodies of the present invention.

The invention provides for a method for detecting a polynucleotide of the present invention in a sample, comprising: a) contacting the sample with a compound that binds to and forms a complex with the polynucleotide for a period sufficient to form the complex; and b) detecting the complex, so that if a complex is detected, the polynucleotide is detected. The invention also provides for methods for detecting a polynucleotide of the present invention in a sample, comprising: a) contacting the sample under stringent hybridization conditions with nucleic acid primers that anneal to the polynucleotide under such conditions; b) amplifying a product comprising at least a portion of the polynucleotide; and c) detecting said product and thereby the polynucleotide in the sample. These methods include a method wherein the polynucleotide detected encodes a polypeptide comprising the amino acid sequence of SEQ ID NO: 10, 13, 16, 32 or 34, or the mature protein portion thereof, or a fragment, analog, variant or derivative thereof that retains stem cell growth factor activitya polypeptide of claim 23, and the method further comprises reverse transcribing an annealed RNA molecule into a cDNA polynucleotide.

The invention also provides for a method for detecting a polypeptide of the present invnetion in a sample, comprising: a) contacting the sample with a compound that binds to and forms a complex with the polypeptide under conditions and for a period sufficient to form the complex; and b) detecting formation of the complex, so that if a complex formation is detected, the polypeptide is detected.

The invention also provides for a method for identifying a compound that binds to a polypeptide of the invention, comprising: a) contacting the compound with the polypeptide under conditions and for a time sufficient to form a polypeptide/compound complex; and b) detecting the complex, so that if the polypeptide/compound complex is detected, a compound that binds to the polypeptide is identified.

The invention also provides for a method for identifying a compound that binds to the polypeptide of the present invention, comprising: a) contacting the compound with the polypeptide, in a cell, for a time sufficient to form a polypeptide/compound complex, wherein the complex drives expression of a reporter gene sequence in the cell; and b) detecting the complex by detecting reporter gene sequence expression, so that if the polypeptide/compound complex is detected, a compound that binds to the polypeptide is identified.

The invention provides for a nucleic acid array comprising a polynucleotide of the present invention or a unique segment of a polynucleotide of the present invnetion attached to a surface. These arrays include those which full-matches to the polynucleotide or a unique segment of the polynucleotide of the present inventions, those which detect mismatches to the polynucleotide or a unique segment of the polynucleotide of the present invention.

The invention provides for a method of treatment of a subject in need of enhanced activity or expression of stem cell growth factor-like polypeptide of the present invention comprising administering to the subject: (a) a composition comprising a therapeutic amount of an agonist of said polypeptide; (b) a composition comprising a therapeutic amount of the polypeptide; or (c) a composition comprising a therapeutic amount of a polynucleotide encoding the polypeptide in form and under conditions such that the polypeptide is produced; said composition comprising a pharmaceutically acceptable carrier or diluent.

The invention also provdies for a method of treatment of a subject having need of decreased activity or expression of stem cell growth factor-like polypeptide of the present invention comprising administering to the subject: (a) a composition comprising a therapeutic amount of an antagonist of said polypeptide; (b) a composition comprising a therapeutic amount of the polynucleotide that inhibits the expression of the nucleotide sequence encoding said polypeptide; and (c) a composition comprising a therapeutic amount of a polypeptide that competes with the stem cell growth factor-like polypeptide for its ligand; said composition comprising a pharmaceutically acceptable carrier or diluent.

The invention also provides for a method of supporting proliferation or survival of a stem cell or germ cell comprising contacting said cell with an amount of a polypeptide of the present invention effective to maintain survival of or promote proliferation of said cell. These methods include those wherein said cell is a primordial germ cell, germ line stem cell, embryonic stem cell, hematopoietic stem cell, hematopoietic progenitor cell, pluripotent cell, or totipotent cell. These methods also include those wherein the polypeptide comprises an amino acid sequence of SEQ ID NO: 10, 13, or 16, or comprises an amino acid sequence 90% identical to SEQ ID NO. 10, 13, or 16. These methods further include those wherein the stem cell growth factor-like polypeptide is encoded by a polynucleotide that hybridizes to the complement of a polynucleotide encoding SEQ ID NO: 10, 13, or 16 under stringent hybridization conditions.

The invention encompasses a stromal cell genetically engineered to express a polypeptide of the invention in an amount effective to support proliferation or survival of a stem cell or germ cell. These cells include primordial germ cells germ line stem cells embryonic stem cells hematopoietic stem cells hematopoietic progenitor cells pluripotent cells or totipotent cells The invention provides for an implant comprising a cell genetically engineered to express a polypeptide of the present invention in an amount effective to support proliferation or survival of a stem cell or germ cell. These implants of the present invention include those wherein the cell is a primordial germ cell, germ line stem cell, embryonic stem cell, hematopoietic stem cell, hematopoietic progenitor cell, pluripotent cell, or totipotent cell.

The invention provides for an isolated polynucleotide comprising the protein coding cDNA insert of the plasmid deposited with the National Institute of Bioscience and Human-Technology, Agency of Industrial Science and Technology (Zip code 305-8566; Higashi 1-1-3, Tsukuba, Ibaraki, Japan) on Jun. 26, 2000 under accession number FERM BP-7198 and the mature polypeptide expressed by this polynucleotide of in a suitable host cell.

The invention also provides for an isolated polynucleotide comprising the protein coding cDNA insert of the plasmid deposited with the National Institute of Bioscience and Human-Technology, Agency of Industrial Science and Technology (Zip code 305-8566; Higashi 1-1-3, Tsukuba, Ibaraki, Japan) on Jun. 26, 2000 under accession number FERM BP-7197 and the mature polypeptide expression product expressed by this polynucleotide in a suitable host cell.

Optionally preferred are polynucleotides and polypeptides other than the nucleotide sequence set forth as SEQ ID NO: 3284 (and the polypeptide sequence encoded therein) in U.S. application Ser. No. 09/496,914 filed Feb. 3, 2000, now abandoned, and the protein set out in Genbank Accession No. BAB28811.

The compositions of the present invention include novel isolated polypeptides, novel isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies. Specifically, the polynucleotides of the present invention are based on polynucleotides isolated from cDNA libraries prepared from human testis cells (Hyseq clone identification numbers 2880984 and 2881695), from human fetal skin (Hyseq clone identification number 15375176), adult spleen (Hyseq clone identification number 14856094), and human endothelial cells (Hyseq clone identification numbers 13804756, 13687487, 13804756).

In one aspect, the invention involves an isolated polynucleotide with stem cell growth factor activity comprising a nucleotide sequence of SEQ ID NO: 9, 11, 12, 31 or 30, the mature protein coding portion thereof, the extracellular coding portion thereof, or the active domain coding portion thereof.

In one embodiment, the invention involves an isolated polynucleotide encoding a polypeptide with biological activity, and said polynucleotide hybridizes to the complement of the polynucleotide with stem cell growth factor activity under stringent hybridization conditions.

In a further embodiment, the invention involves an isolated polynucleotide encoding a polypeptide with biological activity, said polynucleotide having at least about 92% sequence identity with the polynucleotide with stem cell growth factor activity.

In a further embodiment, the invention involves an isolated polynucleotide encoding a polypeptide with biological activity, said polypeptide having greater than about 95% sequence identity with the polynucleotide with stem cell growth factor activity.

In a still further embodiment, the polynucleotide with stem cell growth factor activity is a DNA.

In another embodiment, the invention involves an isolated polynucleotide which comprises the complement of the polynucleotide with stem cell growth factor activity.

The invention also involves a vector comprising the polynucleotide with stem cell growth factor activity. Alternatively, the invention involves an expression vector comprising the polynucleotide with stem cell growth factor activity. A host cell genetically engineered to express the polynucleotide with stem cell growth factor activity is also provided. The host cell genetically engineered to contain the polynucleotide with stem cell growth factor activity in operative association with a regulatory sequence that controls expression of the polynucleotide in the host cell.

In another aspect, the invention involves an isolated polypeptide comprising an amino acid sequence consisting of SEQ ID NO: 10, 13, 16, 32 or 34, the mature protein portion thereof, the extracellular portion thereof, or active domain thereof.

Also provided is a composition comprising the polypeptide and a carrier. In another embodiment, the invention involves an antibody directed against the polypeptide. In another aspect, the invention involves a method for detecting the polynucleotide with stem cell growth factor activity in a sample, comprising contacting the sample with a compound that binds to and forms a complex with the polynucleotide for a period sufficient to form the complex; and detecting the complex, so that if a complex is detected, the polynucleotide is detected.

The invention also involves a method for detecting the polynucleotide with stem cell growth factor activity in a sample, comprising contacting the sample under stringent hybridization conditions with nucleic acid primers that anneal to the polynucleotide under such conditions; amplifying a product comprising at least a portion of the polynucleotide; and detecting said product and thereby the polynucleotide in the sample.

In a further embodiment, the polynucleotide is an RNA molecule that encodes the polypeptide, and the method further comprises reverse transcribing an annealed RNA molecule into a cDNA polynucleotide.

Also provided is a method for detecting the polypeptide in a sample, comprising contacting the sample with a compound that binds to and forms a complex with the polypeptide under conditions and for a period sufficient to form the complex; and detecting formation of the complex, so that if a complex formation is detected, the polypeptide is detected.

In another embodiment, the invention provides a method for identifying a compound that binds to the polypeptide, comprising contacting the compound with the polypeptide of under conditions and for a time sufficient to form a polypeptide/compound complex; and detecting the complex, so that if the polypeptide/compound complex is detected, a compound that binds to the polypeptide is identified.

In a further embodiment, the invention involves a method for identifying a compound that binds to the polypeptide, comprising contacting the compound with the polypeptide in a cell, for a time sufficient to form a polypeptide/compound complex, wherein the complex drives expression of a reporter gene sequence in the cell; and detecting the complex by detecting reporter gene sequence expression, so that if the polypeptide/compound complex is detected, a compound that binds to the polypeptide is identified.

In another embodiment, the invention involves a method of producing the polypeptide, comprising, culturing the host cell for a period of time sufficient to express the polypeptide in said cell; and isolating the polypeptide from the cell culture or cells.

In another aspect, the invention involves a kit comprising the polypeptide. Also provided is a nucleic acid array comprising the polynucleotide or a segment of the polynucleotide attached to a surface. In a further embodiment, the array detects full-matches to the polynucleotide or a unique segment of the polynucleotide. In another embodiment, the array detects mismatches to the polynucleotide or a unique segment of the polynucleotide.

The invention also provides for a method of treatment of a subject in need thereof enhanced activity or expression of stem cell growth factor-like polypeptide comprising administering to the subject a composition selected from the group consisting of a) therapeutic amount of an agonist of said polypeptide; b) a therapeutic amount of the polypeptide; and c) a therapeutic amount of a polynucleotide encoding the polypeptide in form and under conditions such that the polypeptide is produced, and a pharmaceutically acceptable carrier. The invention also provides for a method of treatment of a subject having need to inhibit activity or expression of stem cell growth factor-like polypeptide comprising administering to the subject a composition selected from the group consisting of a) a therapeutic amount of an antagonist of said polypeptide; b) a therapeutic amount of the polynucleotide that inhibits the expression of the nucleotide sequence encoding said polypeptide; and c) a therapeutic amount of a polypeptide that competes with the stem cell growth factor-like polypeptide for its ligand, and a pharmaceutically acceptable carrier.

In another embodiment, the invention involves a polypeptide having stem cell growth factor activity comprising at least ten consecutive amino acids from SEQ ID NO: 10, 13, 16, 32 or 34. In still another embodiment, the invention involves this polypeptide comprising at least ten consecutive amino acids from the C-terminal seventeen amino acids of SEQ ID NO: 10, 13, 16, 32 or 34.

Also provided is a polypeptide with biological activity, said polypeptide comprising at least 272 amino acids and having at least 98% identity with SEQ ID NO: 10 or 34 or said polypeptide comprising at least 273 amino acids and having at least 98% identity with SEQ ID NO: 13.

In a further embodiment, the invention involves an isolated polypeptide with stem cell growth factor activity having at least 90% identity with SEQ ID NO: 10, 13, 16, 32 or 34 and lacking amino acid sequence GIEVTLAEGLTSVSQRTQPTPCRRRYL (SEQ ID NO: 29) wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine.

In yet another embodiment, the invention involves an isolated polypeptide with stem cell growth factor activity having at least 90% identity with SEQ ID NO: 10, 13, 16, 32 or 34 and lacking any 10 consecutive amino acids from amino acid sequence GIEVTLAEGLTSVSQRTQPTPCRRRYL (SEQ ID NO: 29), wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine.

In another embodiment, the invention concerns a method of maintaining or promoting proliferation of a cell selected from the group consisting of primordial germ cells, germ line stem cells, embryonic stem cells, pluripotent cell, and totipotent cells, comprising contacting the cell with an effective amount of a stem cell growth factor-like polypeptide. In a further embodiment, the polypeptide comprises an amino acid sequence of SEQ ID NO: 10, 13, 16, 32 or 34, or comprises an amino acid sequence 90% identical to SEQ ID NO. 10, 13, 16, 32 or 34. In still a further embodiment, the stem cell growth factor-like polypeptide is encoded by a polynucleotide that hybridizes to the complement of a polynucleotide encoding SEQ ID NO: 10, 13, 16, 32 or 34 under stringent hybridization conditions.

The invention also involves an isolated polypeptide with stem cell growth factor activity having at least an amino acid sequence SVSVSTVH (SEQ ID NO: 27) or VSVSTVH (SEQ ID NO: 28), wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine.

In an additional embodiment, the invention concerns the polypeptide according to this invention, wherein the polypeptide comprises one or more motifs selected from the group of a laminin-type EGF-like domain, a membrane attack complex component/perforin domain, and neurohypophysial hormone signature.

The invention also encompasses any polynucleotides encoding a polypeptide according to this invention.

The compositions of the present invention additionally include vectors, including expression vectors, containing the polynucleotides of the invention, cells genetically engineered to contain such polynucleotides and cells genetically engineered to express such polynucleotides.

The isolated polynucleotides of the invention include, but are not limited to, a polynucleotide comprising any one of the nucleotide sequences set forth in the SEQ ID NO: 9, 11, 12, 31 or 33; a polynucleotide comprising any of the full length protein coding sequences of the SEQ ID NO: 9, 11, 12, 31 or 33; and a polynucleotide comprising any of the nucleotide sequences of the mature protein coding sequences of the SEQ ID NO: 9, 11, 12, 31 or 33. The polynucleotides of the present invention also include, but are not limited to, a polynucleotide that hybridizes under stringent hybridization conditions to (a) the complement of any one of the nucleotide sequences set forth in the SEQ ID NO: 9, 11, 12, 31 or 33; (b) a nucleotide sequence encoding SEQ ID NO: 10, 13–24, 32 or 34; a polynucleotide which is an allelic variant of any polynucleotides recited above; a polynucleotide which encodes a species homolog (e.g. orthologs) of any of the proteins recited above; or a polynucleotide that encodes a polypeptide comprising a specific domain or truncation of any of the polypeptides comprising SEQ ID NO: 10, 13–24, 32 or 34.

The nucleic acid sequences of the present invention also include the sequence information from the nucleic acid sequences of SEQ ID NO: 11, 12, 31 or 33. The sequence information can be a segment of any one of SEQ ID NO: 1–7 that uniquely identifies or represents the sequence information of SEQ ID NO: 11, 12, 31 or 33. One such segment can be a twenty-mer nucleic acid sequence because the probability that a twenty-mer is fully matched in the human genome is 1 in 300. In the human genome, there are three billion base pairs in one set of chromosome. Because there are $4^{20}$ possible twenty-mers exist, there are 300 times more twenty-mers than there are base pairs in a set of human chromosome. Using the same analysis, the probability for a seventeen-mer to be fully matched in the human genome is approximately 1 in 5. When these segments are used in arrays for expression studies, fifteen-mer segment can be used. The probability that the fifteen-mer is fully matched in the expressed sequences is also approximately one in five because expressed sequences in one tissue comprise approximately 5% of the entire genome sequence. Preferably, the nucleic acid fragment or subsequence comprise the twenty-one 3' coding nucleotides.

Similarly, when using sequence information for detecting a single mismatch, a segment can be a twenty-five mer. The probability that the twenty-five mer would appear in a human genome with a single mismatch is calculated by multiplying the probability for a full match $(1 \div 4^{25})$ times the increased probability for mismatch at each nucleotide position $(3 \times 25)$. The probability that an eighteen mer with a single mismatch can be detected in an array for expression studies is approximately one in five. The probability that a twenty-mer with a single mismatch can be detected in a human genome is approximately one in five.

A collection as used in this application can be a collection of only one polynucleotide. The collection of sequence information or unique identifying information of each sequence can be provided on a nucleic acid array. In one embodiment, segments of sequence information are provided on a nucleic acid array to detect the polynucleotide that contains the segment. The array can be designed to detect full-match or mismatch to the polynucleotide that contains the segment. The collection can also be provided in a computer-readable format.

This invention also includes the reverse or direct complement of any of the nucleic acid sequences recited above; cloning or expression vectors containing the nucleic acid sequences; and host cells or organisms transformed with these expression vectors.

Human stem cell growth factor-like polypeptide (SEQ ID NO: 10 or 34) is approximately a 272-amino acid protein with a predicted molecular mass of approximately 30 kDa unglycosylated. The mouse homolog is set out in SEQ ID NO:32. Protein database searches with the BLAST algorithm indicate that SEQ ID NO: 10 is homologous to Mus musculus thrombospondin type 1 domain. FIG. 1 shows the alignment of polynucleotide SEQ ID NO: 9 and EST sequences SEQ ID NO: 1–7. The sequences of the present invention (SEQ ID NO: 1–12) are expected to have stem cell growth factor activity, including hematopoietic stem cell growth factor activity, as described herein.

Stem cell growth factor-like polypeptide (SEQ ID NO: 10) also has the following motifs at the designated amino acid sequence corresponding to SEQ ID NO: 10 wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine:

Laminin-type EGF-like (LE) domain proteins at

100 ADCDTCFNKNFCTKCKSGFYLHL 122   (SEQ ID NO: 17)

Vertebrate metallothioneins proteins at

92 INKCTKCKADCDTCFNKNFCTKCKSG-
    FYLHLGKCLDNCPEGLEANN 137   (SEQ ID NO: 18)

Endogenous opioids neuropeptides precursors proteins at

33 MHPNVSQGCQGGCATCSDYN 52    (SEQ ID NO: 19)

Membrane attack complex components/perforin proteins at

145 IVHCEVSEWNPWSPCTKKGKTCGFKRGTETRVREIIQ 181    (SEQ ID NO: 20)

HMG-I and HMG-Y DNA-binding domain proteins (Ahook) at

213 KKGRERKRKK 222    (SEQ ID NO: 21)

HMG1/2 proteins at

198 KCTVQRKKCQKGERGKKGRERKRKKP-NKGESKEAIPDSKSLE 239    (SEQ ID NO: 22)

VERTEBRATE METALLOTHIONEIN SIGNATURE at

104 TCFNKNFCTKCKSG 117    (SEQ ID NO: 23)

NEUROHYPOPHYSIAL HORMONE SIGNATURE at

148 CEVSEWNPWSPCTKKGKTCG 167    (SEQ ID NO: 24)

Motif 100–122, a laminin-type EGF-like domain, is a component of extracellular matrix which promotes cell growth. The membrane attack complex component/perforin domain (145–185) is postulated to mediate cell-cell interaction and thus cell growth and differentiation. Neurohypophysial hormone is itself regulated by many other factors including Interleukin-1 beta and Interleukin-6. The presence of these motifs are expected in stem cell growth factor activity.

Stem cell growth factor-like protein and/or fragments or derivatives would have similar activity to stem cell growth factors and anabolic growth factors and receptors.

The isolated polypeptides of the invention include, but are not limited to, a polypeptide comprising SEQ ID NO: 10, 13–24, 32 or 34; or the corresponding full length or mature protein. Polypeptides of the invention also include polypeptides with biological activity that are encoded by (a) any of the polynucleotides having a nucleotide sequence set forth in the SEQ ID NO: 1–9; 11, 12, 31 or 33 or (b) polynucleotides that hybridize to the complement of the polynucleotides of (a) under stringent hybridization conditions. Biologically or immunologically active variants of any of the protein sequences listed as SEQ ID NO: 10, 13–24, 32 or 34, and "substantial equivalents" thereof (e.g., with at least about 65%, 70%, 75%, 80%, 85%, 90%, 91%, 92%, 93%, 94%, .95%, 96%, 97%, 98% or 99% amino acid sequence identity) that preferably retain biological activity are also contemplated. The polypeptides of the invention may be wholly or partially chemically synthesized but are preferably produced by recombinant means using the genetically engineered cells (e.g. host cells) of the invention.

The invention also provides compositions comprising a polypeptide of the invention. Polypeptide compositions of the invention may further comprise an acceptable carrier, such as a hydrophilic, e.g., pharmaceutically acceptable, carrier.

The invention also provides host cells transformed or transfected with a polynucleotide of the invention.

The invention also relates to methods for producing a polypeptide of the invention comprising growing a culture of the host cells of the invention in a suitable culture medium under conditions permitting expression of the desired polypeptide, and purifying the protein from the culture or from the host cells. Preferred embodiments include those in which the protein produced by such process is a mature form of the protein.

Polynucleotides according to the invention have numerous applications in a variety of techniques known to those skilled in the art of molecular biology. These techniques include use as hybridization probes, use as oligomers, or primers, for PCR, use in an array, use in computer-readable media, use for chromosome and gene mapping, use in the recombinant production of protein, and use in generation of anti-sense DNA or RNA, their chemical analogs and the like. For example, when the expression of an mRNA is largely restricted to a particular cell or tissue type, polynucleotides of the invention can be used as hybridization probes to detect the presence of the particular cell or tissue mRNA in a sample using, e.g., in situ hybridization.

In other exemplary embodiments, the polynucleotides are used in diagnostics as expressed sequence tags for identifying expressed genes or, as well known in the art and exemplified by Vollrath et al., Science 258:52–59 (1992), as expressed sequence tags for physical mapping of the human genome.

A polynucleotide according to the invention can be joined to any of a variety of other nucleotide sequences by well-established recombinant DNA techniques (see Sambrook, J., et al. (1989) Molecular Cloning: A Laboratory Manual, Cold Spring Harbor Laboratory, NY). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The polypeptides according to the invention can be used in a variety of conventional procedures and methods that are currently applied to other proteins. For example, a polypeptide of the invention can be used to generate an antibody that specifically binds the polypeptide. Such antibodies, particularly monoclonal antibodies, are useful for detecting or quantitating the polypeptide in tissue. The polypeptides of the invention can also be used as molecular weight markers, and as a food supplement.

Methods are also provided for preventing, treating, or ameliorating a medical condition which comprises the step of administering to a mammalian subject a therapeutically effective amount of a composition comprising a protein of the present invention and a pharmaceutically acceptable carrier.

In particular, the polypeptides and polynucleotides of the invention can be utilized, for example, as part of methods for the prevention and/or treatment of disorders involving aberrant protein expression or biological activity.

The methods of the invention also provides methods for the treatment of disorders as recited herein which may involve the administration of the polynucleotides or polypeptides of the invention to individuals exhibiting symptoms or tendencies related to disorders as recited herein. In addition, the invention encompasses methods for treating diseases or disorders as recited herein comprising the step of administering compounds and other substances that modulate the overall activity of the target gene products. Compounds and other substances can effect such modulation either on the level of target gene/protein expression or target protein activity. Specifically, methods are provided for preventing, treating or ameliorating a medical condition, including neurological diseases, which comprises administering to a mammalian subject, including but not limited to humans, a therapeutically effective amount of a composition comprising a polypeptide of the invention or a therapeutically effective amount of a composition comprising a binding partner of (e.g., antibody specifically reactive for) stem cell growth factor-like polypeptides of the invention. The mechanics of the particular condition or pathology will dictate whether the polypeptides of the invention or binding partners (or inhibitors) of these would be beneficial to the individual in need of treatment.

The invention also provides a method of promoting wound healing comprising administering a stem cell growth factor-like polypeptide of the present invention to the site of a wound or injury. The invention provides a method of promoting cell growth and morphogenesis comprising administering a stem cell growth factor-like polypeptide of the present invention to a medium of nerve cells. According to this method, polypeptides of the invention can be administered to produce an in vitro or in vivo promotion of cellular function. A polypeptide of the invention can be administered in vivo as a stem cell growth factor alone or as an adjunct to other therapies.

The invention further provides methods for manufacturing medicaments useful in the above described methods.

The present invention further relates to methods for detecting the presence of the polynucleotides or polypeptides of the invention in a sample (e.g., tissue or sample). Such methods can, for example, be utilized as part of prognostic and diagnostic evaluation of disorders as recited herein and for the identification of subjects exhibiting a predisposition to such conditions. The invention also provides kits comprising polynucleotide probes and/or monoclonal antibodies, and optionally quantitative standards, for carrying out methods of the invention. Furthermore, the invention provides methods for evaluating the efficacy of drugs, and monitoring the progress of patients, involved in clinical trials for the treatment of disorders as recited above.

The invention also provides methods for the identification of compounds that modulate (i.e., increase or decrease) the expression or activity of the polynucleotides and/or polypeptides of the invention. Such methods can be utilized, for example, for the identification of compounds that can ameliorate symptoms of disorders as recited herein. Such methods can include, but are not limited to, assays for identifying compounds and other substances that interact with (e.g., bind to) the polypeptides of the invention.

4. BRIEF DESCRIPTION OF THE DRAWINGS

FIG. 1 shows the alignment of SEQ ID NO. 9 with SEQ ID NO. 1–7.

FIG. 2 shows the BLASTP amino acid sequence alignment between the SEQ ID NO: 10, stem cell growth factor-like polypeptide and mouse thrombospondin type 1 domain protein SEQ ID NO: 25, indicating that the two sequences share 64% similarity over amino acid residues 19–254 of SEQ ID NO: 10 and 47% identity over the same amino acid residues 19–254 of SEQ ID NO: 10, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIG. 3 shows the BLASTP amino acid sequence alignment between the SEQ ID NO: 10, stem cell growth factor-like polypeptide and human secreted protein clone da228_6 protein (Patent Application No. WO98/49302), SEQ ID NO: 26, indicating that the two sequences share 100% similarity over amino acid residues 1–265 of SEQ ID NO: 10 and 100% identity over the same amino acid residues 1–265 of SEQ ID NO: 10, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

Figure 6:
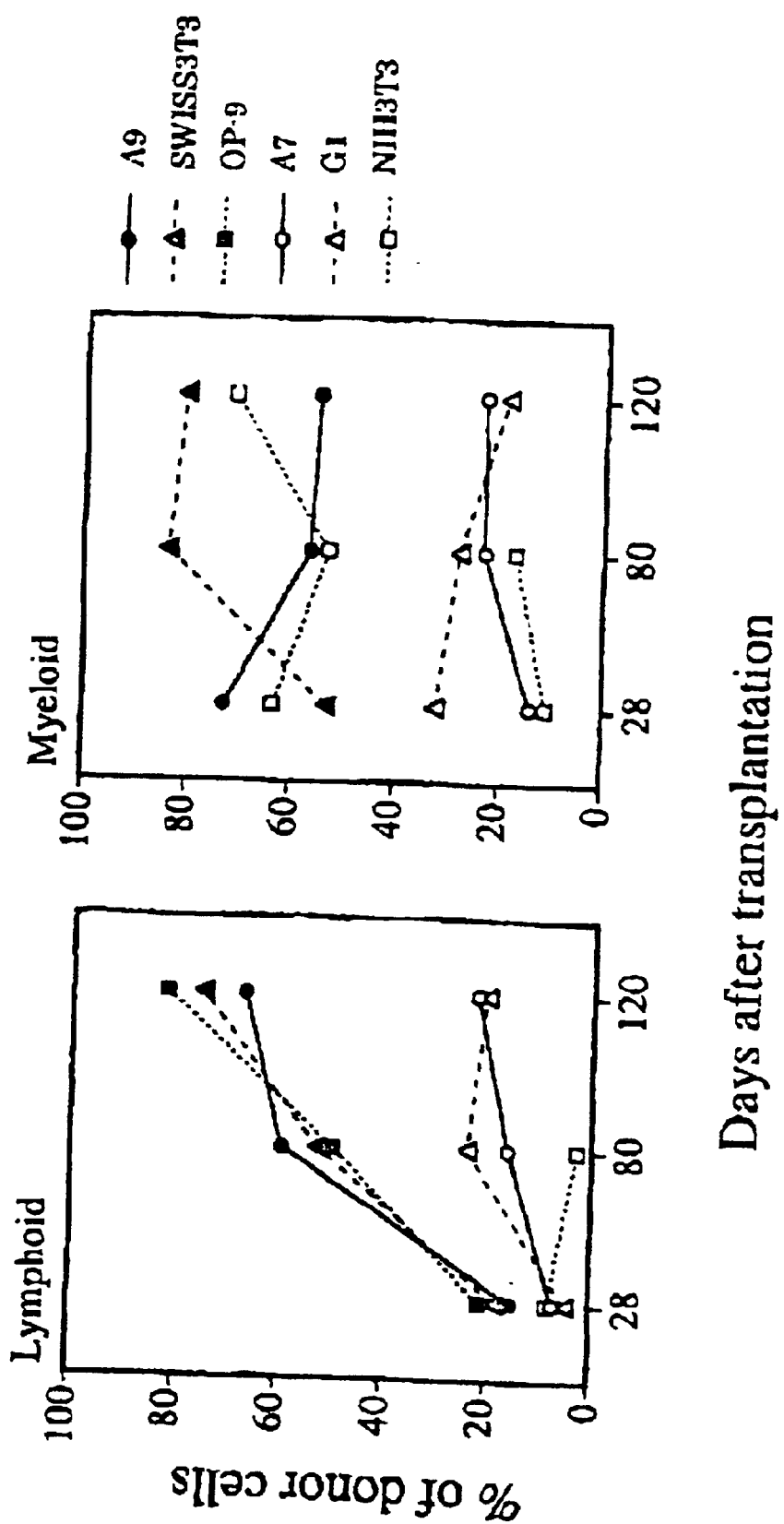
Figure 7:
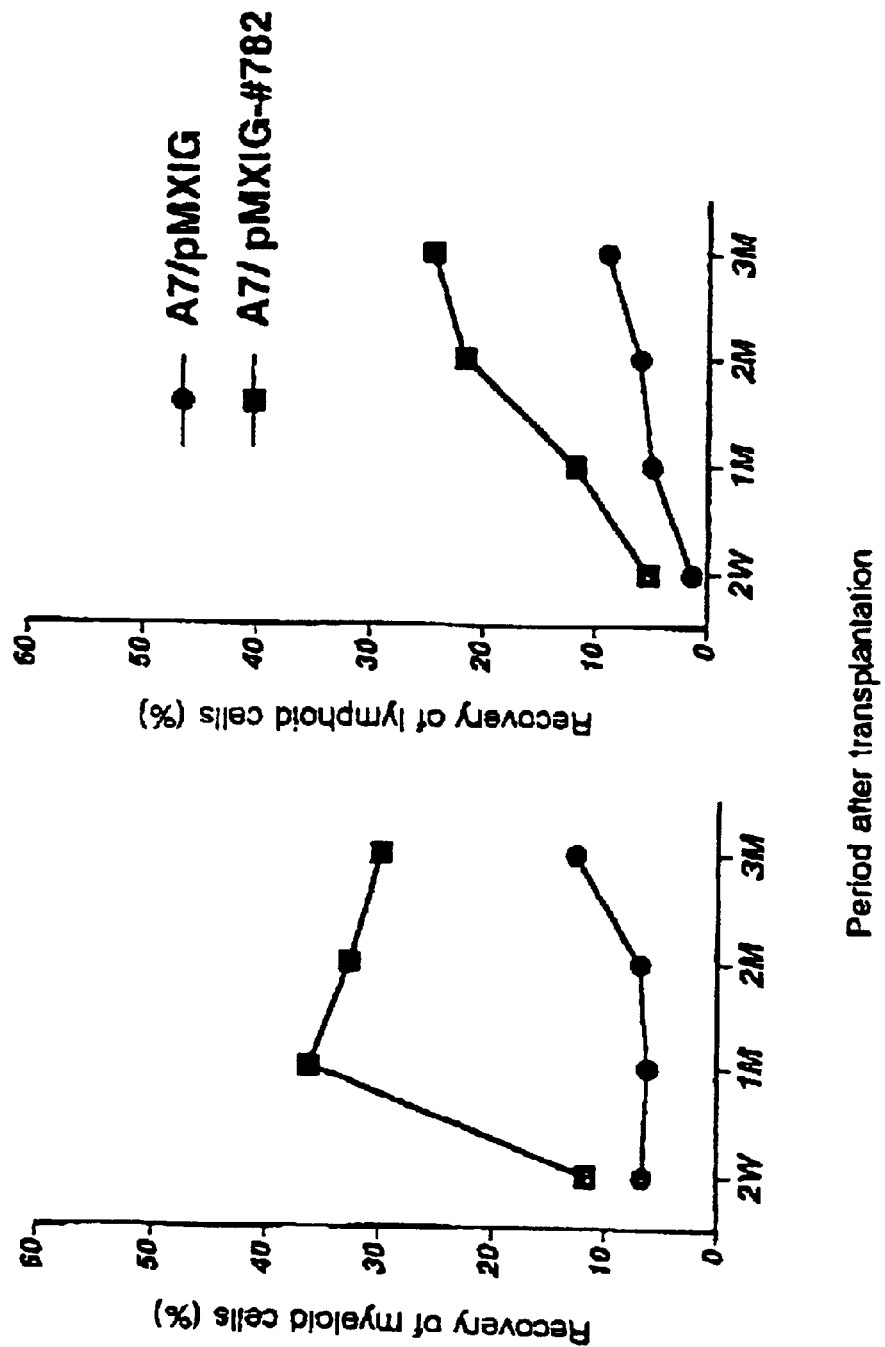

FIG. 6 shows time course of donor derived lymphoid lineage cells or myeloid lineage cells reconstitution in irradiated recipient mice that received the hematopoietic stem cells co-cultured with stromal cells; and FIG. 7 shows time course of donor derived lymphoid lineage cells or myeloid lineage cells reconstitution in irradiated recipient mice that received the hematopoietic stem cells co-cultured with AGM-s3-A7 cell lines (A7/pMXIG-SCR-1 and A7/pMXIG) transfected with a vector including SCR-1 (pMXIG-SCR-1) or a vector which does not include SCR-1 (pMXIG).

5. DETAILED DESCRIPTION OF THE INVENTION 5.1 Definitions

The term "primordial germ cells (PGCs)" refers to a small population of cells set aside from other cell lineages particularly from the yolk sac, mesenteries, or gonadal ridges during embryogenesis that have the potential to differentiate in to germ cells and other cells. PGCs are the source from which GSCs and ES cells are derived The term "germ line stem cells (GSCs)" refers to stem cells derived from primordial stem cells that provide a steady and continuous source of germ cells for the production of gametes.

The term "embryonic stem cells (ES)" refers to a cell which can give rise to many differentiated cell types in an embryo or an adult, including the germ cells. The PGCs, the GSCs and the ES cells are capable of self-renewal. Thus these cells not only populate the germ line and give rise to a plurality of terminally differentiated cells which comprise the adult specialized organs, but are able to regenerate themselves.

The term "totipotent" refers to the capability of a cell to differentiate into all of the cell types of an adult organism.

The term "pluripotent" refers to the capability of a cell to differentiate into a number of differentiated cell types that are present in an adult organism. A pluripotent cell is restricted in its differentiation capability in comparison to a totipotent cell.

The term "nucleotide sequence" refers to a heteropolymer of nucleotides or the sequence of these nucleotides. The terms "nucleic acid" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" is a sequence of nucleotide residues which is long enough to use in polymerase chain reaction (PCR) or various hybridization procedures to identify or amplify identical or related parts of mRNA or DNA molecules. A fragment or segment may uniquely identify each polynucleotide sequence of the present invention.

The terms "oligonucleotides" or "nucleic acid probes" are prepared based on the polynucleotide sequences provided in the present invention. Oligonucleotides comprise portions of such a polynucleotide sequence having at least about 15 nucleotides and usually at least about 20 nucleotides. Nucleic acid probes comprise portions of such a polynucleotide sequence having fewer nucleotides than about 6 kb, usually fewer than about 1 kb. After appropriate testing to eliminate false positives, these probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241–250).

The term "probes" includes naturally occurring or recombinant or chemically synthesized single- or double-stranded nucleic acids. They may be labeled by nick translation, Klenow fill-in reaction, PCR, or other methods well known in the art. Probes of the present invention, their preparation and/or labeling are elaborated in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York N.Y., both of which are incorporated herein by reference in their entirety.

The term "stringent" is used to refer to conditions that are commonly understood in the art as stringent. Stringent conditions can include highly stringent conditions (i.e., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C.), and moderately stringent conditions (i.e., washing in 0.2×SSC/0.1% SDS at 42° C.). Other exemplary hybridization conditions are described herein in the examples.

In instances of hybridization of deoxyoligonucleotides, additional exemplary stringent hybridization conditions include washing in 6×SSC/0.05% sodium pyrophosphate at 37° C. (for 14-base oligos), 48° C. (for 17-base oligos), 55° C. (for 20-base oligos), and 60° C. (for 23-base oligos).

The term "recombinant," when used herein to refer to a polypeptide or protein, means that a polypeptide or protein is derived from recombinant (e.g., microbial, insect, or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., E. coli, will be free of glycosylation modifications; polypeptides or proteins expressed in yeast will have a glycosylation pattern in general different from those expressed in mammalian cells.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an amino terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "open reading frame," ORF, means a series of nucleotide triplets coding for amino acids without any termination codons and is a sequence translatable into protein.

The term "expression modulating fragment," EMF, means a series of nucleotides which modulates the expression of an operably linked ORF or another EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event.

As used herein, an "uptake modulating fragment," UMF, means a series of nucleotides which mediate the uptake of a linked DNA fragment into a cell. UMFs can be readily identified using known UMFs as a target sequence or target motif with the computer-based systems described below.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

The term "active" refers to those forms of the polypeptide which retain the biologic and/or immunologic activities of any naturally occurring polypeptide. According to the invention, the term "biologically active" means that the polypeptide retains at least one of the biological activities of the polypeptide of the invention. The term "stem cell growth factor activity" or "stem cell growth factor-like activity" refers to biological activity that is similar to the biological activity of stem cell growth factor polypeptide, such as cell growth or morphogenesis activity.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "derivative" refers to polypeptides chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins.

The term "variant" (or "analog") refers to any polypeptide differing from naturally occurring polypeptides by amino acid insertions, deletions, and substitutions, created using, e g., recombinant DNA techniques. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

As used herein, "substantially equivalent" or "substantially similar" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 35% (i.e., the number of individual residue substitutions, additions, and/or deletions in a substantially equivalent sequence, as compared to the corresponding reference sequence, divided by the total number of residues in the substantially equivalent sequence is about 0.35 or less). Such a sequence is said to have 65% sequence identity to the listed sequence. In one embodiment, a substantially equivalent, e.g., mutant, sequence of the invention varies from a listed sequence by no more than 30% (70% sequence identity); in a variation of this embodiment, by no more than 25% (75% sequence identity); and in a further variation of this embodiment, by no more than 20% (80% sequence identity) and in a further variation of this embodiment, by no more than 10% (90% sequence identity) and in a further variation of this embodiment, by no more that 5% (95% sequence identity). Substantially equivalent, e.g., mutant, amino acid sequences according to the invention preferably have at least 80% sequence identity with a listed amino acid sequence, more preferably at least 85% sequence identity, more preferably at least 90% sequence identity, more preferably at least 95% sequence identity, more preferably at least 98% sequence identity, and most preferably at least 99% sequence identity. Substantially equivalent nucleotide sequence of the invention can have lower percent sequence identities, taking into account, for example, the redundancy or degeneracy of the genetic code. Preferably, the nucleotide sequence has at least about 65% identity, more preferably at least about 75% identity, more preferably at least about 80% sequence identity, more preferably at least 85% sequence identity, more preferably at least 90% sequence identity, more preferably at least about 95% sequence identity, more preferably at least 98% sequence identity, and most preferably at least 99% sequence identity. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded. Sequence identity may be determined, e.g., using the Jotun Hein method (Hein, J. (1990) Methods Enzymol. 183:626–645). Identity between sequences can also be determined by other methods known in the art, e.g. by varying hybridization conditions.

Nucleic acid sequences encoding such substantially equivalent sequences, e.g., sequences of the recited percent identities can routinely be isolated and identified via standard hybridization procedures well known to those of skill in the art.

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biological and/or immunological activity.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

The term "activated" cells as used in this application are those which are engaged in extracellular or intracellular membrane trafficking, including the export of secretory or enzymatic molecules as part of a normal or disease process.

The term "purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "infection" refers to the introduction of nucleic acids into a suitable host cell by use of a virus or viral vector.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed.

The term "intermediate fragment" means a nucleic acid between 5 and 1000 bases in length, and preferably between 10 and 40 bp in length.

The term "secreted" includes a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum. "Secreted" proteins are also intended to include proteins containing non-typical signal sequences (e.g. Interleukin-1 Beta, see Krasney, P. A. and Young, P. R. (1992) Cytokine 4(2):134–143) and factors released from damaged cells (e.g. Interleukin-1 Receptor Antagonist, see Arend, W. P. et. al. (1998) Annu. Rev. Immunol. 16:27–55)

Each of the above terms is meant to encompasses all that is described for each, unless the context dictates otherwise.

5.1.1 Description of the Invention

Since stromal cells can support the proliferation or the survival of hematopoietic stem cells or hematopoietic progenitor cells ex vivo, stromal cells are expected to produce factors mediating support proliferation or survival of hematopoietic stem cells or hematopoietic progenitor cells, as defined herein.

An object of the present invention is to provide a factors supporting proliferation or survival of hematopoietic stem cells or hematopoietic progenitor cells and these factors are/can be derived from the stromal cells.

Mouse stromal cells produce factors supporting the proliferation or the survival of hematopoietic stem cells or hematopoietic progenitor cells, as mentioned above. Attention is given that there are two kinds of stromal cells. One has an ability to support the proliferation or survival of hematopoietic stem cells or hematopoietic progenitor cells (hereafter sometimes referred to as "activity to support hematopoietic stem cells"). The other does not have the activity to support hematopoietic stem cells. This difference in the abilities maybe due to differential expression of the factors that facilitate supporting hematopoietic stem cells or progenitor cells at the transcription level. That is to say it is speculated that the supportive stromal cells express at high levels of mRNAs coding the factors and that non-supportive stromal cells express less mRNAs. Thus mRNAs that code for the factors maybe among the genes expressed higher in the supportive cells compared to in the non-supportive cells. In this context, the inventors confirmed the hematopoietic stem and/or progenitor cell supporting ability of AGM-s3-A9, AGM-s3-D11, OP9, and SWISS3T3 cell lines and the non-supportive ability of AGM-s3-A7, AGM-s3-G1, and NIH3T3 cell lines (AGM-s3-A9, AGM-s3-D11, AGM-s3-A7, and AGM-s3-G1 cell lines are obtained by subcloning the stromal cell strain AGM-s3 derived from AGM disclosed in the prior application WO99/03980). Next, the genes that are highly expressed in AGM-s3-A9, AGM-s3-D11, OP9, and 3T3Swiss cell lines and show low expression or are undetected in AGM-s3-A7, AGM-s3-G1, and NIH3T3 cell lines were identified. After the assessment of the abilities of supporting the proliferation or the survival of the hematopoietic stem cells or the hematopoietic progenitor cells of these gene groups and careful examinations, the present invention has been completed.

That is, the present invention provides the followings.

(1) A DNA coding for a polypeptide as defined in the following (A) or (B):

(A) a polypeptide which has an amino acid sequence comprising at least amino acid residues 22 to 279 of SEQ ID NO: 32, or an amino acid sequence comprising at least amino acid residues 22 to 272 of SEQ ID NO: 34; or (B) a polypeptide which has an amino acid sequence including deletion, substitution or insertion of one or several amino acids in the amino acid sequence comprising at least amino acid residues 22 to 279 of SEQ ID NO: 32, or an amino acid sequence comprising at least amino acid residues 22 to 272 of SEQ ID NO: 34, and which has an activity to support proliferation or survival of hematopoietic stem cell or hematopoietic progenitor cell, with a proviso that C-terminal amino acid sequence dose not comprise the amino acid sequence of SEQ ID NO: 45.

(2) The DNA according to (1), which is a DNA as defined in the following (a) or (b):
(a) a DNA which comprises at least nucleotides 574 to 1347 of SEQ ID NO: 31; or
(b) a DNA which is hybridizable with the nucleotide sequence of SEQ ID NO: 31 or a probe or fragment prepared from the sequence, under the stringent condition, and which has an activity to support proliferation or survival of hematopoietic stem cell or hematopoietic progenitor cell.
(3) The DNA according to (2), the stringent condition is 6×SSC 5×Denhardt, 0.5% SDS and 68° C. (SSC 3M NaCl, 0.3M sodium citrate, 50×Denhardt 1% BSA 1% polyvinyl pyrrolidone, 1% Ficoll 400, or 6×SSC, 5×Denhardt, 0.5% SDS, 50% formamide and 42° C.
(4) The DNA according to (1), which is a DNA as defined in the following (a) or (b):
(a) a DNA which comprises at least nucleotides 321 to 1074 of SEQ ID NO: 33; or
(b) a DNA which is hybridizable with the nucleotide sequence of SEQ ID NO: 33 or a prove prepared from the sequence, under the stringent condition, and which has an activity to support proliferation or survival of hematopoietic stem cell or hematopoietic progenitor cell.
(5) The DNA according to (4), the stringent condition is 6×SSC 5×Denhardt 0.5% SDS and 68° C. (SSC 3M NaCl, 0.3M sodium citrate, 50×Denhardt 1% BSA 1% polyvinyl pyrrolidone, 1% Ficoll 400 , or 6×SSC, 5×Deanhardt, 0.5% SDS, 50% Formamide and 42° C.
(6) A expression vector which comprises a DNA of any one of (1) to (5) or other polynucleotides of the invention in such a manner that the DNA can be expressed.
(7) A cell which is introduced (i.e., transformed or transfected) with a DNA of any one of (1) to (5) or other polynucleotides of the invention in such a manner that the DNA can be expressed.
(8) A polypeptide (An isolated polypeptide) which is an expression product of a DNA according to any one of (1) to (5) or other polynucleotides of the invention, the polypeptide having an activity to support proliferation or survival of hematopoietic stem cells or hematopoietic progenitor cells, with a proviso that C-terminal amino acid sequence dose not comprise the amino acid sequence of SEQ ID NO: 14.
(9) The polypeptide according to (8), which has an amino acid sequence comprising at least amino acid residues 22 to 279 of SEQ ID NO: 32, or an amino acid sequence including deletion, substitution or insertion of one or several amino acids in the amino acid sequence comprising at least amino acid residues 22 to 279 of SEQ ID NO: 32.
(10) The polypeptide according to (8), which has an amino acid sequence comprising at least amino acid residues 22 to 272 of SEQ ID NO: 34, or an amino acid sequence including deletion, substitution or insertion of one or several amino acids in the amino acid sequence comprising at least amino acid residues 22 to 272 of SEQ ID NO: 34.
(11) The polypeptide according to (8) or other polypeptides of the invention, which is modified with one or more modifying agent selected from the group consisting of polyethylene glycol (PEG), dextran, poly(N-vinyl-pyrrolidone), polypropylene glycol homopoymer, copolymer of polypropylene oxide/ethylene oxide, polyoxyethylated polyol and polyvinyl alcohol.
(12) Pharmaceutical composition having an effect to support proliferation or survival of hematopoietic stem cells or hematopoietic progenitor cells, which comprises the polypeptide as defined in the following (A) (B) or (C): (A) a polypeptide which has an amino acid sequence comprising at least amino acid residues 22 to 279 of SEQ ID NO: 32, or an amino acid sequence comprising at least amino acid residues 22 to 272 of SEQ ID NO: 34; or
(B) a polypeptide which has an amino acid sequence including deletion, substitution or insertion of one or several amino acids in the amino acid sequence comprising at least amino acid residues 22 to 279 of SEQ ID NO: 32, or an amino acid sequence comprising at least amino acid residues 22 to 272 of SEQ ID NO: 34, and which has an activity to support proliferation or survival of hematopoietic stem cell or hematopoietic progenitor cell, or
(C) any of the other polypeptides of the invention described therein.
(13) A monoclonal antibody which binds to the polypeptide of (9) to (11).

Terms used in this specification are defined as follows.

A hematopoietic stem cell is defined as a cell having totipotency, that is, a capacity to differentiate into all the cell lineages of the hematopoietic cells, and simultaneously having a potency of self-renew with retaining the totipotency. Erythrocyte precursor cells hardly survive and proliferate in vitro culture circumstances and rapidly disappear. If the survival and the proliferation of the erythrocyte precursor cells are confirmed, continuous production of the erythrocyte precursor cells seems to occur due to the survival and/or the proliferation of the more immature hematopoietic stem cells or the hematopoietic progenitor cells. Therefore, to assess the survival and/or proliferation of the human hematopoietic stem cells, to enumerate the erythrocyte precursor cells ((BFU-E, CFU-E, and CFU-Emix) in cultures is an appropriate way.

A hematopoietic progenitor cell is defined as a cell which can differentiate a single cell lineage of the hematopoietic lineage or a plural cell lineages but cannot differentiate into all of the cell lineages. A stromal cell is defined as a cell which can be co-cultured together with the hematopoietic stem cells in vitro to simulate in vivo hematopoietic environment. Cells derived from any origin can be used as long as the cells can be co-cultured with the hematopoietic cells in vitro.

Polypeptides in accordance with the present invention have an activity to support proliferation or survival of hematopoietic stem cells or hematopoietic progenitor cells. The concrete embodiment of the polypeptides in accordance with the present invention are an expressed product (hereafter sometimes referred to as a mouse "supporting factor for the proliferation of stem cells") of a gene named SCR-1 isolated from a mouse stromal cell (hereafter sometimes referred to as "mouse SCR-1") and an expressed product (hereafter sometimes referred to as a human "supporting factor for the proliferation of stem cells") of a human orthologous gene thereof (hereafter sometimes referred to as "human SCR-1"). The term SCR-1 may be used herein to refer to the polypeptide sequences set out in SEQ ID NO: 10, 13, 16, 32 and 34 which are respectively encoded by the polnucleotide sequences set out in SEQ ID NOS: 9, 11, 12, 31 and 33.

Although an amino acid sequence of the expressed product of human SCR-1 (SEQ ID NO: 34) has homology at 97.4% with the known polypeptide (WO98/49302) whose function has not been clear, the amino acid sequence at the C-terminal region thereof differs, so that it is a novel polypeptide. A part of the amino acid sequence in the above described polypeptide having unknown functions which is different from that in SEQ ID NO: 34 is shown in SEQ ID NO: 45. On the other hand, mouse SCR-1 has homology at 84.6% with the above-described polypeptide.

The above described homologies are calculated as percentage of the number of same amino acids to the total number of amino acids using a comparison manually (266/273 and 237/280, respectively).

The supporting factor for the proliferation of stem cells, that is, the polypeptides in accordance with the present invention can be produced by preparing transformed cells by transducing mouse or human SCR-1 into appropriate host cells and by expressing the DNAs in the transformed cells. When DNA including a nucleotide sequence shown in SEQ ID NO: 31 is used as SCR-1, a mouse supporting factor for the proliferation of stem cells is obtained. When DNA including a nucleotide sequence shown in SEQ ID NO: 33 is used as SCR-1, a human supporting factor for the proliferation of stem cells is obtained. The mouse supporting factor for the proliferation of stem cells and the human supporting factor for the proliferation of stem cells comprise amino acid sequences represented by SEQ ID NO: 32 and SEQ ID NO: 34, respectively. These supporting factors for the proliferation of stem cells are precursors including signal peptides, and are assumed to be processed to mature supporting factors for the proliferation of stem cells in mouse or human cells. As based on the results of Signal P test which searches breakage sites of the signal peptides in these amino acid sequences (Nielsen H., *protein Engineering*, 10: 1–6, 1997; Nielsen H., *Int. J. Neural Sys.*, 8: 581–599, 1997), the breakage or cleavage sites seem to exist between the amino acid 21 and the amino acid 22 in the amino acid sequences of SEQ ID NO: 32 and SEQ ID NO: 34.

The mouse mature supporting factor for the proliferation of stem cells comprises the amino acid sequence represented by amino acids 22 to 279 of SEQ ID NO: 32. The human mature supporting factor for the proliferation of stem cells comprises the amino acid sequence represented by amino acids 22 to 272 of SEQ ID NO: 34.

When supporting factors for the proliferation of stem cells are prepared, SCR-1 which is transferred into host cells may be DNA coding precursor polypeptide or DNA coding mature polypeptide. An example of the DNA coding the mouse mature supporting factor for the proliferation of stem cells comprises the DNA comprising at least a nucleotide sequence consisting of nucleotide numbers 574 to 1347 of SEQ ID NO: 31. An example of the DNA coding the human mature supporting factor for the proliferation of stem cells comprises the DNA comprising at least a nucleotide sequence consisting of nucleotide numbers 321 to 1074 of SEQ ID NO: 33.

DNA in accordance with the present invention may code the above described factors which have amino acid sequences including substitution, deletion or insertion of one or several amino acids, as long as the activity of the supporting factor for the proliferation of stem cells to be coded is not lost. DNAs coding substantially identical polypeptides to this supporting factor for the proliferation of stem cells are obtained by modifying the nucleotide sequences so as to include substitution, deletion, insertion, addition, or inversion of amino acid residues in a specific region using site-directed mutagenesis.

The DNAs including the above described mutation can be expressed in appropriate cells and the activity to support the hematopoietic stem cells of the expressed products can be examined, so that the DNAs coding the polypeptide having functions which are substantially identical to this supporting factor for the proliferation of stem cells are obtained. In addition, the DNAs coding substantially identically active protein as this supporting factor for the proliferation of stem cells can be obtained by hybridization with DNAs including, for example, the nucleotide sequence as described in SEQ ID NO: 1 or SEQ ID NO: 3 from the cells having thereof, or probes prepared from these DNAs under the stringent condition; and by isolating the DNAs coding the protein possessing the activity to support the hematopoietic stem cells. The stringent condition is, for example, one in which DNAs having homology at not less than 70%, preferably at not less than 80%, are hybridized each other and DNAs having less homology than those are not hybridized each other. The above described stringent condition is 6×SSC, 5×Denhardt, 0.5% SDS, 68° C. (SSC; 3M NaCl, 0.3M sodium citrate) (50×Denhardt; 1% BSA, 1% polyvinyl pyrrolidone,1% Ficoll 400) or 6×SSC, 5×Deanhardt, 0.5% SDS, 50% Formamide, 42° C., or the like. Strategy of hybridization is further defined by final wash conditions as set out herein.

Microorganisms such as *Escherichia coli* and yeast, culture cells derived from animals or plants, and the like are used for host cells for expressing SCR-1. Preferably, culture cells derived from mammals are used as the host cells. In the case that prokaryotic cells are used as the host cells, the expression is preferably performed in a condition in which a signal peptide region is replaced with a leader sequence suitable for the prokaryotic cells such as -lactamase (bla), alkaline phosphatase (phoA), and outer membrane protein A (ompA) and the like, or in a form in which a methionine residue is added to the N-terminal site of the mature protein.

The supporting factor for the proliferation of stem cells obtained as above may be added with sugar chains at any of positions 23, 36 and 137, alone, or a plurality of positions thereof in mouse SCR-1. The supporting factor for the proliferation of stem cells obtained as above may be added with sugar chains at any of positions 23, 36, 137 or 194, alone, or a plurality of positions thereof in human SCR-1.

For example, SCR-1 is integrated into a vector corresponding to the host in a form capable of expression and the obtained recombinant vector is transferred into the host cells, so that the transfer of SCR-1 into the host cells is completed.

Examples of the culture cells derived from mammals are CHO cells, 293 cells, COS7 cells, and the like. Gene expression regulatory sequence such as a promoter to express SCR-1 may be originated from SCR-1 itself, or may be derived from other genes such as cytomegalovirus promoter and elongation factor 1 promoter and the like.

Examples of a vector for animal culture cells are plasmid vectors, retrovirus vectors, adenovirus vectors (Neering, S. J., *Blood*, 88: 1147, 1996), herpes virus vectors (Dilloo, D., *Blood*, 89: 119, 1997), HIV vectors, and the like.

In order to transfer the recombinant vector into culture cells, the conventional methods which are usually employed for transformation of culture cells such as calcium phosphate transfection, liposome method, DEAE dextran method, electroporation and microinjection method are employed.

The polypeptides in accordance with the present invention also comprise polypeptides having amino acid sequences in which one or several amino acids are substituted, deleted or inserted in the amino acid sequence represented in SEQ ID NO: 32 or SEQ ID NO: 34 or other polynucleotides of the invention, and having activity to support the hematopoietic stem cells in addition to the polypeptides having the amino acid sequence represented in SEQ ID NO: 32 or SEQ ID NO: 34 or other polynucleotides of the invention. That is, even if a mouse and a human supporting factor for the proliferation of stem cells is modified by substitution, deletion, insertion or the like, polypeptides holding essential functions as a supporting factor for the proliferation of stem cells can be considered to be substantially identical with the supporting factor for the proliferation of stem cells. The above described "several" denotes ranging from two to 110, and preferably ranging from two to 55 as a total number depending on the region of polypeptide in accordance with the present invention.

These modified supporting factors for the proliferation of stem cells can be obtained by treating DNA coding the supporting factors for the proliferation of stem cells or host cells including the above mentioned DNA with mutagens, or by mutating the above mentioned DNA so as to substitute, delete, or insert an amino acid at a specific site using site-directed mutagenesis. The residual of the activity to support hematopoietic stem cells in the obtained mutant polypeptides is confirmed by the examples described below. That is, after the cultured hematopoietic stem cells which express the mutant polypeptides are transferred into irradiated mice, peripheral hematological cellularity after the transfer may be observed over time.

Since the nucleotide sequences of the invention have been described, the modified supporting factor for the proliferation of stem cells can be also obtained by isolating the corresponding DNAs from mouse or human cDNA or chromosome DNA libraries using PCR in which the oligonucleotides prepared based on these nucleotide sequences are used as primers or using hybridization in which the oligonucleotides prepared based on these nucleotide sequences are used as probes.

In one aspect, the DNAs in accordance with the present invention was isolated from cDNA library of AGM-s3-A9 cells which are a mouse stromal cell strain having the activity to support hematopoietic stem cells using SBH (Sequencing By Hybridization) method (Drmanac, S., *Nat. Biotechnol.*, 16. 54, 1998; Drmanac, R., *Methods. Enzymol.*, 303, 165, 1999) as described below. The mouse stromal cell lines having the activity to support hematopoietic stem cells can be obtained using the method disclosed in WO99/03980 or from Cell Development Bank of Institute of Physical and Chemical Research (RIKEN) or ATCC.

An outline of SBH method will be described below. Probes including eight or nine nucleotides whose sequences are different from each other are prepared. When the nucleotide sequences corresponding to those of the probe exist in targeted gene, the probes can hybridize with the gene. The hybridization can be easily detected with utilization of radio isotope or fluorescence conjugated probes. Each clone in the library is picked up, and blotted on a membrane. Then, repeated hybridizations are performed with the above described probes, so that one can identify the combination of probes that hybridize to each clone. Since the combination of probes that hybridize to each gene depend on the sequences of clones, identical genes have identical signature hybridization patterns with the probes. That is, the same gene can be identified as a one group (cluster) according to the signature of the hybridized probes. The number of clones derived from each gene in the library can be determined by clustering and counting the members of the clusters based on the hybridization profiles of the probes. Thus, incidence of expression of each gene in the library can be determined.

Clustering analysis was performed for cDNA libraries derived from supportive and non-supportive stromal cell lines. Thus, incidences of expressed genes among cells were compared, so that the genes specifically highly expressed in the supportive stromal cell lines were selected. The incidences of these genes in each cell were further examined by Northern blot analysis, so that genes which highly expressed in the cells having activity to support the hematopoietic stem cells were obtained.

SCR-1 is one of the genes which was highly expressed with specificity in the supporting cells obtained through the above described process. After clustering and analyzing using Northern blot analysis, the gene comprising nucleotide numbers 1032 to 1484 of SEQ ID NO: 31 was identified. The complete gene encoding SCR-1 was cloned from the cDNA library derived from AGM-s3-A9 cells.

Further, in order to assess supporting ability for hematopoiesis of SCR-1, a gene fragment including ORF (nucleotide numbers 511 to 1350 of SEQ ID NO: 31) in SCR-1 gene was transferred into stromal cells (AGM-s3-A7 cell) which cannot support the hematopoietic stem cells using a retrovirus vector, and assessed the change in the activity to support the hematopoietic stem cells of the stromal cells. Substantially, after the stromal cells which were not transferred with the gene and those which were transferred with the gene were independently co-cultured with the mouse hematopoietic stem cells, the hematopoietic cells were transplanted into irradiated mice. Engraftment of the co-cultured hematopoietic cells in recipient mice were examined. As a result, the mice transplanted with the hematopoietic stem cells which were co-cultured with the AGM-s3-A7 cell line transferred with SCR-1 showed increased chimerism after the transplantation compared with the AGM-s3-A7 cell line which were not transferred with SCR-1 gene. This result shows that the AGM-s3-A7 stromal cells that express SCR-1 have obtained supporting activity for the proliferation or survival of the hematopoietic stem cells or the hematopoietic progenitor cells. As a result, it has become evident that SCR-1 has a function to add the above described activity to the stromal cells that originally do not posses the activities for supporting proliferation or survival of hematopoietic stem cells or hematopoietic progenitor cells. Therefore, it was revealed that SCR-1 has an activity to support the survival or the proliferation of the hematopoietic stem cell or the hematopoietic progenitor cell, or has an activity to add an activity to support the hematopoietic stem cells to stromal cells.

The polypeptides in accordance with the present invention can be used as a medicine to proliferate or support human hematopoietic stem cell or human hematopoietic progenitor cell. This pharmaceutical composition can be used for supporting proliferation or survival of human hematopoietic stem cells or human hematopoietic progenitor cells ex vivo. It is of problem for hematopoietic stem cell transplantation therapies such as peripheral blood stem cell transplantation and cord blood stem cell transplantation that sometimes sufficient amount of the hematopoietic stem cells cannot be collected and the transplantation may not be performed. Even if enough stem cells could not be collected, a sufficient amount of the hematopoietic stem cells could be obtained (and transplanted) by amplification of the hematopoietic stem cells in vitro using polypeptides of the invention. That is, hematopoietic stem cells can be amplified without differentiation by culturing the hematopoietic stem cells in culture medium including polypeptides of the invention. It may be considered the hematopoietic stem cells are able to be amplified more efficiently with addition of a variety of cytokines to the medium.

When hematopoietic stem cells or hematopoietic progenitor cells are cultured in the medium including the polypeptides in accordance with the present invention, the hematopoietic stem cells or the hematopoietic progenitor cells that will be used may be one of these cell types alone or may be both of the cell types. In addition, the cells should include at least the hematopoietic stem cells or the hematopoietic progenitor cells, and may include other hematopoietic cells. Further, polypeptides of the invention can be used for hematopoietic stem or progenitor expansion of purified hematopoietic stem cell fraction or progenitor cell fractions from the cell populations that contain the hematopoietic stem cells or progenitor cells.

Examples of sources of hematopoietic stem cells and hematopoietic progenitor cells in the methods in accordance with the present invention are fetal liver, bone marrow, fetal bone marrow, peripheral blood, peripheral blood from persons from whom stem cells are mobilized by cytokines and/or dosing of antitumor drugs, cord blood, and the like of mammals such as human and mouse and the like. Any sources may be used as long as the tissue includes the hematopoietic stem cells.

A culture method using petri dishes and flasks for culture may be employed to culture the hematopoietic stem cells or the hematopoietic progenitor cells. The cultivation of the hematopoietic stem cells and/or progenitor cells may be improved by mechanically controlling medium composition, pH, and the like, and employing a bioreactor capable of high density cultivation (Schwartz, *Proc. Natl. Acad. Sci. U.S.A.*, 88: 6760, 1991; Koller, M. R., *Bio/Technology*, 11: 358, 1993; Koller, M. R., *Blood*, 82: 378, 1993; Palsson, B. O., *Bio/Technology*, 11: 368, 1993).

Since SCR-1 can increase activities of stromal cells to support the hematopoietic stem cells under the conditions of co-culture of stromal cells and hematopoietic cells, the hematopoietic stem cells and/or progenitor cells can be efficiently expanded when whole bone marrow cells are cultured in the presence of SCR-1. This type of co-culture of the stromal cells and the hematopoietic cells can be performed simply after the collection of the bone marrow cells without complicated cell separation. Furthermore, one can perform co-culture with separate components such as hematopoietic stem cells, progenitor cells and stromal cells from collected bone marrow cells and combine the hematopoietic cells and stromal cells from different individuals. Furthermore, one can grow stromal cells and establish stromal cell culture prior to co-culture with the hematopoietic stem cells for the hematopoietic stem cells or progenitor cell expansion. At this time, one can utilize cell stimulating factors to promote growth and survival of stromal cells to establish stromal cell culture. Examples of cell stimulating factors includes growth factors which are typically a cytokine such as SCF (stem cell factor), IL-3 (interleukin-3), GM-CSF (granulocyte/macrophage colony-stimulating factor), IL-6 (interleukin-6), TPO (thrombopoietin), G-CSF (granulocyte colony-stimulating factor), TGF-b (transforming growth factor-b), MIP-1a (Davatelis, G., J. Exp. Med. 167: 1939, 1988); differentiation and proliferation control factors such as hematopoietic hormones such as EPO (erythropoietin), chemokine, Wnt gene product, and notch ligand; and development control factors.

In addition, the proliferation and the survival of hematopoietic stem cells or hematopoietic progenitor cells can be retained by culturing the hematopoietic stem and/or progenitor cells with recombinant SCR-1 alone or combination with the cell stimulating factors without stromal cells. Examples of the cell stimulating factors used in this case are above described cell stimulating factors and the like.

Medium used for culture is not specially restricted as long as the proliferation or the survival of the hematopoietic stem cells or the hematopoietic progenitor cells is not perturbed. Preferable media are, for example, MEM-α medium (GIBCO BRL), SF-02 medium (Sanko Junyaku), Opti-MEM medium (GIBCO BRL), IMDM medium (GIBCO BRL), and PRMI1640 medium (GIBCO BRL). A culture temperature is usually ranging from 25 to 39° C., and preferably ranging from 33 to 39° C. Examples of additives to the medium are fetal bovine serum, human serum, horse serum, insulin, transferrin, lactoferrin, ethanolamine, sodium selenite, monothiolglycerol, 2-mercaptoethanol, bovine serum albumin, sodium pyruvate, polyethylene glycol, a variety of vitamins, and a variety of amino acids. A concentration of $CO_2$ is usually ranging from four to six percent, and preferably five percent.

Since hematopoietic stem cells can differentiate into all hematopoietic cell lineages, hematopoietic stem cells can be manipulated to be differentiated into a specific cell type in vitro, and then the specific cells can be transplanted. For example, when erythrocytes are necessary, after cultivation and expansion of the patient's stem cells, hemopoietic cells whose main component is the erythrocyte can be artificially produced using an erythrocyte differentiation induction or promoting factors such as EPO.

The hematopoietic stem cells or the hematopoietic progenitor cells cultured using the polypeptides in accordance with the present invention can replace as a graft for the conventional bone marrow transplantation or cord blood transplantation. Transplantation of the hematopoietic stem cells is superior to the conventional hematopoietic cell transplantation therapy, since the graft can take semipermanently.

The transplantation of the hematopoietic stem cells can be employed as therapy for a variety of diseases in addition to as combination therapy for total body X-ray irradiation therapy or advanced chemotherapy for leukemia. For example, when therapy accompanied with myelosuppression as an adverse reaction such as chemotherapy, radiation therapy, and the like is performed for the patient with solid cancer, hematological disorder, hematological failure can be early improved as follows. The bone marrow is collected before the therapy and the hematopoietic stem cells or the hematopoietic progenitor cells are allowed to expand in vitro. Then, the expanded cells are infused to the patient after the therapy, so that the patient can get benefit of early recovery and stronger chemotherapy than the conventional one can be performed to improve the therapeutic effect of the chemotherapy. In addition, the hematopoietic stem cells or the hematopoietic progenitor cells obtained according to the present invention are differentiated into a variety of hematopoietic cells. The transplantation of these cells into a patient with hypoplasia of a given hematopoietic cells can improve the patient's deficient status. In addition, this therapy can improve dyshemopoietic anemia to develop anemia such as aplastic anemia caused by bone marrow hypoplasia. Furthermore, examples of diseases in which the transplantation of the hematopoietic stem cells according to the present invention is effective are immunodeficiency syndrome such as chronic granulomatous disease, duplicated immunodeficiency syndrome, agammaglobulinemia, Wiskott-Aldrich syndrome, acquired immunodeficiency syndrome (AIDS), and the like, thalassemia, hemolytic anemia due to enzyme defect, congenital anemia such as sicklemia, Gaucher's disease, lysosomal storage disease such as mucopolysaccharidosis, adrenal white matter degeneration, a variety of cancers and tumors, and the like.

Transplantation of hematopoietic stem cells may be performed in the same manner as conventional bone marrow transplantation or cord blood transplantation other than the differences of the cells used.

The hematopoietic stem cells which may be used for the above described hematopoietic stem cell transplantation are derived from not only bone marrow but also the above described fetal liver, fetal bone marrow, peripheral blood, peripheral blood with stem cells induced by cytokines and/or dosing of antitumor drugs, cord blood, and the like.

The graft may be a composition including buffer solution and the like in addition to the hematopoietic stem cells and the hematopoietic progenitor cells produced by the method according to the present invention.

The hematopoietic stem cells or the hematopoietic progenitor cells produced according to the present invention may be used for ex vivo gene therapy. Since the incidence of recombination of target genes to the chromosome is low due to dormancy of the stem cells, differentiation of stem cells during the culture period, and the like, gene therapy to the hematopoietic stem cells has been hard to established. However, the present invention can amplify stem cells without differentiation, so that efficacy of gene transfer is expected to be remarkably improved. In gene therapy, a foreign gene (a gene for therapy) is transferred into the hematopoietic stem cells or the hematopoietic progenitor cells, and then the obtained gene-transferred cells are used. The foreign gene to be transferred is appropriately selected according to disease. Examples of diseases in which the target cells of gene therapy is the hematopoietic cells include immunodeficiency syndrome such as chronic granulomatous disease, duplicated immunodeficiency syndrome, agammaglobulinemia, Wiskott-Aldrich syndrome, acquired immunodeficiency syndrome (AIDS), and the like, thalassemia, hemolytic anemia due to enzyme defect, congenital anemia such as sicklemia, Gaucher's disease, lysosomal storage disease such as mucopolysaccharidosis, adrenal white matter degeneration, a variety of cancers and tumors, and the like.

Usual method used for transfer of a gene into animal cells is employed for the transfer of the gene for the therapy into hematopoietic stem cells or hematopoietic progenitor cells. Examples are a method using a vector for animal cells derived from virus utilized for gene therapy such as retrovirus vector such as Moloney mouse leukemia virus, adenovirus vector, adeno-associated virus (AAV) vector, herpes simplex virus vector, and HIV vector (with respect to a vector for gene therapy, see Verma, I. M., Nature, 389: 239, 1997); calcium phosphate transfection, DEAE-dextran transfection, electroporation, liposome method, lipofection method, microinjection method, and the like. Among them, methods using retrovirus vector, adeno-associated virus vector, or HIV vector are preferable, since expression of a gene is permanently expected due to insertion into the chromosome DNA of a target cell.

For example, adeno-associated virus (AAV) vector can be prepared as follows. First, a vector plasmid inserted a gene for therapy into ITR (inverted terminal repeat) at both ends of wild-type adeno-associated virus DNA and a helper plasmid for supplementing virus protein are transfected into 293 cell strain. Next, adenovirus as helper virus is infected, so that virus particles including the AAV vector are produced. Alternatively, instead of adenovirus, a plasmid which expresses adenovirus gene coding helper function may be transfected. The obtained virus particles are infected to the hematopoietic stem cells or the hematopoietic progenitor cells. Preferably, appropriate promoter and enhancer are inserted into upstream region of the target gene in the vector DNA, so that the expression of the gene is regulated. When marker gene such as a drug resistant gene is used in addition to the gene for therapy, cells transferred with the gene for therapy are easily selected. The gene for therapy may be sense gene or antisense gene.

A composition for gene therapy may include buffer solution and a novel active ingredient and the like in addition to the hematopoietic stem cells or the hematopoietic progenitor cells by the method according to the present invention.

A vector for gene therapy can be produced by transferring SCR-1 in expression vector using a usual method. This vector for gene therapy is useful to treat diseases which need survival and proliferation of the human hematopoietic stem cells. That is, a vector producing SCR-1 is transferred into the hematopoietic stem cells and the cells are cultured in vitro, so that the hematopoietic stem cells or the hematopoietic progenitor cells can proliferate dominatingly. The hematopoietic stem cells can proliferate in vivo caused by returning these hematopoietic stem cells thus treated. The hematopoietic stem cells can significantly proliferate in vivo by introducing this vector for gene therapy into the body. Alternatively, the bone marrow cells derived from a patient are cultured and transferred with this vector for gene therapy, so that the hematopoietic stem cells or the hematopoietic progenitor cells can be proliferated in culture system. Alternatively, this vector for gene therapy is transferred into stromal cell derived from bone marrow and cultivated and mesenchaymal stem cell, so that the activity to support hematopoietic stem cells can be added or increased.

As shown in Examples, since it is possible that the stromal cells without the activity to support the hematopoietic stem cells can be modified to include this activity using SCR-1, stromal cells derived from human or mouse can have the activity to support the hematopoietic stem cells by gene transferring SCR-1. The stromal cells expressing SCR-1 and hematopoietic stem cells or hematopoietic progenitor cells are co-cultured, so that the hematopoietic stem cells or the hematopoietic progenitor cells can exist and proliferate so as to be useful for a variety treatment.

Since the hematopoietic stem cells or the hematopoietic progenitor cells can survive and proliferate by expression of SCR-1 in the stromal cell, an activity to support the hematopoietic stem cells of the stromal cells can be assessed using the expression of SCR-1 as an index. The expression of SCR-1 in the stromal cells can be confirmed using antibody to SCR-1. PCR primers can be prepared from genes included in SEQ ID NO: 31, SEQ ID NO: 33 or other polynucleotides of the invention and RNA is prepared from the stromal cells of interest, and RT-PCR is performed, so that the expression of SCR-1 can be confirmed. Antibody to SCR-1 will be described below.

The pharmaceutical composition in accordance with the present invention can be administered to human. The pharmaceutical composition having an activity to proliferate or to support the human hematopoietic stem cells or the hematopoietic progenitor cells can be produced by mixing medically acceptable diluent, stabilizer, carrier, and/or other additives with the polypeptides in accordance with the present invention. At this time, in order to increase the stability of the protein in vivo the polypeptides in accordance with the present invention may be modified by a modifying agent. Examples of the modifying agent are polyethylene glycol (PEG), dextran, poly(N-vinylpyrrolidone), polypropylene glycol homopolymer, polypropylene oxide/ethylene oxide copolymer, polyoxyethylated polyol, polyvinyl alcohol, and the like. Examples of modification of protein with PEG are a method in which activated ester derivatives of PEG is reacted with the protein, a method in which aldehyde derivatives at end portion of PEG is reacted with protein under the presence of a reducing agent, and the like. Japanese Unexamined Patent Application No. 10-510980 discloses modification of such protein in detail.

When the pharmaceutical composition in accordance with the present invention is administered to human, recovery from hematological suppression due to an adverse drug reaction of carcinostatics; early recovery of hematopoietic cells at bone marrow transplantation, peripheral blood stem cell transplantation, or cord blood transplantation; and recovery of hematopoietic function at pancytopenia such as aplastic anemia (AA) and myelodysplastic syndrome (MDS) are expected.

The antibody in accordance with the present invention reacts specifically to the above described polypeptides in accordance with the present invention. This antibody may be monoclonal antibodies or polyclonal antibodies as long as they react specifically to the above described polypeptides.

The antibody in accordance with the present invention can be prepared according to usual methods. For example, the antibody can be prepared either in vivo method in which animals are additionally immunized by antigen together with adjuvant once or several times at an interval of several weeks or in vitro method in which immune cells are isolated and sensitized in an appropriate culture system. Examples of immune cells which can produce the antibody in accordance with the present invention are splenic cells, tonsillar cells, lymph gland cells, and the like.

The whole polypeptide according to the present invention is not necessarily used as an antigen. A part of a polypeptide of the invention may be used as an antigen. When the antigen is a short peptide, particularly, a peptide made of about 20 amino acid residues, it may be used by binding it to a carrier protein having high antigenicity such as keyhole lympet hemocyanin or bovine serum albumin using chemical modification and the like. Alternatively, the antigen may be used by covalently binding it to a peptide having branching skeleton such as lysine core MAP peptide instead of the carrier protein (Posnett et al., *J. Biol. Chem.*, 263, 1719–1725, 1988; Lu et al., *Mol. Immunol.*, 28, 623–630, 1991; Briand et al., *J. Immunol. Methods*, 156, 255–265, 1992).

Examples of adjuvants are Freund's complete adjuvant, Freund's incomplete adjuvant, aluminum hydroxide gel, and the like. Animals given the antigen are, for example, mouse, rat, rabbit, sheep, goat, chicken, bovine, horse, guinea pig, hamster, and the like. The blood is collected from these animals and the serum is separated. Then, immunoglobulin is purified from the serum using an ammonium sulfate precipitation method, anion exchange chromatography, protein A chromatography, or protein G chromatography to obtain polyclonal antibodies.

With respect to chicken, antibodies can be purified from an egg. Monoclonal antibodies can be purified and prepared from supernatant of culture of hybridoma cells or ascites from animals which received intrapertoneal administration of hybridoma cells. Hybridomas are made by fusion of the immune cells sensitized in vitro, or immune cells from the above described animals with parent cells capable of cultivation. Examples of parent cells are X63, NS-1, P3U1, X63.653, SP2/O, Y3, SKO-007, GM1500, UC729-6, HM2.0, NP4-1 cell strains, and the like. Preparation may be performed by cultivating the immortalized antibody-forming cells obtained by sensitization in vitro, or infection of a proper virus such as EB virus to the immune cells of the above described animals.

In addition to these cell engineering methods, antibodies can be obtained using gene engineering methods. For example, the antibody gene obtained from the in vitro sensitized cells or immune cells derived from the above described animals is amplified by PCR (polymerase chain reaction) and isolated, and the amplified genes are transferred into microorganisms such as *E. coli* to produce the antibodies. Alternatively, the antibodies may be expressed on surfaces of phages as fused protein. Antibodies of the invention are also addressed herein, infra.

SCR-1 can be measured in vivo using antibodies in accordance with the present invention. Thus, the relationship between SCR-1 and pathological status of a variety of diseases can be clarified. Moreover, the antibodies can be used for diagnosis and treatment of diseases, and efficient affinity purification of SCR-1.

The present invention provides polypeptides having an activity to support survival or proliferation of hematopoietic stem cells or hematopoietic progenitor cells by effecting or acting thereon, or an activity to give an activity to support the hematopoietic stem cells to stromal cells by effecting thereon, and also provides DNA coding thereof. The polypeptides in accordance with the present invention can efficiently maintain the proliferation or the survival of the hematopoietic stem cells or the hematopoietic progenitor cells.

In addition, the polypeptides in accordance with the present invention can be used as a medicine to proliferate or to support human hermatopoietic stem cells or human hematopoietic progenitor cells.

Alternatively, the invention is described as set out below.

5.2 Nucleic Acids and Polypeptides of the Invention

Nucleotide and amino acid sequences of the invention are set forth as SEQ ID NO: 1–24, and 31–34. Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein-IgM fusion would generate a decavalent form of the protein of the invention.

The present invention also provides both full-length and mature forms (for example, without a signal sequence or precursor sequence) of the disclosed proteins. The protein coding sequence is identified in the sequence listing by translation of the disclosed nucleotide sequences. The mature form of such protein may be obtained by expression of a full-length polynucleotide in a suitable mammalian cell or other host cell. The sequence of the mature form of the protein is also determinable from the amino acid sequence of the full-length form. Where proteins of the present invention are membrane bound, soluble forms of the proteins are also provided. In such forms, part or all of the regions causing the proteins to be membrane bound are deleted so that the proteins are fully secreted from the cell in which it is expressed.

The polynucleotides of the invention include naturally occurring or wholly or partially synthetic DNA, e.g., cDNA and genomic DNA, and RNA, e.g., mRNA. SEQ ID NO: 1–9, 11, 12, 31 or 33 may include the entire coding region of the cDNA or may represent a portion of the coding region of the cDNA. Further 5' and 3' sequence can be obtained using methods known in the art. For example, full length cDNA or genomic DNA that corresponds to any of the polynucleotides of the SEQ ID NO: 1–9, 11, 12, 31 or 33 can be obtained by screening appropriate cDNA or genomic DNA libraries under suitable hybridization conditions using any of the polynucleotides of the SEQ ID NO: 1–9, 11, 12, 31 or 33 or a portion thereof as a probe. Alternatively, the polynucleotides of the SEQ ID NO: 1–9, 11, 12, 31 or 33 may be used as the basis for suitable primer(s) that allow identification and/or amplification of genes in appropriate genomic DNA or cDNA libraries.

The nucleic acid sequences of the invention can be assembled ESTs and sequences (including cDNA and genomic sequences) obtained from one or more public databases, such as dbEST, gbpri, and UniGene. The sequences falling within the scope of the present invention are not limited to these specific sequences, but also include allelic and species variations thereof. Allelic and species variations can be routinely determined by comparing the sequence provided in SEQ ID NO: 8–9, 11–12, 31 or 33 a representative fragment thereof, or a nucleotide sequence at least 90% identical, preferably 99.9% identical, to SEQ ID NO: 8–9, 11–12, 31 or 33 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated.

The nucleic acids of the present invention, designated as SEQ ID NO. 8 and 9 were assembled using an EST sequence as a seed. The EST sequence can be extended into a full-length nucleic acid sequence by programs or algorithms known in the art. Preferably, a recursive algorithm is used to extend the seed EST into an extended assemblage, by pulling additional sequences from different databases (e.g., Hyseq's database containing EST sequences, dbEST version 114, gb pri 114, and UniGene version 101) that belong to this assemblage. The algorithm terminates when there was no additional sequences from the databases that will extend the assemblage. Further, the inclusion of component sequences into the assemblage is preferably based on a BLASTN hit to the extending assemblage with BLAST score greater than 300 and percent identity greater than 95%. BLAST, which stands for Basic Local Alignment Search Tool, is used to search for local sequence alignments (Altschul, S. F., J. Mol. Evol. 36: 290–300 (1993) and Altschul S. F. et al., J. Mol. Biol. 21: 403–10 (1990)). BLAST produces alignments of both nucleotide and amino acid sequences to determine sequence similarity. Because of the local nature of the alignments, BLAST is especially useful in determining exact matches.

The EST sequences (SEQ ID NO. 1–7) can provide identifying sequence information, representative fragment or segment information, or novel segment information for the full-length gene.

The nearest neighbor result for the nucleic acids of the present invention, including SEQ ID NO. 9, can be obtained by searching a database using an algorithm or a program. Preferably, a FASTA version 3 search against Genpept, using Fastxy algorithm. The nearest neighbor result shows the closest homologue for each assemblage from Genpept (and contains the translated amino acid sequences for which the assemblage encodes).

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

Species homologs (or orthologs) of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or related to that encoded by the polynucleotides.

5.3 Nucleic Acids of the Invention

The isolated polynucleotides of the invention include, but are not limited to, a polynucleotide encoding a polypeptide comprising SEQ ID NO: 10, 13–24, 32 and 34, or the mature protein portion thereof. Preferred nucleic acid sequences are set forth as SEQ ID NO: 9, 11, 12, 31 or 33.

The isolated polynucleotides of the invention further include, but are not limited to a polynucleotide comprising any of the nucleotide sequence of the SEQ ID NO: 1–9, 11, 12, 31 or 33; a polynucleotide comprising the full length protein coding sequence of the polynucleotides of the SEQ ID NO: 1–9, 11, 12, 31 or 33; and a polynucleotide comprising the nucleotide sequence encoding the mature protein coding sequence of the polynucleotides of the SEQ ID NO: 1–9, 11, 12, 31 or 33. The polynucleotides of the present invention also include, but are not limited to, a polynucleotide that preferably has stem cell growth factor activity and that hybridizes under stringent conditions (a) to the complement of any of the nucleotides sequences of the SEQ ID NO: 1–9, 11, 12, 31 or 33 (b) to a polynucleotide encoding the polypeptide of SEQ ID NO: 10, 13–24, 32 or 34, a polynucleotide which is an allelic variant of any polynucleotide recited above; a polynucleotide which encodes a species homolog of any of the proteins recited above; or a polynucleotide that encodes a polypeptide comprising a specific domain or truncation of the polypeptide of SEQ ID NO: 10, 13–24, 32 or 34. Domains of interest may depend on the nature of the encoded polypeptide; e.g., domains in receptor-like polypeptides include ligand-binding, extracellular, transmembrane, or cytoplasmic domains, or combinations thereof; domains in immunoglobulin-like proteins include the variable immunoglobulin-like domains; domains in enzyme-like polypeptides include catalytic and substrate binding domains; and domains in ligand polypeptides include receptor-binding domains.

Polynucleotides encoding preferred polypeptide truncations of the invention can be used to generate polynucleotides encoding chimeric or fusion proteins comprising one or more domains of the invention and heterologous protein sequences.

The polynucleotides of the invention additionally include the complement of any of the polynucleotides recited above.

The polynucleotides of the invention also provide polynucleotides including nucleotide sequences that are substantially equivalent to the polynucleotides recited above. Polynucleotides according to the invention can have, e.g., at least about 65%, at least about 70%, at least about 75%, at least about 80%, 81%, 82%, 83%, 84%, more typically at least about 85%, 86%, 87%, 88%, 89%, more typically at least about 90%, 91%, 92%, 93%, 94%, and even more typically at least about 95%, 96%, 97%, 98%, 99% sequence identity to a polynucleotide recited above. The invention also provides the complement of such polynucleotides. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polynucleotides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The sequences falling within the scope of the present invention are not limited to the specific sequences herein described, but also include allelic variations thereof. Allelic variations can be routinely determined by comparing the nucleotide sequences provided in the SEQ ID NO: 1–9, 11, 12, 31 or 33, a representative fragment thereof, or a nucleotide sequence at least 99.9% identical to any of the nucleotide sequences of the SEQ ID NO: 1–9, 11, 12, 31 or 33 with a sequence from another isolate of the same species. To accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated. Any specific sequence disclosed herein can be readily screened for errors by resequencing a particular fragment, such as an ORF, in both directions (i.e., sequence both strands).

The present invention further provides recombinant constructs comprising a nucleic acid having any of the nucleotide sequences of the SEQ ID NO: 1–9, 11, 12, 31 or 33 or a fragment thereof or any other polynucleotides of the invention. In one embodiment, the recombinant constructs of the present invention comprise a vector, such as a plasmid or viral vector, into which a nucleic acid having any of the nucleotide sequences of the SEQ ID NO: 1–9, 11, 12, 31 or 33 or a fragment thereof is inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, PSVL (Pharmacia).

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda PR, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an amino terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotech, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Included within the scope of the nucleic acid sequences of the invention are nucleic acid sequence fragments that hybridize under stringent conditions to any of the nucleotide sequences of the SEQ ID NO: 1–9, 11, 12, 31 or 33 or complements thereof, which fragment is greater than about 10 bp, preferably 20 to 50 bp, and even greater than 100 bp, greater than 300 bp, or greater than 500 bp. Fragments of, e.g. 15, 16, or 20 bp or more that are selective for (i.e. specifically hybridize to any one of the polynucleotides of the invention) are contemplated. Probes capable of specifically hybridizing to a polynucleotide can differentiate polynucleotide sequences of the invention from other polynucleotide sequences in the same family of genes or can differentiate human genes from genes of other species, and are preferably based on unique nucleotide sequences.

In accordance with the invention, polynucleotide sequences comprising the mature protein coding sequences corresponding to the SEQ ID NO: 10, 13–24, 32 or 34 or functional equivalents thereof, may be used to generate recombinant DNA molecules that direct the expression of that nucleic acid, or a functional equivalent thereof, in appropriate host cells. Also included are the cDNA inserts of any of the clones identified herein.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. Nucleic acids encoding the amino acid sequence variants are preferably constructed by mutating the polynucleotide to encode an amino acid sequence that does not occur in nature. These nucleic acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells and sequences such as FLAG or poly-histidine sequences useful for purifying the expressed protein.

In a preferred method, polynucleotides encoding the novel amino acid sequences are changed via site-directed mutagenesis. This method uses oligonucleotide sequences to alter a polynucleotide to encode the desired amino acid variant, as well as a sufficient adjacent nucleotides on both sides of the changed amino acid to form a stable duplex on either side of the site of being changed. In general, the techniques of site-directed mutagenesis are well known to those of skill in the art and this technique is exemplified by publications such as, Edelman et al., DNA 2:183 (1983). A versatile and efficient method for producing site-specific changes in a polynucleotide sequence was published by Zoller and Smith, Nucleic Acids Res. 10:6487–6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives a polynucleotide encoding the desired amino acid variant.

A further technique for generating amino acid variants is the cassette mutagenesis technique described in Wells et al., Gene 34:315 (1985); and other mutagenesis techniques well known in the art, such as, for example, the techniques in Sambrook et al., supra, and Current Protocols in Molecular Biology, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Polynucleotides of the invention can also be used to induce immune responses. For example, as described in Fan et al., Nat. Biotech. 17:870–872 (1999), incorporated herein by reference, nucleic acid sequences encoding a polypeptide may be used to generate antibodies against the encoded polypeptide following topical administration of naked plasmid DNA or following injection, and preferably intramuscular injection of the DNA. The nucleic acid sequences are preferably inserted in a recombinant expression vector and may be in the form of naked DNA.

5.3.1 Antisense Nucleic Acids

Another aspect of the invention pertains to isolated antisense nucleic acid molecules that can hybridize to, or are complementary to, the nucleic acid molecule comprising the stem cell growth factor-like nucleotide sequence, or fragments, analogs or derivatives thereof. An "antisense" nucleic acid comprises a nucleotide sequence that is complementary to a "sense" nucleic acid encoding a protein (e.g., complementary to the coding strand of a double-stranded cDNA molecule or complementary to an mRNA sequence). In specific aspects, antisense nucleic acid molecules are provided that comprise a sequence complementary to at least about 10, 25, 50, 100, 250 or 500 nucleotides or an entire stem cell growth factor-like coding strand, or to only a portion thereof. Nucleic acid molecules encoding fragments, homologs, derivatives, and analogs of a stem cell growth factor-like or antisense nucleic acids complementary to a stem cell growth factor-like nucleic acid sequence of are additionally provided.

In one embodiment, an antisense nucleic acid molecule is antisense to a "coding region" of the coding strand of a nucleotide sequence encoding a stem cell growth factor-like protein. The term "coding region" refers to the region of the nucleotide sequence comprising codons which are translated into amino acid residues. In another embodiment, the antisense nucleic acid molecule is antisense to a "conceding region" of the coding strand of a nucleotide sequence encoding the stem cell growth factor-like protein. The term "conceding region" refers to 5' and 3' sequences which flank the coding region that are not translated into amino acids (i.e., also referred to as 5' and 3' untranslated regions).

Given the coding strand sequences encoding the stem cell growth factor-like protein disclosed herein, antisense nucleic acids of the invention can be designed according to the rules of Watson and Crick or Hoogsteen base pairing. The antisense nucleic acid molecule can be complementary to the entire coding region of stem cell growth factor-like mRNA, but more preferably is an oligonucleotide that is antisense to only a portion of the coding or noncoding region of stem cell growth factor-like mRNA. For example, the antisense oligonucleotide can be complementary to the region surrounding the translation start site of stem cell growth factor-like mRNA. An antisense oligonucleotide can be, for example, about 5, 10, 15, 20, 25, 30, 35, 40, 45, or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, bypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following section).

The antisense nucleic acid molecules of the invention are typically administered to a subject or generated in situ such that they hybridize with or bind to cellular mRNA and/or genomic DNA encoding a stem cell growth factor-like protein thereby inhibit expression of the protein (e.g., by inhibiting transcription and translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual alpha-units, the strands run parallel to each other. See, e.g., Gaultier, et al., 1987. Nucl. Acids Res. 15, 6625–6641. The antisense nucleic acid molecule can also comprise a 2'-o-methylribonucleotide (see, e.g., Inoue, et al. 1987. Nucl. Acids Res. 15, 6131–6148) or a chimeric RNA-DNA analogue (see, e.g., Inoue, et al., 1987. FEBS Lett. 215, 327–330).

5.3.2 Ribozymes and PNA Moieties

Nucleic acid modifications include, by way of non-limiting example, modified bases, and nucleic acids whose sugar phosphate backbones are modified or derivatized. These modifications are carried out at least in part to enhance the chemical stability of the modified nucleic acid, such that they can be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haseloff and Gerlach 1988. Nature 334, 585–591) can be used to catalytically cleave stem cell growth factor-like mRNA transcripts to thereby inhibit translation of stem cell growth factor-like mRNA. A ribozyme having specificity for a stem cell growth factor-like-encoding nucleic acid can be designed based upon the nucleotide sequence of a stem cell growth factor-like cDNA disclosed herein. For example, a derivative of a Tetrahymena L-19 IVS RNA can be constructed in which the nucleotide sequence of the active site is complementary to the nucleotide sequence to be cleaved in a stem cell growth factor-like-encoding mRNA. See, e.g., U.S. Pat. No. 4,987,071 to Cech, et al. and U.S. Pat. No. 5,116,742 to Cech, et al. Stem cell growth factor-like mRNA can also be used to select a catalytic RNA having a specific ribonuclease activity from a pool of RNA molecules. See, e.g., Bartel et al., (1993) Science 261, 1411–1418.

Alternatively, stem cell growth factor-like gene expression can be inhibited by targeting nucleotide sequences complementary to the regulatory region of the stem cell growth factor-like nucleic acid (e.g., the stem cell growth factor-like promoter and/or enhancers) to form triple helical structures that prevent transcription of the stem cell growth factor-like gene in target cells. See, e.g., Helene, 1991. Anticancer Drug Des. 6, 569–84; Helene, et al. 1992. Ann. N.Y. Acad. Sci. 660, 27–36; Maher, 1992. Bioassays 14, 807–15.

In various embodiments, the stem cell growth factor-like nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. See, e.g., Hyrup, et al., 1996. Bioorg Med Chem 4, 5–23. As used herein, the terms "peptide nucleic acids" or "PNAs" refer to nucleic acid mimics (e.g., DNA mimics) in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, et al., 1996. supra; Perry-O'Keefe, et al., 1996. Proc. Natl. Acad. Sci. USA 93, 14670–14675.

PNAs of stem cell growth factor-like can be used in therapeutic and diagnostic applications. For example, PNAs can be used as antisense or antigene agents for sequence-specific modulation of gene expression by, e.g., inducing transcription or translation arrest or inhibiting replication. PNAs of stem cell growth factor-like can also be used, for example, in the analysis of single base pair mutations in a gene (e.g., PNA directed PCR clamping; as artificial restriction enzymes when used in combination with other enzymes, e.g., S1 nucleases (see, Hyrup, et al., 1996.supra); or as probes or primers for DNA sequence and hybridization (see, Hyrup, et al., 1996, supra; Perry-O'Keefe, et al., 1996. supra).

In another embodiment, PNAs of stem cell growth factor-like can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of stem cell growth factor-like can be generated that may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (see, Hyrup, et al., 1996. supra). The synthesis of PNA-DNA chimeras can be performed as described in Hyrup, et al., 1996. supra and Finn, et al., 1996. Nucl Acids Res 24, 3357–3363. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA. See, e.g., Mag, et al., 1989. Nucl Acid Res 17, 5973–5988. PNA monomers are then coupled in a stepwise manner to produce a chimeric molecule with a 5' PNA segment and a 3' DNA segment. See, e.g., Finn, et al., 1996. supra. Alternatively, chimeric molecules can be synthesized with a 5' DNA segment and a 3' PNA segment. See, e.g., Petersen, et al., 1975. Bioorg. Med. Chem. Lett. 5, 1119–11124.

In other embodiments, the oligonucleotide may include other appended groups such as peptides (e.g., for targeting host cell receptors in vivo), or agents facilitating transport across the cell membrane (see, e.g., Letsinger, et al., 1989. Proc. Natl. Acad. Sci. U.S.A. 86, 6553–6556; Lemaitre, et al., 1987. Proc. Natl. Acad. Sci. 84, 648–652; PCT Publication No. WO88/09810) or the blood-brain barrier (see, e.g., PCT Publication No. WO89/10134). In addition, oligonucleotides can be modified with hybridization-triggered cleavage agents (see, e.g., Krol, et al., 1988. BioTechniques 6,958–976) or intercalating agents (see, e.g., Zon, 1988. Pharm. Res. 5, 539–549). To this end, the oligonucleotide can be conjugated to another molecule, e.g., a peptide, a hybridization triggered cross-linking agent, a transport agent, a hybridization-triggered cleavage agent, and the like.

5.4 Hosts

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

Knowledge of stem cell growth factor-like DNA sequences allows for modification of cells to permit, or increase, expression of stem cell growth factor-like polypeptide. Cells can be modified (e.g., by homologous recombination) to provide increased stem cell growth factor-like polypeptide expression by replacing, in whole or in part, the naturally occurring stem cell growth factor-like promoter with all or part of a heterologous promoter so that the cells stem cell growth factor-like polypeptide is expressed at higher levels. The heterologous promoter is inserted in such a manner that it is operatively linked to stem cell growth factor-like encoding sequences. See, for example, PCT International Publication No. WO94/12650, PCT International Publication No. WO92/20808, and PCT International Publication No. WO91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the stem cell growth factor-like coding sequence, amplification of the marker DNA by standard selection methods results in co-amplification of the stem cell growth factor-like coding sequences in the cells.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., Basic Methods in Molecular Biology (1986)). The host cells containing one of polynucleotides of the invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as *E. coli* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell tines. Mammalian expression vectors will comprise an origin of replication, a suitable promoter, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, and regulatory protein binding sites or combinations of said sequences. Alternatively, sequences which affect the structure or stability of the RNA or protein produced may be replaced, removed, added, or otherwise modified by targeting, including polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

5.5 Polypeptides of the Invention

The isolated polypeptides of the invention include, but are not limited to, a polypeptide comprising: the amino acid sequence set forth as SEQ ID NO: 10, 13–24, 32 or 34 or an amino acid sequence encoded by any one of the nucleotide sequences SEQ ID NO: 1–9, 11, 12, 31 or 33 or the corresponding full length or mature protein. Polypeptides of the invention also include polypeptides preferably with biological or immunological activity that are encoded by: (a) a polynucleotide having any one of the nucleotide sequences set forth in the SEQ ID NO: 1–9, 11, 12, 31 or 33 or (b)

polynucleotides encoding the amino acid sequence set forth as SEQ ID NO: 10, 13–24, 32 or 34 or (c) polynucleotides that hybridize to the complement of the polynucleotides of either (a) or (b) under stringent hybridization conditions. The invention also provides biologically active or immunologically active variants of any of the polypeptide amino acid sequences set forth as SEQ ID NO: 10, 13–24, 32 or 32 or the corresponding full length or mature protein; and "substantial equivalents" thereof (e.g., with at least about 65%, at least about 70%, at least about 75%, at least about 80%, at least about 85%, 86%, 87%, 88%, 89%, at least about 90%, 91%, 92%, 93%, 94%, typically at least about 95%, 96%, 97%, more typically at least about 98%, or most typically at least about 99% amino acid identity) that retain biological activity. Polypeptides encoded by allelic variants may have a similar, increased, or decreased activity compared to polypeptides comprising SEQ ID NO: 10, 13–24, 32 or 34.

Protein compositions of the present invention may further comprise an acceptable carrier, such as a hydrophilic, e.g., pharmaceutically acceptable, carrier.

The invention also relates to methods for producing a polypeptide comprising growing a culture of host cells of the invention in a suitable culture medium, and purifying the protein from the cells or the culture in which the cells are grown. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, or from a lysate prepared from the host cells and further purified. Preferred embodiments include those in which the protein produced by such process is a full length or mature form of the protein.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins. A variety of methodologies known in the art can be utilized to obtain any one of the isolated polypeptides or proteins of the present invention. At the simplest level, the amino acid sequence can be synthesized using commercially available peptide synthesizers. This technique is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, Protein Purification: Principles and Practice, Springer-Verlag (1994); Sambrook, et al., in Molecular Cloning: A Laboratory Manual; Ausubel et al., Current Protocols in Molecular Biology. Polypeptide fragments that retain biological/immunological activity include fragments encoding greater than about 100 amino acids, or greater than about 200 amino acids, and fragments that encode specific protein domains.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The protein of the invention may also be expressed as a product of transgenic. animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein. Regions of the protein that are important for the protein function can be determined by various methods known in the art including the alanine-scanning method which involved systematic substitution of single or strings of amino acids with alanine, followed by testing the resulting alanine-containing variant for biological activity. This type of analysis determines the importance of the substituted amino acid(s) in biological activity.

Other fragments and derivatives of the sequences of proteins which would be expected to retain protein activity in whole or in part and are useful for screening or other immunological methodologies may also be easily made by those skilled in the art given the disclosures herein. Such modifications are encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat™ kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl™ or Cibacrom blue 3GA Sepharose™; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. The protein can also be tagged with an epitope and subsequently purified by using a specific antibody directed to such epitope. One such epitope ("FLAG®") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The polypeptides of the invention include analogs (variants). Analogs embrace fragments, as well as antagonists which comprise one or more amino acids deleted, inserted, or substituted. Analogs of the invention also embrace fusions of the polypeptide of the invention or modifications of the polypeptide of the invention or analog is fused to another moiety or moieties, e.g., targeting moiety, imaging moiety or another therapeutic agent. Such analogs may exhibit improved properties such as activity and/or stability. Examples of moieties which may be fused to polypeptides of the invention or analogs thereof include, for example, targeting moieties which provide for the delivery of polypeptide to desired cell types. Other moieties which may be fused to the polypeptides of the invention include therapeutic agents which are used for treatment of disorders described herein.

5.5.1 Determining Polypeptide and Polynucleotide Identity and Similarity

Preferred identity and/or similarity are designed to give the largest match between the sequences tested. Methods to determine identity and similarity are codified in computer programs including, but are not limited to, the GCG program package, including GAP (Devereux, J., et al., Nucleic Acids Research 12(1): 387 (1984); Genetics Computer Group, University of Wisconsin, Madison, Wis.), BLASTP, BLASTN, BLASTX, FASTA (Altschul, S. F. et al., J. Molec. Biol. 215:403–410 (1990), PSI-BLAST (Altschul S. F. et al., Nucleic Acids Res. vol. 25, pp. 3389–3402, herein incorporated by reference), the eMatrix software (Wu et al., J. Comp. Biol., vol. 6, pp. 219–235 (1999), herein incorporated by reference), eMotif software (Nevill-Manning et al, ISMB-97, vol 4, pp. 202–209, herein incorporated by reference), the GeneAtlas software (Molecular Simulations Inc. (MSI), San Diego, Calif.) (Sanchez and Sali (1998) Proc. Natl. Acad. Sci., 95, 13597–13602; Kitson D H et al, (2000) "Remote homology detection using structural modeling—an evaluation" Submitted; Fischer and Eisenberg (1996) Protein Sci. 5, 947–955), Neural Network SignalP V1.1 program (from Center for Biological Sequence Analysis, The Technical University of Denmark) and the Kyte-Doolittle hydrophobocity prediction algorithm (J. Mol Biol, 157, pp. 105–31 (1982), incorporated herein by reference). The BLAST programs are publicly available from the National Center for Biotechnology Information (NCBI) and other sources (BLAST Manual, Altschul, S., et al. NCB NLM NIH Bethesda, Md. 20894; Altschul, S., et al., J. Mol. Biol. 215:403–410 (1990).

5.6 Chimeric and Fusion Proteins

The invention also provides stem cell growth factor-like chimeric or fusion proteins. As used herein, a stem cell growth factor-like "chimeric protein" or "fusion protein" comprises a stem cell growth factor-like polypeptide operatively linked to either a different stem cell growth factor-like polypeptide or a non-stem cell growth factor-like polypeptide. An "stem cell growth factor-like polypeptide" refers to a polypeptide having an amino acid sequence corresponding to a stem cell growth factor-like protein, whereas a "non-stem cell growth factor-like polypeptide" refers to a polypeptide having an amino acid sequence corresponding to a protein that is not substantially homologous to the stem cell growth factor-like protein, e.g., a protein that is different from the stem cell growth factor-like protein and that is derived from the same or a different organism. Within a stem cell growth factor-like fusion protein the stem cell growth factor-like polypeptide can correspond to all or a portion of a stem cell growth factor-like protein. In one embodiment, a stem cell growth factor-like fusion protein comprises at least one biologically active portion of a stem cell growth factor-like protein. In another embodiment, a stem cell growth factor-like fusion protein comprises at least two biologically active portions of a stem cell growth factor-like protein. In yet another embodiment, a stem cell growth factor-like fusion protein comprises at least three biologically active portions of a stem cell growth factor-like protein. Within the fusion protein, the term "operatively-linked" is intended to indicate that the stem cell growth factor-like polypeptide(s) and/or the non-stem cell growth factor-like polypeptide are fused in-frame with one another. The non-stem cell growth factor-like polypeptide can be fused to the N-terminus or C-terminus of the stem cell growth factor-like polypeptide.

In one embodiment, the fusion protein is a GST-stem cell growth factor-like fusion protein in which the stem cell growth factor-like sequences are fused to the C-terminus of the GST (glutathione S-transferase) sequences. Such fusion proteins can facilitate the purification of recombinant stem cell growth factor-like polypeptides.

In another embodiment, the fusion protein is a stem cell growth factor-like protein containing a heterologous signal sequence at its N-terminus. In certain host cells (e.g., mammalian host cells), expression and/or secretion of stem cell growth factor-like can be increased through use of a heterologous signal sequence.

In yet another embodiment, the fusion protein is a stem cell growth factor-like-immunoglobulin fusion protein in which the stem cell growth factor-like sequences are fused to sequences derived from a member of the immunoglobulin protein family. The stem cell growth factor-like-immunoglobulin fusion proteins of the invention can be incorporated into pharmaceutical compositions and administered to a subject to inhibit an interaction between a stem cell growth factor-like ligand and a stem cell growth factor-like protein on the surface of a cell, to thereby suppress stem cell growth factor-like-mediated signal transduction in vivo. The stem cell growth factor-like-immunoglobulin fusion proteins can be used to affect the bioavailability of a stem cell growth factor-like cognate ligand. Inhibition of the stem cell growth factor-like ligand/stem cell growth factor-like interaction can be useful therapeutically for both the treatment of proliferative and differentiative disorders, as well as modulating (e.g. promoting or inhibiting) cell survival. Moreover, the stem cell growth factor-like-immunoglobulin fusion proteins of the invention can be used as immunogens to produce anti-stem cell growth factor-like antibodies in a subject, to purify stem cell growth factor-like ligands, and in screening assays to identify molecules that inhibit the interaction of stem cell growth factor-like with a stem cell growth factor-like ligand.

Stem cell growth factor-like chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) Current Protocols in Molecular Biology, John Wiley & Sons, 1992). Moreover, many expression vectors are commercially available that already encode a fusion moiety (e.g., a GST polypeptide). Stem cell growth factor-like-encoding nucleic acid can be cloned into such an expression vector such that the fusion moiety is linked in-frame to the stem cell growth factor-like protein.

5.7 Gene Therapy

Mutations in the polynucleotides of the invention gene may result in loss of normal function of the encoded protein. The invention thus provides gene therapy to restore normal activity of the polypeptides of the invention; or to treat disease states involving polypeptides of the invention. Delivery of a functional genes encoding polypeptides of the invention to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no. 6679, pp.25–20 (1998). For additional reviews of gene therapy technology see Friedmann, Science, 244: 1275–1281 (1989); Verma, Scientific American: 68–84 (1990); and Miller, Nature, 357: 455–460 (1992). Introduction of any one of the nucleotides of the present invention or a gene encoding the polypeptides of the present invention can also be accomplished with extrachromosomal substrates (transient expression) or artificial chromosomes (stable expression). Cells may also be cultured ex vivo in the presence of proteins of the present invention in order to proliferate or to produce a desired effect on or activity in such cells. Treated cells can then be introduced in vivo for therapeutic purposes. Alternatively, it is contemplated that in other human disease states, preventing the expression of or inhibiting the activity of polypeptides of the invention will be useful in treating the disease states. It is contemplated that antisense therapy or gene therapy could be applied to negatively regulate the expression of polypeptides of the invention.

Other methods inhibiting expression of a protein include the introduction of antisense molecules to the nucleic acids of the present invention, their complements, or their translated RNA sequences, by methods known in the art, the removal of the nucleic acids of the present invention such as using targeted deletion methods, or the insertion of a negative regulatory element such as a silencer, which is tissue specific. Further, the polypeptides of the present invention can be inhibited by the introduction of antisense molecules that hybridize to nucleic acids that encode for the polypeptides of the present invention and by the removal of a gene that encode for the polypeptides of the present invention.

The present invention still further provides cells genetically engineered in vivo to express the polynucleotides of the invention, wherein such polynucleotides are in operative association with a regulatory sequence heterologous to the host cell which drives expression of the polynucleotides in the cell. These methods can be used to increase or decrease the expression of the polynucleotides of the present invention.

Knowledge of DNA sequences provided by the invention allows for modification of cells to permit, increase, or decrease, expression of endogenous polypeptide. Cells can be modified (e.g., by homologous recombination) to provide increased polypeptide expression by replacing, in whole or in part, the naturally occurring promoter with all or part of a heterologous promoter so that the cells express the protein at higher levels. The heterologous promoter is inserted in such a manner that it is operatively linked to the desired protein encoding sequences. See, for example, PCT International Publication No. WO 94/12650, PCT International Publication No. WO 92/20808, and PCT International Publication No. WO 91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the desired protein coding sequence, amplification of the marker DNA by standard selection methods results in co-amplification of the desired protein coding sequences in the cells.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting. These sequence include polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

5.8 Transgenic Animals

In preferred methods to determine biological functions of the polypeptides of the invention in vivo, one or more genes provided by the invention are either over expressed or inactivated in the germ line of animals using homologous recombination [Capecchi, Science 244:1288–1292 (1989)]. Animals in which the gene is over expressed, under the regulatory control of exogenous or endogenous promoter elements, are known as transgenic animals. Animals in which an endogenous gene has been inactivated by homologous recombination are referred to as "knockout" animals. Knockout animals, preferably non-human mammals, can be prepared as described in U.S. Pat. No. 5,557,032, incorporated herein by reference. Transgenic animals are useful to determine the roles polypeptides of the invention play in biological processes, and preferably in disease states. Transgenic animals are useful as model systems to identify compounds that modulate lipid metabolism. Transgenic animals, preferably non-human mammals, are produced using methods as described in U.S. Pat. No 5,489,743 and PCT Publication No. WO94/28122, incorporated herein by reference.

Transgenic animals can be prepared wherein all or part of a polynucleotides of the invention promoter is either activated or inactivated to alter the level of expression of the polypeptides of the invention. Inactivation can be carried out using homologous recombination methods described above. Activation can be achieved by supplementing or even replacing the homologous promoter to provide for increased protein expression. The homologous promoter can be supplemented by insertion of one or more heterologous enhancer elements known to confer promoter activation in a particular tissue.

5.9 Uses and Biological Activity of Stem Cell Growth Factor-Like Polypeptide Stem cell growth factor-like polypeptide is based on polynucleotides isolated from cDNA libraries prepared from human testis cells (Hyseq clone identification numbers 2880984 and 2881695), from human fetal skin (Hyseq clone identification number 15375176), adult spleen (Hyseq clone identification number 14856094), and human endothelial cells (Hyseq clone identification numbers 13804756, 13687487, 13804756).

Figure 1:
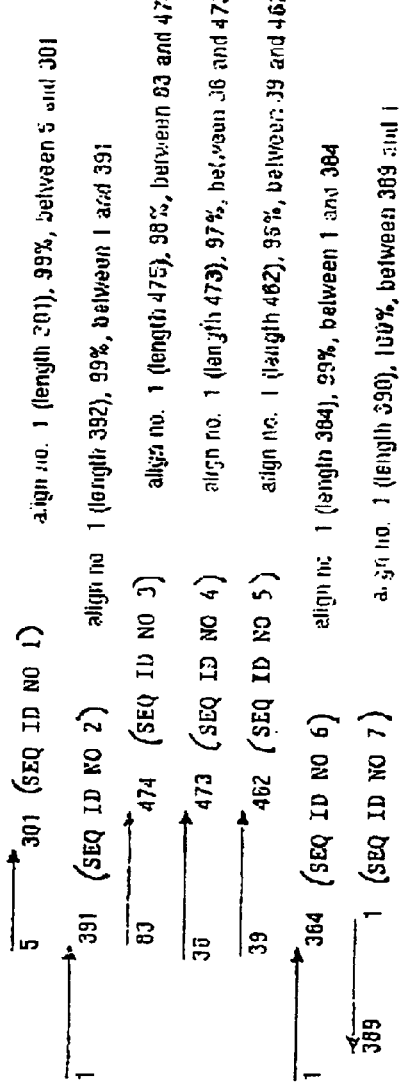

FIG. 1 shows the alignment of polynucleotide SEQ ID NO: 9 and EST sequences SEQ ID NO: 1–7. The nucleic acid sequences of the present invention (SEQ ID NO: 1–9) are expected encode polypeptides having stem cell growth factor activity, including hematopoietic stem cell growth factor activity, as described herein. The polypeptide of SEQ ID NO: 10, fragments thereof, sequences having at least 90% homology, are also expected to have stem cell growth factor activity, including hematopoietic stem cell growth factor activity, as described herein.

The stem cell growth factor-like polypeptide of SEQ ID NO: 10 is an approximately 272-amino acid protein with a predicted molecular mass of approximately 30 kDa unglycosylated. Protein database searches with the BLASTX algorithm (Altschul S. F. et al., J. Mol. Evol. 36:290–300 (1993) and Altschul S. F. et al., J. Mol. Biol. 21:403–10 (1990), herein incorporated by reference) indicate that SEQ ID NO: 10 is homologous to thrombospondin type 1 domain and a human secreted protein clone da 228_6. Protein database search with eMATRIX software (Stanford University, Stanford Calif.) further show that a portion of SEQ ID NO: 10 has a laminin-type EGF-like (LE) domain, a vertebrate metallothioneins domain, an endogenous opioids neuropeptides precursors proteins domain, a membrane attack complex components/perforin proteins domain, an HMG-I and HMG-Y DNA-binding domain proteins (Ahook), an HMG1/2 protein domain, a vertebrate metallothionein signature domain, and a neurohypophysial hormone signature domain.

A predicted approximately twenty-one residue signal peptide is encoded from approximately residue 1 to residue 21 of SEQ ID NO: 10 (SEQ ID NO: 15). The extracellular portion is useful on its own. This can be confirmed by expression in mammalian cells and sequencing of the cleaved product. The signal peptide region was predicted using Neural Network SignalP V1.1 program (Nielsen et al, (1997) Int. J. Neural Syst. 8, 581–599). One of skill in the art will recognize that the actual cleavage site may be different than that predicted by the computer program. SEQ ID NO: 16 is the peptide resulting when the predicted signal peptide is removed from SEQ ID NO: 10.

Using eMATRIX software package (Stanford University, Stanford, Calif.) (Wu et al., J. Comp. Biol., vol. 6, pp. 219–235 (1999), herein incorporated by reference), Siglec-like polypeptide of SEQ ID NO: 10 is expected to have following domains, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine:

Laminin-type EGF-like (LE) domain proteins at

100 ADCDTCFNKNFCTKCKSGFYLHL 122   (SEQ ID NO: 17)

Vertebrate metallothioneins proteins at

92 INKCTKCKADCDTCFNKNFCTKCKSG-
        FYLHLGKCLDNCPEGLEANN 137   (SEQ ID NO: 18)

Endogenous opioids neuropeptides precursors proteins at

33 MHPNVSQGCQGGCATCSDYN 52   (SEQ ID NO: 19)

Membrane attack complex components/perforin proteins at

145 IVHCEVSEWNPWSPCTKKGKTCGFKRGTETRVREIIQ
        181   (SEQ ID NO: 20)

HMG-I and HMG-Y DNA-binding domain proteins (Ahook) at

213 KKGRERKRKK 222   (SEQ ID NO: 21)

HMG1/2 proteins at

198 KCTVQRKKCQKGERGKKGRERKRKKP-
        NKGESKEAIPDSKSLE 239   (SEQ ID NO: 22)

VERTEBRATE METALLOTHIONEIN SIGNATURE at

104 TCFNKNFCTKCKSG 117   (SEQ ID NO: 23)

NEUROHYPOPHYSIAL HORMONE SIGNATURE at

148 CEVSEWNPWSPCTKKGKTCG 167   (SEQ ID NO: 24)

Motif 100–122, a laminin-type EGF-like domain, is a component of extracellular matrix which promotes cell growth. The membrane attack complex component/perforin domain (145–185) is postulated to mediate cell-cell interaction and thus cell growth and differentiation. Neurohypophysial hormone is itself regulated by many other factors including Interleukin-1 beta and Interleukin-6. The presence of these motifs are expected in stem cell growth factor activity.

Stem cell growth factor-like protein and/or fragments or derivatives would have similar activity to stem cell growth factors and anabolic growth factors and receptors.

Polypeptides of the invention having stem cell growth factor-like activity are useful for but not limited to cell growth and morphogenesis, including hematopoietic stem cell growth and/or growth of a particular hematopoietic cell type (such as B or T cells), tissue specific stem cell growth, epithelial cell growth and regulation, ovarian follicle development, promoting nerve cell growth, sustaining neuronal populations, cartilage remodeling, wound repair, bone growth, immunosuppression, immune response modulation, modulating antibody and cell mediated immunity and vascular remodeling. The polypeptides of the invention can therefore be employed in but not limited to the prophylaxis or treatment of disorders and diseases caused by or involving wound healing, growth and development, regulation of cartilage growth and development, vascular remodeling (angiogenesis), immunosuppression, follicle growth and development and neurite growth and development. Polypeptides of the invention can also be used in the production of and maintenance of transplants or epidermal grafts.

The polynucleotides and proteins of the present invention are expected to exhibit one or more of the uses or biological activities (including those associated with assays cited herein) identified herein. Uses or activities described for proteins of the present invention may be provided by administration or use of such proteins or of polynucleotides encoding such proteins (such as, for example, in gene therapies or vectors suitable for introduction of DNA). The mechanism underlying the particular condition or pathology will dictate whether the polypeptides of the invention, the polynucleotides of the invention or modulators (activators or inhibitors) thereof would be beneficial to the subject in need of treatment. Thus, "therapeutic compositions of the invention" include compositions comprising isolated polynucleotides (including recombinant DNA molecules, cloned genes and degenerate variants thereof) or polypeptides of the invention (including full length protein, mature protein and truncations or domains thereof), or compounds and other substances that modulate the overall activity of the target gene products, either at the level of target gene/protein expression or target protein activity. Such modulators include polypeptides, analogs, (variants), including fragments and fusion proteins, antibodies and other binding proteins; chemical compounds that directly or indirectly activate or inhibit the polypeptides of the invention (identified, e.g., via drug screening assays as described herein); antisense polynucleotides and polynucleotides suitable for triple helix formation; and in particular antibodies or other binding partners that specifically recognize one or more epitopes of the polypeptides of the invention.

The protein of the present invention may likewise be involved in cellular activation or in one of the other physiological pathways described herein.

5.9.1 Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

The polypeptides of the invention are also useful for making antibody substances that are specifically immunoreactive with stem cell growth factor-like proteins. Antibodies and portions thereof (e.g., Fab fragments) which bind to the polypeptides of the invention can be used to identify the presence of such polypeptides in a sample. For example, the level of the native protein corresponding to SEQ ID NO: 10 in a tissue sample can be determined as an indication of chrondrocyte differentiation or embryonic status. Such determinations are carried out using any suitable immunoassay format, and any polypeptide of the invention that is specifically bound by the antibody can be employed as a positive control.

Any or all of these research utilities are capable of being developed into reagent grade or kit formal for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

5.9.2 Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Additionally, the polypeptides of the invention can be used as molecular weight markers, and as a food supplement. A polypeptide consisting of SEQ ID NO: 10, for example, has a molecular mass of approximately 30 kDa in its unprocessed and unglycosylated state. Protein food supplements are well known and the formulation of suitable food supplements including polypeptides of the invention is within the level of skill in the food preparation art.

5.9.3 Cytokine and Cell Proliferation/Differentiation Activity

A protein of the present invention may exhibit activity relating to cytokine, cell proliferation (either inducing or inhibiting) or cell differentiation (either inducing or inhibiting) activity or may induce production of other cytokines in certain cell populations. A polynucleotide of the invention can encode a polypeptide exhibiting such attributes. Many protein factors discovered to date, including all known cytokines, have exhibited activity in one or more factor-dependent cell proliferation assays, and hence the assays serve as a convenient confirmation of cytokine activity. The activity of therapeutic compositions of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e, CMK, HUVEC, and Caco. Therapeutic compositions of the invention can be used in the following:

Assays for T-cell or thymocyte proliferation include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., I. Immunol. 149:3778–3783, 1992; Bowman et al., I. Immunol. 152:1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human interleukin-, Schreiber, R. D. In Current Protocols in Immunology. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In Current Protocols in Immunology. J. E. Coligan eds. Vol 1 pp. 6.6.1–6.6.5, John Wiley and Sons, Toronto. 1991; Smith et al., Proc. Natl. Aced. Sci. U.S.A. 83:1857–1861, 1986; Measurement of human Interleukin 11—Bennett, F., Giannotti, J., Clark, S. C. and Turner, K. J. In Current Protocols in Immunology. J. E. Coligan eds. Vol 1 pp. 6.15.1 John Wiley and Sons, Toronto.

1991; Measurement of mouse and human Interleukin 9—Ciarletta, A., Giannotti, J., Clark, S. C. and Turner, K. J. In Current Protocols in Immunology. J. E. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

5.9.4 Stem Cell Growth Factor Activity

Polypeptides of the present invention have been shown to exhibit stem cell growth factor activity and to be involved in the proliferation, differentiation and survival of pluripotent and totipotent stem cells including primordial germ cells, embryonic stem cells, neural stem cells, skeletal muscle stem cells, mesencymal stem cells, hematopoietic stem cells and/or germ line stem cells. Administration of the polypeptide of the invention to stem cells in vivo or ex vivo maintains and expands cell populations in a totipotential or pluripotential state which would be useful for re-engineering damaged or diseased tissues, transplantation including solid organs and bone marrow transplants, manufacture of biopharmaceuticals and the development of bio-sensors. The ability to produce large quantities of human cells has important working applications for the production of human proteins which currently must be obtained from non-human sources or donors, implantation of cells to treat diseases such as Parkinson's, Alzheimer's and other neurodegenerative diseases; tissues for grafting such as bone marrow, skin, cartilage, tendons, bone, muscle (including cardiac muscle), blood vessels, cornea, neural cells, gastrointestinal cells and others; and organs for transplantation such as kidney, liver, pancreas (including islet cells), heart and lung.

It is contemplated that multiple different exogenous growth factors and/or cytokines may be administered in combination with the polypeptide of the invention to achieve the desired effect, including any of the growth factors listed herein, other stem cell maintenance factors, and specifically including stem cell factor (SCF), leukemia inhibitory factor (LIF), Flt-3 ligand (Flt-3L), any of the interleukins, recombinant soluble IL-6 receptor fused to IL-6, macrophage inflammatory protein 1-alpha (MIP-1-alpha), G-CSF, GM-CSF, thrombopoietin (TPO), platelet factor 4 (PF-4), platelet-derived growth factor (PDGF), neural growth factors and basic fibroblast growth factor (bFGF).

Since totipotent stem cells can give rise to virtually any mature cell type, expansion of these cells in culture will facilitate the production of large quantities of mature cells. Techniques for culturing stem cells are known in the art and administration of polypeptides of the invention, optionally with other growth factors and/or cytokines, is expected to enhance the survival and proliferation of the stem cell populations. This can be accomplished by direct administration of the polypeptide of the invention to the culture medium. Alternatively, stroma cells transfected with a polynucleotide that encodes for the polypeptide of the invention can be used as a feeder layer for the stem cell populations in culture or in vivo. Stromal support cells for feeder layers may include embryonic bone marrow fibroblasts, bone marrow stromal cells, fetal liver cells, or cultured embryonic fibroblasts (see U.S. Pat. No. 5,690,926).

Stem cells themselves can be transfected with a polynucleotide of the invention to induce autocrine expression of the polypeptide of the invention. This will allow for generation of undifferentiated totipotential/pluripotential stem cell lines that are useful as is or that can then be differentiated into the desired mature cell types. These stable cell lines can also serve as a source of undifferentiated totipotential/pluripotential mRNA to create cDNA libraries and templates for polymerase chain reaction experiments. These studies would allow for the isolation and identification of differentially expressed genes in stem cell populations that regulate stem cell proliferation and/or maintenance.

Expansion and maintenance of totipotent stem cell populations is useful in the treatment of many pathological conditions. For example, polypeptides of the present invention may be used to manipulate stem cells in culture to give rise to neuroepithelial cells that can be used to augment or replace cells damaged by illness, autoimmune disease, accidental damage or genetic disorders, inflammatory disease, immunodeficiency, leukemia and neoplastic myeloid disorders. The polypeptide of the invention can be useful for inducing the proliferation of neural cells and for the regeneration of nerve and brain tissue, i.e. for the treatment of central and peripheral nervous system diseases and neuropathies, as well as mechanical and traumatic disorders which involve degeneration, death or trauma to neural cells or nerve tissue. In addition, the expanded stem cell populations can also be genetically altered for gene therapy purposes and to decrease host rejection of replacement tissues after grafting or implantation. The polypeptide of the invention can also be useful for inducing the proliferation of cardiac stem cells and for regenerating functional heart tissue following cardiac damage induced by cardiac disorders such as myocardial infarctions and artery blockage. In addition, the polypeptides of the invention may strengthen cardiac muscle cells and prevent and/or repair the heart tissue damage due to heart failure. See Weismann, Science, 287: 1442–1446, 2001; Vogel, Science, 290: 1672–1674, 2000 Kajstura et al., Nature, 410: 701–705, 2001.

Expression of the polypeptide of the invention and its effect on stem cells can also be manipulated to achieve controlled differentiation of the stem cells into more differentiated cell types. A broadly applicable method of obtaining pure populations of a specific differentiated cell type from undifferentiated stem cell populations involves the use of a cell-type specific promoter driving a selectable marker. The selectable marker allows only cells of the desired type to survive. For example, stem cells can be induced to differentiate into cardiomyocytes (Wobus et al., Differentiation, 48: 173–182 , (1991); Klug et al., J. Clin. Invest., 98(1): 216–224, (1998)) or skeletal muscle cells (Browder, L. W. In: *Principles of Tissue Engineering* eds. Lanza et al., Academic Press (1997)). Alternatively, directed differentiation of stem cells can be accomplished by culturing the stem cells in the presence of a differentiation factor such as retinoic acid and an antagonist of the polypeptide of the invention which would inhibit the effects of endogenous stem cell factor activity and allow differentiation to proceed.

In vitro cultures of stem cells can be used to determine if the polypeptide of the invention exhibits stem cell growth factor activity. Stem cells are isolated from any one of various cell sources (including hematopoietic stem cells and embryonic stem cells) and cultured on a feeder layer, as described by Thompson et al. Proc. Natl. Acad. Sci, U.S.A., 92: 7844–7848 (1995), in the presence of the polypeptide of the invention alone or in combination with other growth factors or cytokines. The ability of the polypeptide of the invention to induce stem cells proliferation is determined by colony formation on semi-solid support e.g. as described by Bernstein et al., Blood, 77: 2316–2321 (1991).

5.9.5 Hematopoiesis Regulating Activity

A protein of the present invention may be involved in regulation of hematopoiesis and, consequently, in the treatment of myeloid or lymphoid cell disorders. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional circulating soluble factor activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

Therapeutic compositions of the invention can be used in the following:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lympho-hematopoiesis) include, without limitation, those described in: Methylcellulose colony forming assays, Freshney, M. G. In Culture of Hematopoietic Cells. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In Culture of Hematopoietic Cells. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In Culture of Hematopoietic Cells. R. I. Freshney, et al. eds. Vol pp.163–179, Wiley-Liss, Inc., New York, N.Y. 1994; Long term culture initiating cell assay, Sutherland, H. J. In Culture of Hematopoietic Cells. R. I. Freshney, et al. eds. Vol pp. 139–162, Wiley-Liss, Inc., New York, N.Y. 1994.

5.9.6 Tissue Growth Activity

A protein of the present invention also may be involved in bone, cartilage, tendon, ligament and/or nerve tissue growth or regeneration, as well as in wound healing and tissue repair and replacement, and in healing of burns, incisions and ulcers.

For example, induction of cartilage and/or bone growth in circumstances where bone is not normally formed, has application in the healing of bone fractures and cartilage damage or defects in humans and other animals. Compositions of a protein, antibody, binding partner, or other modulator of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be involved in attracting bone-forming cells, stimulating growth of bone-forming cells, or inducing differentiation of progenitors of bone-forming cells. Treatment of osteoporosis, osteoarthritis, bone degenerative disorders, or periodontal disease, such as through stimulation of bone and/or cartilage repair or by blocking inflammation or processes of tissue destruction (collagenase activity, osteoclast activity, etc.) mediated by inflammatory processes may also be possible using the composition of the invention.

Another category of tissue regeneration activity that may involve the protein of the present invention is tendon/ligament formation. Induction of tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The compositions of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a composition may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a composition of the invention.

Compositions of the invention may also be useful to promote better or faster closure of non-healing wounds, including without limitation pressure ulcers, ulcers associated with vascular insufficiency, surgical and traumatic wounds, and the like.

Compositions of the present invention may also be involved in the generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Inhibition or modulation of fibrotic scarring may allow normal tissue to regenerate.

A composition of the present invention may also be useful for gut protection or regeneration and treatment of lung or liver fibrosis, reperfusion injury in various tissues, and conditions resulting from systemic cytokine damage.

A composition of the present invention may also be useful for promoting or inhibiting differentiation of tissues described above from precursor tissues or cells; or for inhibiting the growth of tissues described above.

Therapeutic compositions of the invention can be used in the following:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, Epidermal Wound Healing, pps. 71–112 (Maibach, H. I. and Rovee, D. T., eds.), Year Book Medical Publishers, Inc., Chicago, as modified by Eaglstein and Mertz, J. Invest. Dermatol 71:382–84 (1978).

5.9.7 Immune Stimulating or Suppressing Activity

Compositions of the present invention may also exhibit immune stimulating or immune suppressing activity, including without limitation the activities for which assays are described herein. A polynucleotide of the invention can encode a polypeptide involved in such activities. A protein or antibody, other binding partner, or other modulator of the invention may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases caused by viral, bacterial, fungal or other infection may be treatable using a protein, antibody, binding partner, or other modulator of the invention, including infections by HIV, hepatitis viruses, herpesviruses, mycobacteria, Leishmania spp., malaria spp. and various fungal infections such as candidiasis, as well as other conditions where a boost to the immune system generally may be desirable, e.g., in the treatment of cancer.

Autoimmune disorders which may involve a protein of the present invention include, for example, connective tissue disease, multiple sclerosis, systemic lupus erythematosus, rheumatoid arthritis, autoimmune pulmonary inflammation, Guillain-Barre syndrome, autoinunune thyroiditis, insulin dependent diabetes mellitis, myasthenia gravis, graft-versus-host disease and autoimmune inflammatory eye disease. Such a protein of the present invention may also to be involved in allergic reactions and conditions, such as asthma (particularly allergic asthma) or other respiratory problems.

Using the proteins, antibody, binding partners, or other modulators of the invention it may also be possible to modulate immune responses, in a number of ways. The immune response may be enhanced or suppressed. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Inmunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing the immune response, e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks the immune response (e.g. a receptor fragment, binding partner, or other modulator such as antisense polynucleotides) may act as an immunosuppressant.

The efficacy of particular immune response modulators in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking the inflammatory response may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of immune responses, may also be useful in therapy. Upregulation of immune responses may be in the form of enhancing an existing immune response or eliciting an initial immune response. For example, enhancing an immune response may be useful in cases of viral infection such as influenza, the common cold, and encephalitis.

Alternatively, anti-viral immune responses may be enhanced in an infected patient by removing T cells from the patient, costimulating the T cells in vitro and reintroducing the in vitro activated T cells into the patient.

The activity of therapeutic compositions of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., I. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Imunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

5.9.8 Activin/Inhibin Activity

A protein of the present invention may also exhibit activin- or inhibin-related activities. A polynucleotide of the invention may encode a polypeptide exhibiting such characteristics. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as, but not limited to, cows, sheep and pigs.

The activity of a protein of the invention may, among other means, be measured by the following methods.

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

5.9.9 Chemotactic/Chemokinetic Activity

A protein of the present invention may be involved in chemotactic or chemokinetic activity for mammalian cells, including, for example, monocytes, fibroblasts, neutrophils, T-cells, mast cells, eosinophils, epithelial and/or endothelial cells. A polynucleotide of the invention can encode a polypeptide exhibiting such attributes. Chemotactic and chemokinetic receptor activation can be used to mobilize or attract a desired cell population to a desired site of action. Chemotactic or chemokinetic compositions (e.g. proteins, antibodies, binding partners, or modulators of the invention) provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

Therapeutic compositions of the invention can be used in the following:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25:1744–1748; Gruber et al. J. of Immunol. 152:5860–5867, 1994; Johnston et al. J. of Immunol. 153:1762–1768, 1994.

5.9.10 Hemostatic and Thrombolytic Activity

A protein of the invention may also be involved in hemostatis or thrombolysis or thrombosis. A polynucleotide of the invention can encode a polypeptide exhibiting such attributes. Compositions may be useful in treatment of various coagulation disorders (including hereditary disorders, such as hemophilias) or to enhance coagulation and other hemostatic events in treating wounds resulting from trauma, surgery or other causes. A composition of the invention may also be useful for dissolving or inhibiting formation of thromboses and for treatment and prevention of conditions resulting therefrom (such as, for example, infarction of cardiac and central nervous system vessels (e.g., stroke).

Therapeutic compositions of the invention can be used in the following:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

5.9.11 Cancer Diagnosis and Therapy

Polypeptides of the invention may be involved in cancer cell generation, proliferation or metastasis. Detection of the presence or amount of polynucleotides or polypeptides of the invention may be useful for the diagnosis and/or prognosis of one or more types of cancer. For example, the presence or increased expression of a polynucleotide/polypeptide of the invention may indicate a hereditary risk of cancer, a precancerous condition, or an ongoing malignancy. Conversely, a defect in the gene or absence of the polypeptide may be associated with a cancer condition. Identification of single nucleotide polymorphisms associated with cancer or a predisposition to cancer may also be useful for diagnosis or prognosis.

Cancer treatments promote tumor regression by inhibiting tumor cell proliferation, inhibiting angiogenesis (growth of new blood vessels that is necessary to support tumor growth) and/or prohibiting metastasis by reducing tumor cell motility or invasiveness. Therapeutic compositions of the invention may be effective in adult and pediatric oncology including in solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, astrocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Karposi's sarcoma.

Polypeptides, polynucleotides, or modulators of polypeptides of the invention (including inhibitors and stimulators of the biological activity of the polypeptide of the invention) may be administered to treat cancer. Therapeutic compositions can be administered in therapeutically effective dosages alone or in combination with adjuvant cancer therapy such as surgery, chemotherapy, radiotherapy, thermotherapy, and laser therapy, and may provide a beneficial effect, e.g. reducing tumor size, slowing rate of tumor growth, inhibiting metastasis, or otherwise improving overall clinical condition, without necessarily eradicating the cancer.

The composition can also be administered in therapeutically effective amounts as a portion of an anti-cancer cocktail. An anti-cancer cocktail is a mixture of the polypeptide or modulator of the invention with one or more anti-cancer drugs in addition to a pharmaceutically acceptable carrier for delivery. The use of anti-cancer cocktails as a cancer treatment is routine. Anti-cancer drugs that are well known in the art and can be used as a treatment in combination with the polypeptide or modulator of the invention include: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16-213), Floxuridine, 5-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Octreotide, Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate.

In addition, therapeutic compositions of the invention may be used for prophylactic treatment of cancer. There are hereditary conditions and/or environmental situations (e.g. exposure to carcinogens) known in the art that predispose an individual to developing cancers. Under these circumstances, it may be beneficial to treat these individuals with therapeutically effective doses of the polypeptide of the invention to reduce the risk of developing cancers.

In vitro models can be used to determine the effective doses of the polypeptide of the invention as a potential cancer treatment. These in vitro models include proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., J. Natl. Can. Inst., 52: 921–30 (1974), mobility and invasive potential of tumor cells in Boyden Chamber assays as described in Pilkington et al., Anticancer Res., 17: 4107–9 (1997), and angiogenesis assays such as induction of vascularization of the chick chorioallantoic membrane or induction of vascular endothelial cell migration as described in Ribatta et al., Intl. J. Dev. Biol., 40: 1189–97 (1999) and Li et al., Clin. Exp. Metastasis, 17:423–9 (1999) respectively. Suitable tumor cells lines are available, e.g. from American Type Tissue Culture Collection catalogs.

5.9.12 Receptor/Ligand Activity

A protein of the present invention may also demonstrate activity as receptor, receptor ligand or inhibitor or agonist of receptor/ligand interactions. A polynucleotide of the invention can encode a polypeptide exhibiting such characteristics. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses. Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

By way of example, the polypeptides of the invention may be used as a receptor for a ligand(s) thereby transmitting the biological activity of that ligand(s). Ligands may be identified through binding assays, affinity chromatography, dihybrid screening assays, BIAcore assays, gel overlay assays, or other methods known in the art.

Studies characterizing drugs or proteins as agonist or antagonist or partial agonists or a partial antagonist require the use of other proteins as competing ligands. The polypeptides of the present invention or ligand(s) thereof may be labeled by being coupled to radioisotopes, calorimetric molecules or a toxin molecules by conventional methods. ("Guide to Protein Purification" Murray P. Deutscher (ed) Methods in Enzymology Vol. 182 (1990) Academic Press, Inc. San Diego). Examples of radioisotopes include, but are not limited to, tritium and carbon-14. Examples of colorimetric molecules include, but are not limited to, fluorescent molecules such as fluorescamine, or rhodamine or other colorimetric molecules. Examples of toxins include, but are not limited, to ricin.

5.9.13 Drug Screening

This invention is particularly useful for screening chemical compounds by using the novel polypeptides or binding fragments thereof in any of a variety of drug screening techniques. The polypeptides or fragments employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between polypeptides of the invention or fragments and the agent being tested or examine the diminution in complex formation between the novel polypeptides and an appropriate cell line, which are well known in the art.

Sources for test compounds that may be screened for ability to bind to or modulate (i.e., increase or decrease) the activity of polypeptides of the invention include (1) inorganic and organic chemical libraries, (2) natural product libraries, and (3) combinatorial libraries comprised of either random or mimetic peptides, oligonucleotides or organic molecules.

Chemical libraries may be readily synthesized or purchased from a number of commercial sources, and may include structural analogs of known compounds or compounds that are identified as "hits" or "leads" via natural product screening.

The sources of natural product libraries are microorganisms (including bacteria and fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and (non-naturally occurring) variants thereof. For a review, see Science 282:63–68 (1998).

Combinatorial libraries are composed of large numbers of peptides, oligonucleotides or organic compounds and can be readily prepared by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701–707 (1997). For reviews and examples of peptidomimetic libraries, see Al-Obeidi et al., Mol. Biotechnol, 9(3):205–23 (1998); Hruby et al., Curr Opin Chem Biol, 1(1):114–19 (1997); Dorner et al., Bioorg Med Chem, 4(5):709–15 (1996) (alkylated dipeptides).

Identification of modulators through use of the various libraries described herein permits modification of the candidate "hit" (or "lead") to optimize the capacity of the "hit" to bind a polypeptide of the invention. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

The binding molecules thus identified may be complexed with toxins, e.g., ricin or cholera, or with other compounds that are toxic to cells such as radioisotopes. The toxin-binding molecule complex is then targeted to a tumor or other cell by the specificity of the binding molecule for a polypeptide of the invention. Alternatively, the binding molecules may be complexed with imaging agents for targeting and imaging purposes.

5.9.14 Assay for Receptor Activity

The invention also provides methods to detect specific binding of a polypeptide e.g. a ligand or a receptor. The art provides numerous assays particularly useful for identifying previously unknown binding partners for receptor polypeptides of the invention. For example, expression cloning using mammalian or bacterial cells, or dihybrid screening assays can be used to identify polynucleotides encoding binding partners. As another example, affinity chromatography with the appropriate immobilized polypeptide of the invention can be used to isolate polypeptides that recognize and bind polypeptides of the invention. There are a number of different libraries used for the identification of compounds, and in particular small molecule, that modulate (i.e., increase or decrease) biological activity of a polypeptide of the invention. Ligands for receptor polypeptides of the invention can also be identified by adding exogenous ligands, or cocktails of ligands to two cells populations that are genetically identical except for the expression of the receptor of the invention: one cell population expresses the receptor of the invention whereas the other does not. The response of the two cell populations to the addition of ligands(s) are then compared. Alternatively, an expression library can be co-expressed with the polypeptide of the invention in cells and assayed for an autocrine response to identify potential ligand(s). As still another example, BIAcore assays, gel overlay assays, or other methods known in the art can be used to identify binding partner polypeptides, including, (1) organic and inorganic chemical libraries, (2) natural product libraries, and (3) combinatorial libraries comprised of random peptides, oligonucleotides or organic molecules.

The role of downstream intracellular signaling molecules in the signaling cascade of the polypeptide of the invention can be determined. For example, a chimeric protein in which the cytoplasmic domain of the polypeptide of the invention is fused to the extracellular portion of a protein, whose ligand has been identified, is produced in a host cell. The cell is then incubated with the ligand specific for the extracellular portion of the chimeric protein, thereby activating the chimeric receptor. Known downstream proteins involved in intracellular signaling can then be assayed for expected modifications i.e. phosphorylation. Other methods known to those in the art can also be used to identify signaling molecules involved in receptor activity.

5.9.15 Anti-inflammatory Activity

Compositions of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Compositions with such activities can be used to treat inflammatory conditions including chronic or acute conditions), including without limitation intimation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Compositions of the invention may also be useful to treat anaphylaxis and hypersensitivity to an antigenic substance or material. Compositions of this invention may be utilized to prevent or treat condition such as, but not limited to, utilized, for example, as part of methods for the prevention and/or treatment of disorders involving sepsis, acute pancreatitis, endotoxin shock, cytokine induced shock, rheumatoid arthritis, chronic inflammatory arthritis, pancreatic cell damage from diabetes mellitus type 1, graft versus host disease, inflammatory bowel disease, inflamation associated with pulmonary disease, other autoimmune disease or inflammatory disease, an antiproliferative agent such as for acute or chronic mylegenous leukemia or in the prevention of premature labor secondary to intrauterine infections.

5.9.16 Leukemias

Leukemias and related disorders may be treated or prevented by administration of a therapeutic that promotes or inhibits function of the polynucleotides and/or polypeptides of the invention. Such leukemias and related disorders include but are not limited to acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia and chronic lymphocytic leukemia (for a review of such disorders, see Fishman et al., 1985, Medicine, 2d Ed., J. B. Lippincott Co., Philadelphia).

5.9.17 Nervous System Disorders

Nervous system disorders, involving cell types which can be tested for efficacy of intervention with compounds that modulate the activity of the polynucleotides and/or polypeptides of the invention, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(iv) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(v) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vi) neurological lesions associated with systemic diseases including but not limited to diabetes (diabetic neuropathy, Bell's palsy), systemic lupus erythematosus, carcinoma, or sarcoidosis;

(vii) lesions caused by toxic substances including alcohol, lead, or particular neurotoxins; and (viii) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons. For example, and not by way of limitation, therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.9.18 Arthritis and Inflammation

The immunosuppressive effects of the compositions of the invention against rheumatoid arthritis is determined in an experimental animal model system. The experimental model system is adjuvant induced arthritis in rats, and the protocol is described by J. Holoshitz, et at., 1983, Science, 219:56, or by B. Waksman et al., 1963, Int. Arch. Allergy Appl. Immunol., 23:129. Induction of the disease can be caused by a single injection, generally intradermally, of a suspension of killed Mycobacterium tuberculosis in complete Freund's adjuvant (CFA). The route of injection can vary, but rats may be injected at the base of the tail with an adjuvant mixture. The inhibitor is administered in phosphate buffered solution (PBS) at a dose of about 1–5 mg/kg. The control consists of administering PBS only.

The procedure for testing the effects of the test compound would consist of intradermally injecting killed Mycobacterium tuberculosis in CFA followed by immediately administering the inhibitor and subsequent treatment every other day until day 24. At 14, 15, 18, 20, 22, and 24 days after injection of Mycobacterium CFA, an overall arthritis score may be obtained as described by J. Holoskitz above. An analysis of the data would reveal that the test compound would have a dramatic affect on the swelling of the joints as measured by a decrease of the arthritis score.

5.9.19 Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, co-factors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

5.9.20 Identification of Polymorphisms

The demonstration of polymorphisms makes possible the identification of such polymorphisms in human subjects and the pharmacogenetic use of this information for diagnosis and treatment. Such polymorphisms may be associated with, e.g., differential predisposition or susceptibility to various disease states (such as disorders involving inflammation or immune response) or a differential response to drug administration, and this genetic information can be used to tailor preventive or therapeutic treatment appropriately. For example, the existence of a polymorphism associated with a predisposition to inflammation or autoimmune disease makes possible the diagnosis of this condition in humans by identifying the presence of the polymorphism.

Polymorphisms can be identified in a variety of ways known in the art which all generally involve obtaining a sample from a patient, analyzing DNA from the sample, optionally involving isolation or amplification of the DNA, and identifying the presence of the polymorphism in the DNA. For example, PCR may be used to amplify an appropriate fragment of genomic DNA which may then be sequenced. Alternatively, the DNA may be subjected to allele-specific oligonucleotide hybridization (in which appropriate oligonucleotides are hybridized to the DNA under conditions permitting detection of a single base mismatch) or to a single nucleotide extension assay (in which an oligonucleotide that hybridizes immediately adjacent to the position of the polymorphism is extended with one or more labeled nucleotides). In addition, traditional restriction fragment length polymorphism analysis (using restriction enzymes that provide differential digestion of the genomic DNA depending on the presence or absence of the polymorphism) may be performed. Arrays with nucleotide sequences of the present invention can be used to detect polymorphisms. The array can comprise modified nucleotide sequences of the present invention in order to detect the nucleotide sequences of the present invention. In the alternative, any one of the nucleotide sequences of the present invention can be placed on the array to detect changes from those sequences.

Alternatively a polymorphism resulting in a change in the amino acid sequence could also be detected by detecting a corresponding change in amino acid sequence of the protein, e.g., by an antibody specific to the variant sequence.

5.10 Therapeutic Methods

The compositions (including polypeptide fragments, analogs, variants and antibodies or other binding partners or modulators including antisense polynucleotides) of the invention have numerous applications in a variety of therapeutic methods. Examples of therapeutic applications include, but are not limited to, those exemplified herein.

5.10.1 Examples

Another embodiment of the invention is the administration of an effective amount of the polypeptide or other composition of the invention to individuals affected by a disease or disorder which can be modulated by regulating the IgSF member of the invention. While the mode of administration is not particularly important, parenteral administration is preferred. An exemplary mode of administration is to deliver an intravenous bolus. The dosage of the polypeptide or composition of the invention will normally be determined by the prescribing physician. It is to be expected that the dosage will vary according to the age, weight, condition and response of the individual patient. Typically, the amount of protein or other active ingredient administered per dose will be in the range of about 0.1 to 25 mg/kg of body weight, with the preferred dose being about 0.1 to 10 mg/kg of patient body weight. For parenteral administration, the polypeptides or other active ingredient of the invention will be formulated in an injectable form that includes a pharmaceutically acceptable parenteral vehicle. Such vehicles are well known in the art and examples include water, saline, Ringer's solution, dextrose. solution, and solutions consisting of small amounts of the human serum albumin. The vehicle may contain minor amounts of additives that maintain the isotonicity and stability of the polypeptide or other active ingredient. The preparation of such solutions is within the skill of the art. Typically, the cytokine inhibitor will be formulated in such vehicles at a concentration of about 1–8 mg/nl to about 10 mg/ml.

5.11 Pharmaceutical Formulations and Routes of Administration

A protein or other composition of the present invention (from whatever source derived, including without limitation from recombinant and non-recombinant sources and including antibodies and other binding partners of the polypeptides of the invention) may be administered to a patient in need, by itself, or in pharmaceutical compositions where it is mixed with suitable carriers or excipient(s) at doses to treat or ameliorate a variety of disorders. Such a composition may optionally contain (in addition to protein or other active ingredient and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL4, IL-5, IL-6, IL-7, IL-8, IL-9, IL-10, IL-11, IL-12, IL-13, IL-14, IL-15, IFN, TNF-, TNF1, TNF2, G-CSF, Meg-CSF, thrombopoietin, stem cell factor, and erythropoietin. In further compositions, proteins of the invention may be combined with other agents beneficial to the treatment of the bone and/or cartilage defect, wound, or tissue in questions. These agents include various growth factors such as epidermal growth factor (EGF), platelet-derived growth factor (PDGF), transforming growth factors (TGF- and TGF-), insulin-like growth factor (IGF), as well as cytokines described herein.

The pharmaceutical composition may further contain other agents which either enhance the activity of the protein or other active ingredient or compliment its activity or use in treatment. Such additional factors and/or agents may be included in the pharmaceutical composition to produce a synergistic effect with protein or other active ingredient of the invention, or to minimize side effects. Conversely, protein or other active ingredient of the present invention may be included in formulations of the particular cytokine, lymphokine, other hematopoietic factor, thrombolytic or anti-thrombotic factor, or anti- inflammatory agent to minimize side effects of the cytokine, lymphokine, other hematopoietic factor, thrombolytic or anti-thrombotic factor, or anti-inflammatory agent. A protein of the present invention may be active in multimers (e.g., heterodimers or homodimers) or complexes with itself or other proteins. As a result, pharmaceutical compositions of the invention may comprise a protein of the invention in such multimeric or complexed form.

As an alternative to being included in a pharmaceutical composition of the invention including a first protein, a second protein or a therapeutic agent may be concurrently administered with the first protein (e.g., at the same time, or at differing times provided that therapeutic concentrations of the combination of agents is achieved at the treatment site). Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein or other active ingredient of the present invention is administered to a mammal having a condition to be treated. Protein or other active ingredient of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein or other active ingredient of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein or other active ingredient of the present invention in combination with cytokine(s), lymphokine(s), other hematopoietic factor(s), thrombolytic or anti-thrombotic factors.

5.11.1 Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein or other active ingredient of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops. Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

The polypeptides of the invention are administered by any route that delivers an effective dosage to the desired site of action. The determination of a suitable route of administration and an effective dosage for a particular indication is within the level of skill in the art. Preferably for wound treatment, one administers the therapeutic compound directly to the site. Suitable dosage ranges for the polypeptides of the invention can be extrapolated from these dosages or from similar studies in appropriate animal models. Dosages can then be adjusted as necessary by the clinician to provide maximal therapeutic benefit.

5.11.2 Compositions/Formulations

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein or other active ingredient of the present invention is administered orally, protein or other active ingredient of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein or other active ingredient of the present invention, and preferably from about 25 to 90% protein or other active ingredient of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein or other active ingredient of the present invention, and preferably from about 1 to 50% protein or other active ingredient of the present invention.

When a therapeutically effective amount of protein or other active ingredient of the present invention is administered by intravenous, cutaneous or subcutaneous injection, protein or other active ingredient of the present invention will be in the form of a pyrogen-free, parenterally acceptable aqueous solution. The preparation of such parenterally acceptable protein or other active ingredient solutions, having due regard to pH, isotonicity, stability, and the like, is within the skill in the art. A preferred pharmaceutical composition for intravenous, cutaneous, or subcutaneous injection should contain, in addition to protein or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein or other active ingredient stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the active ingredients of the invention may be provided as salts with pharmaceutically compatible counterions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) or other active ingredient of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention. The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithins, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein or other active ingredient of the present invention in the pharmaceutical composition of the present invention will depend upon the nature and severity of the condition being treated, and on the nature of prior treatments which the patient has undergone. Ultimately, the attending physician will decide the amount of protein or other active ingredient of the present invention with which to treat each individual patient. Initially, the attending physician will administer low doses of protein or other active ingredient of the present invention and observe the patient's response. Larger doses of protein or other active ingredient of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 $\mu$g to about 10 mg, more preferably about 0.1 $\mu$g to about 1 mg) of protein or other active ingredient of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein or other active ingredient of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing or other active ingredient-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalcium phosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorption of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins or other active ingredient of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF- and TGF-), and insulin-like growth factor (IGF).

The therapeutic compositions are also presently valuable for veterinary applications. Particularly domestic animals and thoroughbred horses, in addition to humans, are desired patients for such treatment with proteins or other active ingredient of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

5.11.3. Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amount is well within the capability of those skilled in the art, especially in light of the detailed disclosure provided herein. For any compound used in the method of the invention, the therapeutically effective dose can be estimated initially from appropriate in vitro assays. For example, a dose can be formulated in animal models to achieve a circulating concentration range that can be used to more accurately determine useful doses in humans. For example, a dose can be formulated in animal models to achieve a circulating concentration range that includes the $IC_{50}$ as determined in cell culture (i.e., the concentration of the test compound which achieves a half-maximal inhibition of the IgSF protein's biological activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p.1. Dosage amount and interval may be adjusted individually to provide plasma levels of the active moiety which are sufficient to maintain the desired effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

An exemplary dosage regimen for polypeptides or other compositions of the invention will be in the range of about 0.01 to 100 mg/kg of body weight daily, with the preferred dose being about 0.1 to 25 mg/kg of patient body weight daily, varying in adults and children. Dosing may be once daily, or equivalent doses may be delivered at longer or shorter intervals.

The amount of composition administered will, of course, be dependent on the subject being treated, on the subject's age and weight, the severity of the affliction, the manner of administration and the judgment of the prescribing physician.

5.11.4. Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

5.12 Antibodies

Also included in the invention are antibodies to proteins, or fragments of proteins of the invention. The term "antibody" as used herein refers to immunoglobulin molecules and immunologically active portions of immunoglobulin (Ig) molecules, i.e., molecules that contain an antigen-binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, an antibody molecule obtained from humans relates to any of the classes IgG, IgM, IgA, IgE, and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses, and types of human antibody species.

An isolated related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO: 10, 13–24, 32 or 34 and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of TGF alpha-like protein that is located on the surface of the protein, e.g., a hydrophilic region. A hydrophobicity analysis of the human related protein sequence will indicate which regions of a related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immuno-specifically bind these protein components.

The term "specific for" indicates that the variable regions of the antibodies of the invention recognize and bind polypeptides of the invention exclusively (i.e., able to distinguish the polypeptide of the invention from other similar polypeptides despite sequence identity, homology, or similarity found in the family of polypeptides), but may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies that recognize and bind fragments of the polypeptides of the invention are also contemplated, provided that the antibodies are first and foremost specific for, as defined above, full-length polypeptides of the invention. As with antibodies that are specific for full length polypeptides of the invention, antibodies of the invention that recognize fragments are those which can distinguish polypeptides from the same family of polypeptides despite inherent sequence identity, homology, or similarity found in the family of proteins.

Antibodies of the invention are useful for, for example, therapeutic purposes (by modulating activity of a polypeptide of the invention), diagnostic purposes to detect or quantitate a polypeptide of the invention, as well as purification of a polypeptide of the invention. Kits comprising an antibody of the invention for any of the purposes described herein are also comprehended. In general, a kit of the invention also includes a control antigen for which the antibody is immunospecific. The invention further provides a hybridoma that produces an antibody according to the invention. Antibodies of the invention are useful for detection and/or purification of the polypeptides of the invention.

Monoclonal antibodies binding to the protein of the invention may be useful diagnostic agents for the immuno-detection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

The labeled antibodies of the present invention can be used for in vitro, in vivo, and in situ assays to identify cells or tissues in which a fragment of the polypeptide of interest is expressed. The antibodies may also be used directly in therapies or other diagnostics. The present invention further provides the above-described antibodies immobilized on a solid support. Examples of such solid supports include plastics such as polycarbonate, complex carbohydrates such as agarose and Sepharose®, acrylic resins and such as polyacrylamide and latex beads. Techniques for coupling antibodies to such solid supports are well known in the art (Weir, D. M. et al., "Handbook of Experimental Immunology" 4th Ed., Blackwell Scientific Publications, Oxford, England, Chapter 10 (1986); Jacoby, W. D. et al., Meth. Enzym. 34 Academic Press, N.Y. (1974)). The immobilized antibodies of the present invention can be used for in vitro, in vivo, and in situ assays as well as for immuno-affinity purification of the proteins of the present invention.

Various procedures known within the art may be used for the production of polyclonal or monoclonal antibodies directed against a protein of the invention, or against derivatives, fragments, analogs homologs, or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

5.12.1 Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface-active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants that can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilizied on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

5.12.2 Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen-binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof, or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59–103). Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, Marcel Dekker, Inc., New York, (1987) pp. 51–63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

5.12.3 Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains, or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. (See also U.S. Pat. No. 5,225,539). In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

5.12.4 Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: Monoclonal Antibodies and Cancer Therapy, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: Monoclonal Antibodies and Cancer Therapy, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (Nature 368, 812–13 (1994)); Fishwild et al, (*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals that are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells that secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

5.12.5 Fab Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

5.12.6 Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature,* 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., 1991 *EMBO J.,* 10:3655–3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fissions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

According to another approach described in WO 96/27011, the interface between a pair of antibody molecules can be engineered to maximize the percentage of heterodimers that are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444 6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (Fc R), such as Fc RI (CD64), Fc RIII (CD32) and Fc RIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

5.12.7 Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

5.12.8 Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity can also be prepared using heterobifunctional cross-linkers as described in Wolff et al. Cancer Research, 53: 2560–2565 (1993). Alternatively, an antibody can be engineered that has dual Fc regions and can thereby have enhanced complement lysis and ADCC capabilities. See Stevenson et. al., Anti-Cancer Drug Design, 3: 219–230 (1989).

5.12.9 Immunoconjugates

The invention also pertans to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol)propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987): Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

5.13 Computer Readable Sequences

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention. As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing any of the nucleotide sequences SEQ ID NO: 1–9, 11, 12, 31 or 33 or a representative fragment thereof; or a nucleotide sequence at least 99.9% identical to any of the nucleotide sequences of the SEQ ID NO: 1–9, 11, 12, 31 or 33 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., J. Mol. Biol. 215:403–410 (1990)) and BLAZE (Brudag et al., Comp. Chem. 17:203–207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, Smith-Waterman, MacPattern (EMBL), BLASTN and BLASTA (NPOLYPEPTIDEIA).

A skilled artisan can readily recognize that any one of the available algorithms or implementing software packages for conducting homology searches can be adapted for use in the present computer-based systems. As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

5.14 Expression Modulating Sequences

EMF sequences can be identified within a genome by their proximity to the ORFs. An intergenic segment, or a fragment of the intergenic segment, from about 10 to 200 nucleotides in length, taken 5' from any ORF will modulate the expression of an operably linked 3' ORF in a fashion similar to that found with the naturally linked ORF sequence. As used herein, an "intergenic segment" refers to the fragments of a genome which are between two ORF(S) herein described. Alternatively, EMFs can be identified using known EMFs as a target sequence or target motif in the computer-based systems of the present invention.

The presence and activity of an EMF can be confirmed using an EMF trap vector. An EMF trap vector contains a cloning site 5' to a marker sequence. A marker sequence encodes an identifiable phenotype, such as antibiotic resistance or a complementing nutrition auxotrophic factor, which can be identified or assayed when the EMF trap vector is placed within an appropriate host under appropriate conditions. As described above, an EMF will modulate the expression of an operably linked marker sequence. A more detailed discussion of various marker sequences is provided below. A sequence which is suspected of being an EMF is cloned in all three reading frames in one or more restriction sites upstream from the marker sequence in the EMF trap vector. The vector is then transformed into an appropriate host using known procedures and the phenotype of the transformed host is examined under appropriate conditions. As described above, an EMF will modulate the expression of an operably linked marker sequence.

5.15 Triple Helix Formation

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., Nucl. Acids Res. 6:3073 (1979); Cooney et al., Science 15241:456 (1988); and Dervan et al., Science 251:1360(1991)) or to the mRNA itself (antisense—Olmno, J. Neurochem. 56:560 (1991); Oligodeoxynucleotides as Antisense Inhibitors of Gene Expression, CRC. Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

5.16 Diagnostic Assays and Kits

The present invention further provides methods to identify the presence or expression of one of the ORFs of the present invention, or homolog thereof, in a test sample, using a nucleic acid probe or antibodies of the present invention, optionally conjugated or otherwise associated with a suitable label.

In general, methods for detecting a polynucleotide of the invention can comprise contacting a sample with a compound that binds to and forms a complex with the polynucleotide for a period sufficient to form the complex, and detecting the complex, so that if a complex is detected, a polynucleotide of the invention is detected in the sample. Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a polypeptide of the invention can comprise contacting a sample with a compound that binds to and forms a complex with the polypeptide for a period sufficient to form the complex, and detecting the complex, so that if a complex is detected, a polypeptide of the invention is detected in the sample.

In detail, such methods comprise incubating a test sample with one or more of the antibodies or one or more of the nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

5.17 Medical Imaging

The novel polypeptides and binding partners of the invention are useful in medical imaging of sites expressing the molecules of the invention (e.g., where the polypeptide of the invention is involved in the immune response, for imaging sites of inflammation or infection). See, e.g., Kunkel et al., U.S. Pat. NO. 5,413,778. Such methods involve chemical attachment of a labeling or imaging agent, administration of the labeled polypeptide to a subject in a pharmaceutically acceptable carrier, and imaging the labeled polypeptide in vivo at the target site.

5.18 Screening Assays

Using the isolated proteins and polynucleotides of the invention, the present invention further provides methods of obtaining and identifying agents which bind to a polypeptide encoded by an ORF corresponding to any of the nucleotide sequences set forth in the SEQ ID NO: 1–9, 11, 12, 31 or 33 or bind to a specific domain of the polypeptide encoded by the nucleic acid. In detail, said method comprises the steps of:

(a) contacting an agent with an isolated protein encoded by an ORF of the present invention, or nucleic acid of the invention; and (b) determining whether the agent binds to said protein or said nucleic acid.

In general, therefore, such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polynucleotide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a receptor gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides," In Synthetic Peptides, A User's Guide, W. H. Freeman, NY (1992), pp. 289–307, and Kaspczak et al., Biochemistry 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents. Agents which bind to a protein encoded by one of the ORFs of the present invention can be used as a diagnostic agent, in the control of bacterial infection by modulating the activity of the protein encoded by the ORF. Agents which bind to a protein encoded by one of the ORFs of the present invention can be formulated using known techniques to generate a pharmaceutical composition.

5.19 Use of Nucleic Acids As Probes

Another aspect of the subject invention is to provide for polypeptide-specific nucleic acid hybridization probes capable of hybridizing with naturally occurring nucleotide sequences. The hybridization probes of the subject invention may be derived from any of the nucleotide sequences SEQ ID NO: 1–9, 11, 12, 31 or 33. Because the corresponding gene is only expressed in a limited number of tissues, a hybridization probe derived from of any of the nucleotide sequences SEQ ID NO: 1–9, 11, 12, 31 or 33 can be used as an indicator of the presence of RNA of cell type of such a tissue in a sample.

Any suitable hybridization technique can be employed, such as, for example, in situ hybridization. PCR as described in U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals. The nucleotide sequence may be used to produce purified polypeptides using well known methods of recombinant DNA technology. Among the many publications that teach methods for the expression of genes after they have been isolated is Goeddel (1990) Gene Expression Technology, Methods and Enzymology, Vol 185, Academic Press, San Diego. Polypeptides may be expressed in a variety of host cells, either prokaryotic or eukaryotic. Host cells may be from the same species from which a particular polypeptide nucleotide sequence was isolated or from a different species. Advantages of producing polypeptides by recombinant DNA technology include obtaining adequate amounts of the protein for purification and the availability of simplified purification procedures.

5.20 Preparation of Sequencing Chips and Arrays

A basic example is using 6-mers attached to 50 micron surfaces to give a chip with dimensions of 3×3 mm which can be combined to give an array of 20×20 cm. Another example is using 9-mer oligonucleotides attached to 10×10 microns surface to create a 9-mer chip, with dimensions of 5×5 mm. 4000 units of such chips may be used to create a 30×30 cm array. In an array in which 4,000 to 16,000 oligochips are arranged into a square array. A plate, or collection of tubes, as also depicted, may be packaged with the array as part of the sequencing kit.

The arrays may be separated physically from each other or by hydrophobic surfaces. One possible way to utilize the hydrophobic strip separation is to use technology such as the Iso-Grid Microbiology System produced by QA Laboratories, Toronto, Canada.

Hydrophobic grid membrane filters (HGMF) have been in use in analytical food microbiology for about a decade where they exhibit unique attractions of extended numerical range and automated counting of colonies. One commercially-available grid is ISO-GRID™ from QA Laboratories Ltd. (Toronto, Canada) which consists of a square (60×60 cm) of polysulfone polymer (Gelman Tuffryn HT-450, 0.45 u pore size) on which is printed a black hydrophobic ink grid consisting of 1600 (40×40) square cells. HGMF have previously been inoculated with bacterial suspensions by vacuum filtration and incubated on the differential or selective media of choice.

Because the microbial growth is confined to grid cells of known position and size on the membrane, the HGMF functions more like an MPN apparatus than a conventional plate or membrane filter. Peterkin et al. (1987) reported that these HGMFs can be used to propagate and store genomic libraries when used with a HGMF replicator. One such instrument replicates growth from each of the 1600 cells of the ISO-GRID and enables many copies of the master HGMF to be made (Peterkin et al., 1987).

Sharpe et al. (1989) also used ISO-RID HGMF form QA Laboratories and an automated HGMF counter (MI-100 Interpreter) and RP-100 Replicator. They reported a technique for maintaining and screening many microbial cultures.

Peterkin and colleagues later described a method for screening DNA probes using the hydrophobic grid-membrane filter (Peterkin et al., 1989). These authors reported methods for effective colony hybridization directly on HGMFs. Previously, poor results had been obtained due to the low DNA binding capacity of the epoxysulfone polymer on which the HGMFs are printed. However, Peterkin et al. (1989) reported that the binding of DNA to the surface of the membrane was improved by treating the replicated and incubated HGMF with polyethyleneimine, a polycation, prior to contact with DNA. Although this early work uses cellular. DNA attachment, and has a different objective to the present invention, the methodology described may be readily adapted for Format 3 SBH.

In order to identify useful sequences rapidly, Peterkin et al. (1989) used radiolabeled plasmid DNA from various clones and tested its specificity against the DNA on the prepared HGMFs. In this way, DNA from recombinant plasmids was rapidly screened by colony hybridization against 100 organisms on HGMF replicates which can be easily and reproducibly prepared.

Manipulation with small (2–3 mm) chips, and parallel execution of thousands of the reactions. The solution of the invention is to keep the chips and the probes in the corresponding arrays. In one example, chips containing 250,000 9-mers are synthesized on a silicon wafer in the form of 8×8 mM plates (15 M/oligonucleotide, Pease et al., 1994) arrayed in 8×12 format (96 chips) with a 1 mM groove in between. Probes are added either by multichannel pipette or pin array, one probe on one chip. To score all 4000 6-mers, 42 chip arrays have to be used, either using different ones, or by reusing one set of chip arrays several times.

In the above case, using the earlier nomenclature of the application, F=9; P=6; and F+P=15. Chips may have probes of formula BxNn, where x is a number of specified bases B; and n is a number of non-specified bases, so that x=4 to 10 and n=1 to 4. To achieve more efficient hybridization, and to avoid potential influence of any support oligonucleotides, the specified bases can be surrounded by unspecified bases, thus represented by a formula such as (N)nBx(N)m.

5.21 Preparation of Support Bound Oligonucleotides

Oligonucleotides, i.e., small nucleic acid segments, may be readily prepared by, for example, directly synthesizing the oligonucleotide by chemical means, as is commonly practiced using an automated oligonucleotide synthesizer.

Support bound oligonucleotides may be prepared by any of the methods known to those of skill in the art using any suitable support such as glass, polystyrene or Teflon. One strategy is to precisely spot oligonucleotides synthesized by standard synthesizers. Immobilization can be achieved using passive adsorption (Inouye & Hondo, 1990); using UV light (Nagata et al., 1985; Dahlen et al., 1987; Morriey & Collins, 1989) or by covalent binding of base modified DNA (Keller et al., 1988; 1989); all references being specifically incorporated herein.

Another strategy that may be employed is the use of the strong biotin-streptavidin interaction as a linker. For example, Broude et al. (1994) describe the use of Biotinylated probes, although these are duplex probes, that are immobilized on streptavidin-coated magnetic beads. Streptavidin-coated beads may be purchased from Dynal, Oslo. Of course, this same linking chemistry is applicable to coating any surface with streptavidin. Biotinylated probes may be purchased from various sources, such as, e.g., Operon Technologies (Alameda, Calif.).

Nunc Laboratories (Naperville, Ill.) is also selling suitable material that could be used. Nunc Laboratories have developed a method by which DNA can be covalently bound to the microwell surface termed Covalink NH. CovaLink NH is a polystyrene surface grafted with secondary amino groups (>NH) that serve as bridge-heads for further covalent coupling. CovaLink Modules may be purchased from Nunc Laboratories. DNA molecules may be bound to CovaLink exclusively at the 5'-end by a phosphoramidate bond, allowing immobilization of more than 1 pmol of DNA (Rasmussen et al., 1991).

The use of CovaLink NH strips for covalent binding of DNA molecules at the 5'-end has been described (Rasmussen et al., 1991). In this technology, a phosphoramidate bond is employed (Chu et al., 1983). This is beneficial as immobilization using only a single covalent bond is preferred. The phosphoramidate bond joins the DNA to the CovaLink NH secondary amino groups that are positioned at the end of spacer arms covalently grafted onto the polystyrene surface through a 2 nm long spacer arm. To link an oligonucleotide to CovaLink NH via an phosphoramidate bond, the oligonucleotide terminus must have a 5'-end phosphate group. It is, perhaps, even possible for biotin to be covalently bound to CovaLink and then streptavidin used to bind the probes.

More specifically, the linkage method includes dissolving DNA in water (7.5 ng/ul) and denaturing for 10 min. at 95° C. and cooling on ice for 10 min. Ice-cold 0.1 M 1-methylimidazole, pH 7.0 (1-MeIm$_7$), is then added to a fmal concentration of 10 mM 1-MeIm$_7$. A ss DNA solution is then dispensed into CovaLink NH strips (75 ul/well) standing on ice.

Carbodiimide 0.2 M 1-ethyl-3-(3-dimethylaminopropyl)-carbodiimide (EDC), dissolved in 10 mM 1-MeIm$_7$, is made fresh and 25 ul added per well. The strips are incubated for 5 hours at 50° C. After incubation the strips are washed using, e.g., Nunc-Immuno Wash; first the wells are washed 3 times, then they are soaked with washing solution for 5 min., and finally they are washed 3 times (where in the washing solution is 0.4 N NaOH, 0.25% SDS heated to 50° C.).

It is contemplated that a further suitable method for use with the present invention is that described in PCT Patent Application WO 90/03382 (Southern & Maskos), incorporated herein by reference. This method of preparing an oligonucleotide bound to a support involves attaching a nucleoside 3'-reagent through the phosphate group by a covalent phosphodiester link to aliphatic hydroxyl groups carried by the support. The oligonucleotide is then synthesized on the supported nucleoside and protecting groups removed from the synthetic oligonucleotide chain under standard conditions that do not cleave the oligonucleotide from the support. Suitable reagents include nucleoside phosphoramidite and nucleoside hydrogen phosphorate.

An on-chip strategy for the preparation of DNA probe for the preparation of DNA probe arrays may be employed. For example, addressable laser-activated photodeprotection may be employed in the chemical synthesis of oligonucleotides directly on a glass surface, as described by Fodor et al. (1991), incorporated herein by reference. Probes may also be immobilized on nylon supports as described by Van Ness el al. (1991); or linked to Teflon using the method of Duncan & Cavalier (1988); all references being specifically incorporated herein.

To link an oligonucleotide to a nylon support, as described by Van Ness et al. (1991), requires activation of the nylon surface via alkylation and selective activation of the 5'-amine of oligonucleotides with cyanuric chloride.

One particular way to prepare support bound oligonucleotides is to utilize the light-generated synthesis described by Pease et al., (1994, incorporated herein by reference). These authors used current photolithographic techniques to generate arrays of immobilized oligonucleotide probes (DNA chips). These methods, in which light is used to direct the synthesis of oligonucleotide probes in high-density, miniaturized arrays, utilize photolabile 5'-protected N-acyl-deoxynucleoside phosphoramidites, surface linker chemistry and versatile combinatorial synthesis strategies. A matrix of 256 spatially defined oligonucleotide probes may be generated in this manner and then used in the advantageous Format 3 sequencing, as described herein.

5.22 Preparation of Nucleic Acid Fragments

The nucleic acids to be sequenced may be obtained from any appropriate source, such as cDNAs, genomic DNA, chromosomal DNA, microdissected chromosome bands, cosmid or YAC inserts, and RNA, including mRNA without any amplification steps. For example, Sambrook et al. (1989) describes three protocols for the isolation of high molecular weight DNA from mammalian cells (p. 9.14–9.23).

DNA fragments may be prepared as clones in M13, plasmid or lambda vectors and/or prepared directly from genomic DNA or cDNA by PCR or other amplification methods. Samples may be prepared or dispensed in multi-well plates. About 100–1000 ng of DNA samples may be prepared in 2–500 ml of final volume.

The nucleic acids would then be fragmented by any of the methods known to those of skill in the art including, for example, using restriction enzymes as described at 9.24–9.28 of Sambrook et al. (1989), shearing by ultrasound and NaOH treatment.

Low pressure shearing is also appropriate, as described by Schriefer et al. (1990, incorporated herein by reference). In this method, DNA samples are passed through a small French pressure cell at a variety of low to intermediate pressures. A lever device allows controlled application of low to intermediate pressures to the cell. The results of these studies indicate that low-pressure shearing is a useful alternative to sonic and enzymatic DNA fragmentation methods.

One particularly suitable way for fragmenting DNA is contemplated to be that using the two base recognition endonuclease, CviJI, described by Fitzgerald et al. (1992). These authors described an approach for the rapid fragmentation and fractionation of DNA into particular sizes that they contemplated to be suitable for shotgun cloning and sequencing. The present inventor envisions that this will also be particularly useful for generating random, but relatively small, fragments of DNA for use in the present sequencing technology.

The restriction endonuclease CviJI normally cleaves the recognition sequence PuGCPy between the G and C to leave blunt ends. Atypical reaction conditions, which alter the specificity of this enzyme (CviJI), yield a quasi-random distribution of DNA fragments form the small molecule pUC19 (2688 base pairs). Fitzgerald et al. (1992) quantitatively evaluated the randomness of this fragmentation strategy, using a CviJI digest of pUC19 that was size fractionated by a rapid gel filtration method and directly ligated, without end repair, to a lac Z minus M13 cloning vector. Sequence analysis of 76 clones showed that CviJI** restricts pyGCPy and PuGCPu, in addition to PuGCPy sites, and that new sequence data is accumulated at a rate consistent with random fragmentation.

As reported in the literature, advantages of this approach compared to sonication and agarose gel fractionation include: smaller amounts of DNA are required (0.2–0.5 ug instead of 2–5 ug); and fewer steps are involved (no preligation, end repair, chemical extraction, or agarose gel electrophoresis and elution are needed). These advantages are also proposed to be of use when preparing DNA for sequencing by Format 3.

Irrespective of the manner in which the nucleic acid fragments are obtained or prepared, it is important to denature the DNA to give single stranded pieces available for hybridization. This is achieved by incubating the DNA solution for 2–5 minutes at 80–90° C. The solution is then cooled quickly to 2° C. to prevent renaturation of the DNA fragments before they are contacted with the chip. Phosphate groups must also be removed from genomic DNA by methods known in the art.

5.23 Preparation of DNA Arrays

Arrays may be prepared by spotting DNA samples on a support such as a nylon membrane. Spotting may be performed by using arrays of metal pins (the positions of which correspond to an array of wells in a microtiter plate) to repeated by transfer of about 20 nl of a DNA solution to a nylon membrane. By offset printing, a density of dots higher than the density of the wells is achieved. One to 25 dots may be accommodated in 1 mm$^2$, depending on the type of label used. By avoiding spotting in some preselected number of rows and columns, separate subsets (subarrays) may be formed. Samples in one subarray may be the same genomic segment of DNA (or the same gene) from different individuals, or may be different, overlapped genomic clones. Each of the subarrays may represent replica spotting of the same samples. In one example, a selected gene segment may be amplified from 64 patients. For each patient, the amplified gene segment may be in one 96-well plate (all 96 wells containing the same sample). A plate for each of the 64 patients is prepared. By using a 96-pin device, all samples may be spotted on one 8×12 cm membrane. Subarrays may contain 64 samples, one from each patient. Where the 96 subarrays are identical, the dot span may be 1 mm$^2$ and there may be a 1 mm space between subarrays.

Another approach is to use membranes or plates (available from NUNC, Naperville, Ill.) which may be partitioned by physical spacers e.g. a plastic grid molded over the membrane, the grid being similar to the sort of membrane applied to the bottom of multiwell plates, or hydrophobic strips. A fixed physical spacer is not preferred for imaging by exposure to flat phosphor-storage screens or x-ray films.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples. The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims.

All references cited within the body of the instant specification are hereby incorporated by reference in their entirety.

6.0 EXAMPLES

Example 1

Isolation of SEQ ID NO: 1–7 from a cDNA Libraries of Human Cells

A plurality of novel nucleic acids were obtained from a cDNA library prepared from human testis cells (Hyseq clone identification numbers 2880984 and 2881695), from human fetal skin (Hyseq clone identification number 15375176), adult spleen (Hyseq clone identification number 14856094), and human endothelial cells (Hyseq clone identification numbers 13804756, 13687487, 13804756) using standard PCR, sequencing by hybridization sequence signature analysis, and Sanger sequencing techniques. The inserts of the library were amplified with PCR using primers specific for vector sequences flanking the inserts. These samples were spotted onto nylon membranes and interrogated with oligonucleotide probes to give sequence signatures. The clones were clustered into groups of similar or identical sequences, and single representative clones were selected from each group for gel sequencing. The 5' sequence of the amplified inserts was then deduced using the reverse M13 sequencing primer in a typical Sanger sequencing protocol. PCR products were purified and subjected to fluorescent dye terminator cycle sequencing. Single-pass gel sequencing was done using a 377 Applied Biosystems (ABI) sequencer. These inserts was identified as a novel sequence not previously obtained from this library and not previously reported in public databases. These sequences are designated as SEQ ID NO: 1–7 in the attached sequence listing.

Example 2

Assemblage of SEQ ID NO: 8 and 9

The novel nucleic acids (SEQ ID NO: 8 and 9) of the invention were assembled from sequences that were obtained from a cDNA library by methods described in Example 1 above, and in some cases sequences obtained from one or more public databases. The sequence was assembled using an EST sequence (SEQ ID NO: 2) as a seed. Then a recursive algorithm was used to extend the seed EST into an extended assemblage, by pulling additional sequences from different databases (i.e., Hyseq's database containing EST sequences, dbEST version 114, gb pri 114, and UniGene version 101) that belong to this assemblage. The algorithm terminated when there was no additional sequences from the above databases that would extend the assemblage. Inclusion of component sequences into the assemblage was based on a BLASTN hit to the extending assemblage with BLAST score greater than 300 and percent identity greater than 95%. SEQ ID NO: 8 was further manually edited to obtain SEQ ID NO: 9. FIG. 1 shows the alignment of SEQ ID NO. 9 with SEQ ID NO. 1–7.

The nearest neighbor result for the assembled sequence (SEQ ID NO. 8) was obtained by a FASTA version 3 search against Genpept release 114, using Fastxy algorithm. Fastxy is an improved version of FASTA alignment which allows in-codon frame shifts. The nearest neighbor result showed the closest homologue for each assemblage from Genpept (and contains the translated amino acid sequences for which the assemblage encodes). The nearest neighbor results is set forth below:

| Accession No. | Description | Smith-Waterman Score | % Identity |
|---|---|---|---|
| AB016768 | Mus musculus thrombospondin type 1 domain | 56 | 43.750 |

The predicted amino acid sequence for SEQ ID NO: 8 was obtained by using a software program called FASTY (available at the University of Virginia web site) which selects a polypeptide based on a comparison of translated novel polynucleotide to known polynucleotides (W. R. Pearson, Methods in Enzymology, 183:63–98 (1990), incorporated herein by reference).
For SEQ ID NO: 8:

```
For SEQ ID NO:8:
Predicted      Predicted      Amino acid segment containing signal peptide
beginning      end            (A = Alanine, C = Cysteine, D = Aspartic Acid,
nucleotide     nucleotide     E = Glutamic Acid, F = Phenylalanine,
location       location       G = Glycine, H = Histidine, I = Isoleucine,
corresponding  corresponding  K = Lysine, L = Leucine, M = Methionine,
to first       to first       N = Asparagine, P = Proline, Q = Glutamine,
amino acid     amino acid     R = Arginine, S= Serine, T = Threonine,
residue of     residue of     V = Valine, W = Tryptophan, Y = Tyrosine,
amino acid     amino acid     X = Unknown, * = Stop Codon, /= possible
sequence       sequence       nucleotide deletion, \= possible nucleotide
                              insertion)
575            1054           C T K C K A D C D T C F N K N F C T K C K S G F Y
                              L H L G K C L D N C P E G L E A N N H T M E C V S
                              I V H C E V S E W N P W S P C T K K G K T C G F K
                              R G T E T R V R E I I Q H P S A K G N L C P P T N E
                              T R K C T V Q R K K C Q K G E R G K K G R E R K R
                              K K P N K G E S K E A I P D S K S L E S S K E I P E Q
                              R E N K Q Q Q
                              (SEQ ID NO: 14)
```

Example 3

Assemblage of SEO ID NO: 10

A polypeptide (SEQ ID NO: 10) was predicted to be encoded by SEQ ID NO: 9 as set forth below. The polypeptide was predicted using a software program called BLASTX which selects a polypeptide based on a comparison of translated novel polynucleotide to known polynucleotides. The initial methionine starts at position 291 of SEQ ID NO: 9 and the putative stop codon, TAG, begins at position 1107 of the nucleotide sequence.

Example 4

Cloning of Stem Cell Growth Factor-like Gene; and Expression and Purification of Stem Cell Growth Factor-Like Protein Stem cell growth factor-like polynucleotide (SEQ ID NO: 11 or 12) was cloned by PCR into pIB/V5-His TOPO TA cloning vector (Invitrogen) from Hyseq's full-length stem cell growth factor-like clone. Stem cell growth factor-like gene was further subcloned into pcDNA3.1-Myc-His vectors (Invitrogen) and expressed with or without V5-His tag. Insect cells (high Five, Invitrogen) were transfected with stem cell growth factor-like gene with the His-5 tag by using the InsectSelect system (Invitrogen) using manufacturer's suggested protocols. Stem cell growth factor-like protein was purified from the cell media by a combination of pH adjustment, cation exchange chromatography, and affinity chromatography as described below. Briefly, the pH of the medium was adjusted to 7.0 and the protease inhibitors PMSF and EDTA were added. Column chromatography purification was performed on Pharmacia Akta instrument system at room temperature using sequential removal of contaminants on appropriately sized columns of SP-Sepharose Fast Flow, Hitrap heparin Sepharose, and Ni-NTA resins. Column elution fractions were analyzed by separation on 16% SDS-PAGE gels, transfer to Immobilin membranes (Millipore), and detection of the tagged protein by anti-V5 antibody using manufacturer's protocols. Fractions containing stem cell growth factor-like activity eluted from Ni-NTA column were pooled and equilibrated with PBS and stored at −80° C. until analyzed for stem cell growth factor-like activity.

Example 5

Expression of Stem Cell Growth Factor-like Protein in Primary Human Cells

The product of the secondary nested PCR from Marathon spleen library (SEQ ID NO: 11 or 12) or any other polynucleotide encoding stem cell growth factor-like polypeptide were cloned into MSCV retroviral vector (Clontech) into suitable cloning sites using appropriate forward and reverse PCR primers. This retroviral vectorwas then transfected using FUGENE-6 transfection reagent into packaging cell lines to produce suitably large quantities of retrovirus that will have the stem cell growth factor-like DNA cloned in it. Retrovirus containing supernatants were prepared from packaged cell lines and mixed with stromal or stem cells. Upon retrovirus transduction these transduced cells may express the stem cell growth factor-like protein.

Example 6

Assay for Growth and Differentiation of Stem Cells Using Coculture Assay $1 \times 10^4$ mouse stem cells were co-cultured with $1 \times 10^4$ stem cell growth factor-like polynucleotide-transduced stromal cells or vector-transduced stromal cells (produced by Example 5) in the serum-free medium. On day seven, IL-3 (10 ng/ml) and IL-6 (10 ng/ml) were added as additional growth factors. Cultures were monitored microscopically every day. After appropriate further incubation, cells were harvested, and counted using hemacytometer. Results from one experiment are presented in the table below:

| Conditions | Day 15 (approximate number of cell/ml) | Day 18 (approximate number of cell/ml) |
|---|---|---|
| Vector-transduced stroma cells + stem cells | 30000 | 105000 |
| Stem cell growth factor polynucleotide-transduced stroma cells + stem cells | 405000 | 825000 |

Example 7

Assay for Proliferation and Differentiation of Stem Cells

CD34$^+$ hematopoietic stem cells (HSC) were purified from mobilized peripheral blood (purchased from ALLCells). CD34$^+$ cells were purified by positively selecting cells using Miltenyi breads (Miltenyi). Stem cells were plated in 96-well plates at 103/well. Purified stem cell growth factor-like protein and other hematopoietic cytokines (purchased from R & D systems), and the combinations thereof were added to the cultures for assessing the stem cell growth factor activity. The growth and differentiation of stem cells were examined 5 days after culture by light microscope. The results of six experiments are shown in the table below, wherein positive effect of stem cell growth factor protein was observed in three out of six experiments. Abbreviations: Stem cell growth factor-like protein=SCGF; Interleukin-3=IL-3; thrombopoietin=TPO; Fms-like tyrosine kinase-3 ligand=flt-3 ligand (+) indicates growth and/or differentiation of stem cells; (−) indicates no growth or differentiation and loss of viability of stem cells.

| Growth factor(s) added | Growth and morphological changes Experiment 1 | Growth and morphological changes Experiment 2 |
|---|---|---|
| None | (−) | (−) |
| Stem cell growth factor (50 ng/ml) | (−) | (−) |
| IL-3 (10 ng/ml) | (+/−) | (+) |
| SCGF (50 ng/ml) + IL-3 (10 ng/ml) | (+) | (+) |

| Growth factor(s) added | Growth and morphological changes Experiment 3 | Growth and morphological changes Experiment 4 | Growth and morphological changes Experiment 5 |
|---|---|---|---|
| None | (−) | (−) | (−) |
| Stem cell growth factor (50 ng/ml) | (−) | (−) | (−) |
| TPO (100 ng/ml) | (−) | (−) | (−) |
| kit ligand (50 ng/ml) + flt-3 ligand (50 ng/ml) | (−) | (−) | (−) |
| kit ligand (50 ng/ml) + flt-3 ligand (50 ng/ml) + SCGF (50 ng/ml) | (+) | (−) | (−) |

| Growth factor(s) added | Growth and morphological changes Experiment 6 |
|---|---|
| None | (−) |
| Stem cell growth factor (50 ng/ml) | (−) |
| kit ligand (50 ng/ml) | (−) |
| flt-3 ligand (50 ng/ml) | (−) |
| kit ligand (50 ng/ml) + flt-3 ligand (50 ng/ml) | (−) |
| kit ligand (50 ng/ml) + flt-3 ligand (50 ng/ml) + SCGF (50 ng/ml) | (+) |

Example 8

Establishment of Stromal Cell Strain Derived from Mouse AGM (1) Isolation of AGM Region from Fetal Mouse C3H/HeNSLc mouse of both genders (purchased from Japan SLC INC.) was bred under a SPF (specific pathogen-free) circumstance. One or two female mice and one male mouse were reared in the same cage over a night. In the next morning, the female mice in which the existence of a vaginal plug was confirmed were transferred to other cages and breeded. The day when the existence of the vaginal plug was confirmed was defined to be the 0.5th day of pregnancy. On the 10.5th day of the pregnancy, after mouse was sacrificed by cervical dislocation, fetuses were extirpated. Isolation of AGM regions was performed according to the method by Godin et al. (Godin, I., Proc. Natl. Acad. Sci. U.S.A., 92: 773–777, 1995) and the method by Medvinsky et al. (Medvinsky, A. L., Blood, 87: 557–565, 1996). The fetuses were placed in a culture dishes to which PBS(−) (phosphate buffered saline) (produced by Nissui Seiyaku) was added in a volume just sufficient to cover them. After the AGM regions were carefully excised so as not to include other regions under a stereoscopic microscope, they were put in another 24-well culture dish (Nunc).

(2) Establishment of Cell Lines Derived from AGM

One drop of MEM medium (Sigma) containing 10% FCS (Hyclone) was added to the AGM regions in the 24-well culture dish (Nunc), and AGM regions were cultured in incubator overnight. The cultures were performed in the MEM medium (Sigma) including 10% FCS (Hyclone) at 37° C., in an atmosphere of 5% $CO_2$, and at a humidity of 100%. When the cells corresponding to the AGM regions adhered to the culture dish due to overnight cultivation, two milliliters of MEM medium containing 10% FCS was further added. Stromal cells began to appear around the AGM region tissue fragment after the continuous cultivation. After one-week cultivation, adhesive cells were trypsinized (0.05% trypsin in PBS containing 0.53 mM EDTA (Gibco BRL) at 37° C. for three to five minutes) and dispersed. The stromal cells were then washed twice with the medium, and seeded on 6-well culture dish (Nunc). On the next day, the cells which did not adhered to the culture dish and the medium were removed, and then, fresh medium were added. Two weeks after transfer, the cells in the 6-well culture dish were γ-ray irradiated at 900 Rad to eliminate endogenous hematopoietic cells. Although attempts of the direct cell cloning by limiting dilution from this culture system was failed, so that no cell proliferation was observed. Then, attempts were made according to as follows: after adaptation of cells so as to be able to proliferate from a small number of cells by increasing the number of seeded cells in one well, the cells were cloned by limiting dilution.

That is, the AGM was extirpated and cultured in the same manner as described above. The culture system two weeks after the γ-ray radiation was trypsinized (0.05% trypsin in PBS containing 0.53 mM EDTA at 37° C. for three to five minutes) and the cells were suspended, so that the cells were seeded in a 24-well culture dish ranging from 50 to 100 cells/well. After the culture was continued for three weeks, the cells were seeded in a 96-well culture dish (Nunc) by means of limiting dilution so as to be 0.3 cells/well. The cells which were derived from the well seeded only one cell and proliferated were allowed to enlarge culture. As a result, the cells were successfully cloned to obtain fibroblast like cells and cobble stone like cells.

CD34 positive cell fraction derived from the human cord blood was co-cultured with the fibroblast like cells for two weeks. Colony forming cells could not be found in the co-culture system with the fibroblast like cells. Then, the similar examination was performed for seven cell clones showing cobble stone like morphotype. Three clones having activity to proliferate and support the human hematopoietic stem cells were obtained and were named AGM-s1, AGM-s2, and AGM-s3.

Example 9

Preparation of Hematopoietic Stem Cells from Mouse Bone Marrow

The bone marrow was collected from the femur of C57BL/6-Ly5.1 pep (week ages ranging from eight to ten, and male) (the gift from Professor K. Nakauchi, University of Tsukuba), and suspended in PBS. After the mouse bone marrow mononuclear cells were concentrated by specific gravity centrifugation according to the usual method (S. Kouzu, Fundamental techniques for immunology, YODOSHA, 1995), the cells were suspended with staining buffer (PBS containing 5% FCS and 0.05% NaN$_3$).

The most immature hematopoietic stem cell fraction was obtained as follows (Osawa, M. et al., Science 273: 242–245, 1996).

The mononuclear cells were incubated with biotylated anti-lineage monoclonal antibodies (CD45R, CD4, CD8, Gr-1, Ter119, and CD11c, purchased from Pharmingen), fluorescein isothiocyanate (FITC)-anti-CD34, phycoerythrin (PE)-anti-Sca-1, and allophycocyanin (APC)-anti-c-Kit for 20 min on ice. After the stained cells were washed twice with staining buffer, CD34 negative, Sca-1 positive, c-Kit positive, and Lin negative cells were isolated on a FACS Vantage (Becton Dickinson).

Example 10

Subcloning of Mouse Stromal Cell Strain and Assessment of an Activity to Support the Hematopoietic Stem Cells of a Variety of Cell Strains (1) Subcloning of Mouse Stromal Cell Strain
1) Isolation of AGM-s3 Subclone Stromal cell strain AGM-s3 derived from AGM was subcultured in MEMα medium (GIBCO BRL), including non-active 10% FCS (bovine fetal serum, Hyclone) and was suspended in PBS containing 5% FCS (PBS-FCS). Clone sorting was performed in a 96-well culture dish (Falcon) at one cell/well using a cell sorter (FACS Vantage; Becton Dickinson). Among cells in the 96 wells, cultures of the cells which proliferated were expanded, so that thirteen kinds of AGM-s3 subclones were obtained. The activity to support the hematopoietic cells of these AGM-s3 subclones was assessed.

2) Isolation of Human Cord Blood CD34 Positive Stem Cell

The human cord blood was collected at normal delivery according to the criteria approved by Drug Discovery Institute, Ethics committee, Kirin Brewery Co., LTD. The cord blood was collected using a syringe added with heparin so as not to coagulate. The heparin treated cord blood was overlaid on Lymphoprep (NYCOMED PHARMA), and mononuclear cells were separated by centrifugation (at 400 G, at room temperature, and for 30 minutes). Erythrocytes contaminated in the mononuclear cell fraction were lyzed by treatment with ammonium chloride buffer solution (0.83% NH$_4$Cl-Tris HCl, 20 mM, pH 6.8) at room temperature for two minutes. After the mononuclear cells were washed with PBS-FCS, ten milligrams of human IgG was added and allowed to stand on ice for ten minutes. Then, the cells were further washed with PBS-FCS, added with biotinylated antibodies against the antigens specific to the human differentiated blood cells that is, CD2, CD11c (purified from ATCC hybridoma), CD19 (Pharmingen), CD15, and CD41 (Leinco Technologies Inc.), and the antibody against Glycophorin A (Cosmo Bio), and allowed to stand on ice for 20 min. After washing with PBS-FCS, the cells were suspended in one milliliter of PBS containing 5% FCS, 10 mM EDTA, and 0.05% NaN$_3$ (PBS-FCS-EDTA-NaN$_3$), added with magnetic beads bound with streptavidin (BioMag. Per Septive Diagnostics), and allowed to stand on ice for 40 min. The differentiated blood cells which expressed differentiation antigens were removed using a magnetic separator (Dynal MPC-1 Dynal). FITC labeled CD34 antibody (Immunotech S.A., Marseilles, France) were added to the remaining differentiated blood cell antigen negative cell fraction. After incubation on ice for 20 min., CD34 positive fraction was recovered using a cell sorter. This cell fraction was defined as a hematopoietic stem cell fraction derived from the human cord blood.

3) Co-culture of the Human Hematopoietic Stem Cells and AGM-s3 Subclone

After 13 kinds of AGM-s3 subclones or stromal cell strain MS-5 derived from the mouse bone marrow were seeded in a 24-well culture dish (Falcon) at 1×10$^4$ cells/well, and cells were cultured in one milliliter of MEMα medium containing 10% FCS until the cells covered all over the bottom surfaces of the wells. CD34 positive hematopoietic stem cells derived from the human cord blood were sorted on the above described stromal cells at 500 cells/well, and co-cultured in one milliliter of MEMα medium containing 10% FCS. One week after the initiation of the co-culture, one milliliter of the same medium was further added. Two weeks after the initiation of the co-culture, the stromal cells and the human blood cells were trypsinized (0.05% trypsin in PBS containing 0.5 mM EDTA (GIBCO BRL) at 37° C. and standing for two to five min.) and dispersed from the culture dish. Activities to support the hematopoietic stem cells were assessed with a colony assay.

4) Assessment of Proliferation Statuses of the Hematopoietic Stem Cells and Hemopoietic Precursor Cells by Clonogenic Assay The cells which proliferated in the above described co-culture system were appropriately diluted, added to one milliliter of methylcellulose culture system, and analyzed in triplicate. The analysis using the methylcellulose culture system were performed using a 6-well culture dish (Falcon) in the presence of 10 ng/ml of human SCF, human IL-3, human IL-6, human G-CSF, human TPO, and EPO at 2 IU/ml to MethoCult H4230 (Stem Cell Technologies Inc.). All of a variety of the above described hematopoietic factors were recombinants and pure. Two weeks after the culture, developed colonies were observed under a microscope and counted numbers of CFU-GM (granulocyte-macrophage differentiating series), BFU-E (erythroid burst forming unit), and CFU-E mix (erythrocyte mixed differentiating series).

Figure 4:
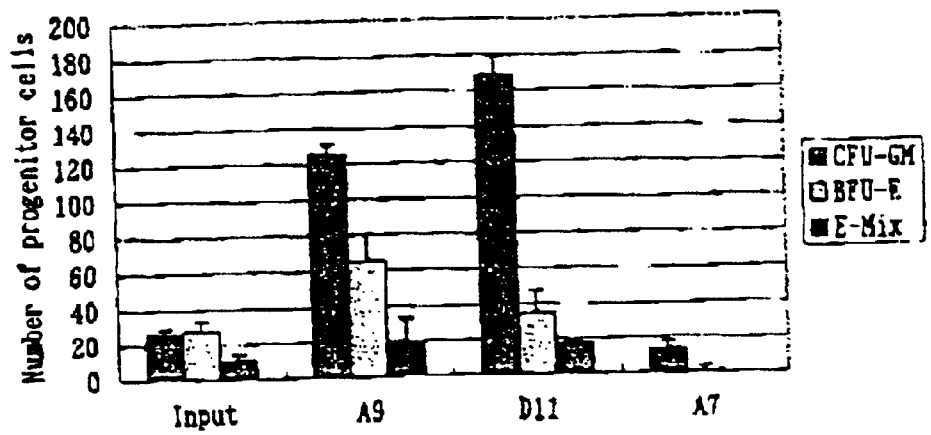
FIG. 4 shows proliferation statuses of hematopoietic stem cells and hematopoietic progenitor cells determined by a clonogenic assay after co-culture of CD34 positive hematopoietic stem cells with AGM-s3 subclone A9, A7, or D11 cells for two weeks.

FIG. 4 shows the results from two-week co-culture of the CD34 positive hematopoietic stem cells and AGM-s3 subclones A9, A7, or D11. As a result of the co-culture, A9 and D11 subclones among 13 kinds of AGM-s3 subclones supported proliferation of all three lineages of CFU-GM, BFU-E, and CFU-E mix. Especially, although BFU-E and CFU-E mix, that is, the precursor cells of an erythrocytes were hardly to be supported in usual, they proliferated in the co-culture system with A9 or D11 cells. The results showed that proliferation or maintenance of the hematopoietic stem cells or the hemopoietic precursor cells occurred in the co-culture with A9 or D11 cells and the precursor cells of the erythrocyte were continuously supplied. In contrast, although cellular morphology of A7 was similar to that of A9, A7 did not support CFU-GM, BFU-E, and CFU-E mix.

Figure 5:
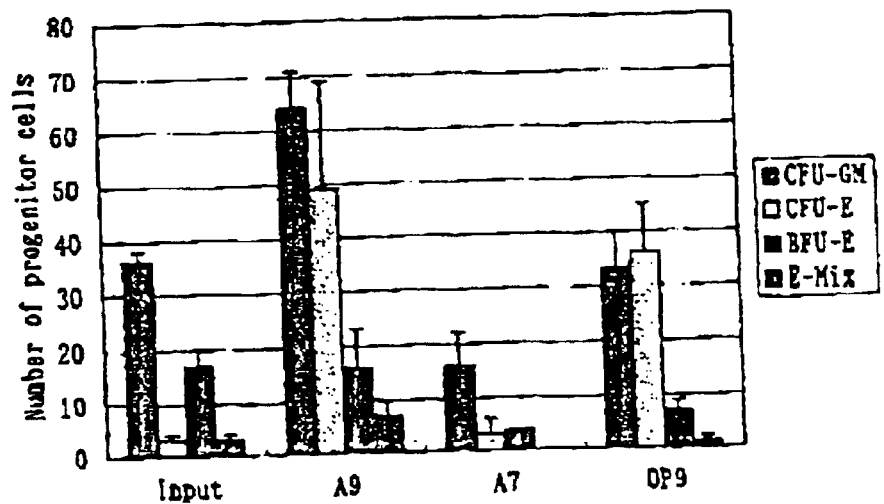
FIG. 5 shows proliferation statuses of hematopoietic stem cells and hematopoietic progenitor cells determined by a clonogenic assay after co-culture of CD34 positive hematopoietic stem cells with AGM-s3 subclone A9, A7, or OP9 cells for two weeks.

5) Comparison of an Activity to Support the Human Hematopoietic Stem Cells Between A9 and a Stromal Cell Strain OP9 Derived from Mouse Fetus Comparison of activities to support the CD34 positive hematopoietic stem cells derived from the human cord blood between AGM-s3 subclones A9 and A7, and a stromal cell line OP9 derived from mouse fetus were performed with CFU-GM, BFU-E, CFU-E and CFU-E mix as indexes using the above described method. FIG. 5 shows the results from the two-week co-culture. In the A7 cell culture system, CFU-GM, BFU-E, and CFU-E were significantly decreased and CFU-E mix was completely disappeared. In contrast, with OP9 cells, a variety of blood cell precursor cells including CFU-E mix were supported, although the supporting ability was less than that of A9 cells. Therefore, OP9 cells were clear to possess the activity to support the hematopoietic stem cells.

(2) Assessment of Activities to Support the Hematopoietic Stem Cells in a Variety of Cell Strains The above described stromal cell lines(AGM-s3-A9, AGM-s3-A7, and AGM-s3-G1), 3T3Swiss (ATCC), OP9 (RCB1124, RIKEN Cell Development Bank), and NIH3T3 (ATCC) were seeded in a 24-well culture dish (Falcon) at $5 \times 10^4$ cells/well. The cell lines were cultured in MEMα medium (GIBCO BRL) containing non-active 10% FCS (bovine fetal serum, Hyclone) for one day and allowed to proliferated until the cells covered all over the bottom surfaces of the wells. Then, the medium was replaced to one milliliter of fresh medium, thirty cells of the mouse hematopoietic stem cells (derived from C57BL/6-Ly5.1) obtained in Example 9 were sorted on this cell layer, and co-culture was initiated.

On seventh day of the cultivation, the cells were trypsinized (0.05% trypsin in PBS containing 0.5 mM EDTA (GIBCO BRL) at 37° C. for two to five minutes) and dispersed and all the cells on the culture dish were recovered. The recovered whole cells of each cell line and whole bone marrow cells at 200,000 cells (derived from C57BL/6-Ly5.2 mouse, Charles River) were transplanted into the C57BL/6-Ly5.2 mice (eight weeks age and male, Charles River) irradiated with X-ray at 8.5 Gy through the tail vein. After the transplantation, the peripheral blood was collected from the retro-orbital sinus at intervals, and calculated the ratio of a cell number derived from the C57BL/6-Ly5.1 prep mouse with FACS. The peripheral blood was analyzed according to the usual method (S. Kouzu, Fundamental techniques for immunology, YODOSHA, 1995). Three hundreds and fifty μL of distilled water was added to 50 μL of the peripheral blood, allowed to stand for 30 sec. so as to lyze the erythrocytes. Then, PBS at twice concentrations was added and centrifuged, so that the white blood cells were recovered. After the cells were washed once using the staining buffer (PBS containing 5% FCS and 0.05% $NaN_3$), anti-CD16 antibody, Ly5.1 (CD45.1) antibody labeled with FITC, Gr-1 and CD11c antibodies labeled with phycoerythrin, and CD45R (B220) antibody and CD90 (Thy 1) antibody labeled with allophycocyanin (all of these were purchased from Pharmingen) were added. After these cells were allowed to stand for reaction in the ice bath for 30 min., they were washed with the staining buffer and FACS analysis was performed.

Expansion in the number of cells capable of reconstitution during the hematopoietic stem cell culture was assessed by calculating the proportions of Ly5.1 positive cells in the Gr-1 or CD11c positive cells (myeloid cells) or Ly5.1 positive cells in the CD90 or CD45R positive cells (lymphoid cells) in the peripheral blood at intervals post transplantation.

FIG. 6 shows the results. When the cells were co-cultured with AGM-s3-A9, OP9, and 3T3Swiss cells, high chimerism of donor cells were maintained after the transplantation. Therefore, these stromal cells were considered to have a high activity to support the hematopoietic stem cells. In contrast, when the cells were co-cultured with AGM-s3-A7, AGM-s3-G1, and NIH3T3 cells, high chimerism were not observed in the transplanted cells. Therefore, these stromal cells had low. activity to support the hematopoietic stem cells or the hemopoietic progenitor cells.

Example 11

Isolation of Mouse SCR-1 Fragment

Total RNA was prepared from AGM-s3-A9 cells at $1.4 \times 10^8$ cells dissolved in 20 mL of ISOGEN (Nippon gene, Japan) according to the attachment. Messenger RNA was purified from one milligram of the total RNA according to the protocol of the mRNA purification kit (Amersham Pharmacia, U.S.A.). cDNA was synthesized from this mRNA by oligo-dT primed with SuperScript Plasmid System (GIBCO Lifetech, U.S.A.) and inserted into pSPORT1 (GIBCO Lifetech, U.S.A.). An AGM-s3-A9 cell specific cDNA clone was obtained from this library with SBH method (Hyseq, U.S.A.). A nucleotide sequence of the clone was determined using ABI377 DNA sequencer (Perkin Elmer, U.S.A.). The obtained sequence was analyzed by homology search, so that the gene was identified as a novel gene SCR-1. The nucleotide sequence obtained was nucleotide numbers 1032 to 1484 of SEQ ID NO: 31.

Example 12

Whole Cloning of Mouse SCR-1

Total RNA was prepared from AGM-s3-A9 cells at $1.4 \times 10^8$ cells dissolved in 20 mL of ISOGEN (Nippon gene, Japan) according to the attachment. Messenger RNA was purified from one milligram of the total RNA according to the protocol of the mRNA purification kit (Amersham Pharmacia, U.S.A.). cDNA library was constructed from 2 mg of prepared mRNA using SMART cDNA library construction kit (CLONTECH, U.S.A.) according to the attachment. This library included about 400,000 kinds of independent clones in total and divided into 15 fractions. The fraction containing SCR-1 cDNA clone was identified by PCR using the following conditions.

The following primers were synthesized based on the gene fragment sequence obtained in Example 11 PCR at 35 cycles was performed using each fraction of AGM-s3-A9 cDNA library as a template, one cycle being a step performed at 94° C. for 30 seconds, at 55° C. for 30 seconds, and 72° C. for one minute.

SCR-1F1: AGTACAAAGAAAGAAGTGTTC (SEQ ID NO: 35)

SCR-1R1: TGAGTCTACAGTAACCTCGCA (SEQ ID NO: 36)

The PCR products were subjected to a 2% agarose gel electrophoresis, and the fraction in which a PCR product had an expected size was identified. Two positive fractions were seeded on petri dishes at a diameter of 15 cm at 50,000 plaque, each fractions being seeded on two petri dishes. After incubating the dishes at 37° C. for 10 hours, each plaque was transferred to a Biodyne nylon filter (Pall, U.S.A.). DNAs on the nylon filters were immobilized according to the attachment. Screening was performed using a $^{32}$P labeled DNA probe.

The probe was prepared as follows. PCR at 35 cycles was performed using SCR-1R1 and T7 primer (TAATACGACTCACTATAGGG) (SEQ ID NO: 37), and a plasmid including the gene fragment obtained in Example 11 as a template, one cycle being a step performed at 94° C. for 30 seconds, at 55° C. for 30 seconds, and 72° C. for one minute. The PCR products were subjected to a 2% agarose gel electrophoresis, and the amplified fragment was purified using JETSORB (GENOMED Ger.). $^{32}$P labeled DNA probe was prepared using Megaprime labeling kit (Amersham Pharmacia U.S.A.) and 25 ng of purified PCR fragment as a template.

Hybridization using ExpressHybSolution (CLONTECH, U.S.A.) and washing were performed according to the attachment. X-ray films (Fuji Photo Film Co. Ltd., Japan) were exposed to the hybridized nylon filters for one day and developed using a Fuji film auto-developer apparatus. Based on the analyzed results, the plaque which corresponded to the spot strongly exposed was scratched from the petri dish. The plaque was again seeded on a petri dish at a diameter of 10 cm so as to generate about 200 plaques. Screening was performed again according to the method described above, so that a single plaque was isolated. The obtained phage clone was introduced into E. coli BM25.8 strain according to the attachment of the SMART cDNA library constructing kit, so that it was excised in vivo in E. coli BM25.8 strain. The infected E. coli was cultured on LB agar medium added with 50 mg/mL of ampicillin until colonies were formed. A single colony was seeded in three milliliters of LB medium containing 50 mg/mL of ampicillin and cultured overnight at 30° C. About 10 mg of plasmid was purified from the cultured cells using RPM Kit (BIO101, U.S.A.). The sequence of the both ends of the inserted fragment was determined using λTriplEx5'LD-Insert Screening Amplimer (CTCGGGAAGCGCGCCATTGTGTTGGT: CLONTECH, U.S.A; SEQ ID NO: 30.) by ABI377 DNA sequencer. The clone was found to include cDNA which has a nucleotide sequence beginning from 1 in SEQ ID NO: 31. After the whole nucleotide sequence of the inserted cDNA was determined using ABI377 DNA sequencer, the nucleotide sequence of SEQ ID NO: 31 was confirmed. Amino acid sequences predicted from the above nucleotide sequence were shown in SEQ ID NO: 31 and SEQ ID NO: 32.

The plasmid including DNA with the nucleotide sequence of SEQ ID NO: 31 has been internationally deposited in National Institute of Bioscience and Human-Technology, Agency of Industrial Science and Technology (Zip code 305-8566; Higashi 1-1-3, Tsukuba, Ibaraki, Japan) on Jun. 26, 2000, and the registered number was given to be FERM BP-7198.

Example 13

Cloning of Human SCR-1

Based on the nucleotide sequence of mouse SCR-1, the database of GenBank (NCBI, U.S.A.) was searched using Blast. A homologous nucleotide sequence with mouse SCR-1 was found (Accession Nos. AI872133 and AW316562). The following primers were synthesized using this sequence derived from human.

h782F1: TCGCGGCGATGCCAGCCACCCCAG (SEQ ID NO: 38)

h782F2: AGCACGCCTATCGGATGTGAGAG GAGAAGT (SEQ ID NO: 39)

h782R1: CTATTAACAAATATATTTATTGTGG TGGCT (SEQ ID NO: 40)

h782R2: TGGTGGCTTTCTCCCCTACTAGAT ATACCT (SEQ ID NO: 41)

cDNA was synthesized from 3 μg of mRNA derived from the placenta and the skeletal muscle (CLONTECH, U.S.A.) using oligo-dT primer and reverse transcriptase (SuperscriptII, GIBCO-BRL). PCR was performed using this cDNA as a template; h782F1, h782F2, h782R1, or h782R2 as a primer; and Platinum Pfx DNA Polymerase (GIBCO Lifetech, U.S.A.). As a result, an amplified fragment was obtained from each organ. Among them, the PCR fragment derived from the placenta was ligated to pCR-Blunt vector (Invitrogen, U.S.A.), and the gene was introduced into E. coli DH5a. Then, the transferred E. coli was seeded on LB agar medium containing 100 mg/ml of ampicillin, so that colonies were formed. Each of isolated 16 colonies was added to 10 ml of PCR reaction solution, and treated at 94° C. for five minutes. Then, PCR at 35 cycles was performed, one cycle being a step performed at 94° C. for 30 seconds, at 55° C. for 30 seconds, and 72° C. for one minute. T7 primer or SP6 primer (GATTTTAGGTGACACTATAG) (SEQ ID NO: 42) was used as a primer at a final concentration of 0.2 mM. The PCR products were subjected to a 2% agarose gel electrophoresis. After the amplified fragment was confirmed, sequences of the three confirmed fragments were determined using ABI377 DNA sequencer. A nucleotide sequence of the obtained cDNA (SEQ ID NO: 33) was confirmed to be a human orthologous to that of mouse SCR-1.

The plasmid including DNA with the nucleotide sequence of SEQ ID NO: 33 as been internationally deposited in National Institute of Bioscience and Human-Technology, Agency of Industrial Science and Technology (Zip code 305-8566; Higashi 1-1-3, Tsukuba, Ibaraki, Japan) on Jun. 26, 2000, and the registered number was given to be FERM BP-7197.

With respect to mouse SCR-1 and human SCR-1, when the established database was searched, a human gene sequence having unknown function was found (WO98/49302). The homology of coding regions of these genes is shown in Table 1. The comparison of the homology was performed using a homology search function of DNAIS-Mac version 3.7 and calculating with the default settings of the software (nucleic acid Mode: Normal, Range: All (1–819 base), Cutoff: 45, Ktup: 4, amino acid Range: All (1–273 a.a.), Cutoff: 45, Ktup: 2). In this method, since only high homologous regions are used for calculation, low homologous regions, locating at an end, are excluded for calculation.

TABLE 1

|  | Mouse SCR-1 | Gene having unknown function |
|---|---|---|
| Human SCR-1 | 88.5 | 98.5 |
|  | (87.1) | (100) |
| Mouse SCR-1 |  | 87.2 |
|  |  | (85.1) |

The upper numbers show the homology in nucleotide level. The lower numbers (parenthesize) show the homology in amino acid level.

Human SCR-1 and the gene having unknown function had the same nucleotides from the initiation codon to the first nucleotide of the 266th codon (nucleotide number 1054 in SEQ ID NO: 33) in the coding region. However, the down stream sequences thereof were not identical. The nucleotide sequence and the amino acid sequence of this nonidentical region in this gene having unknown function were shown in SEQ ID NO: 45 and SEQ ID NO: 46, respectively. The first nucleotide in SEQ ID NO: 45 corresponded to the nucleotide number 1054 in SEQ ID NO: 33, and these were identical. One nucleotide was nonidentical at the position corresponding to the 567th nucleotide in SEQ ID NO: 33 in both genes.

Example 14

Study of the Expression Region of SCR-1

Northern blot analysis was performed using probes used in Example 13. Hybridization was performed with respect to Northern blots of Human MTN Blot I, II, III, Immune System II, Mouse MTN Blot (CLONTECH, U.S.A.). The hybridization was performed using ExpressHyb Hybridization Solution (CLONTECH, U.S.A.) according to the supplier's instruct ion. After prehybridization at 68° C. for two hours, a labeled probe was added. Hybridization was further performed at 68° C. for 18 hours. Washing of the filter was performed at room temperature in 2×SSC, 0.05% SDS solution for 30 min and repeated once. Further washing was performed at 50° C., in 0.1×SSC, 0.1% SDS solution for 30 min twice. Analysis of the hybridization was performed by exposure to an imaging plate (Fuji Photo film Co. Ltd., Japan) for three hours using a bioimaging analyzer BAS2000 (Fuji Photo Film Co., Ltd., Japan). Northern blot technique analysis was performed using probes used in Example 13 and MTN blot (CLONTECH, U.S.A.), so that the expression thereof in human was examined. As a result, the expression of mRNA at about 2.6 kb was confirmed in many organs including the liver, the placenta, the skeletal muscle, and the uterus. In mouse, the expression of mRNA at about 2.6 kb was confirmed in similar organs.

Example 15

Expression of Mouse SCR-1 in Stromal Cell
(1) Construction of Retrovirus Vector for Expression of Mouse SCR-1

Only ORF sequence in SCR-1 gene (a nucleotide sequence from nucleotides numbers 511 to 1350 in SEQ ID NO: 31) was inserted into a retrovirus vector, so that a vector for expression in stromal cells was constructed.

Messenger RNA was purified from one milligram of the total RNA in AGM-s3-A9 cell according to the protocol of the mRNA purification kit (Amersham Pharmacia, U.S.A.). cDNA was synthesized from this mRNA according to the conventional method. The following primers were synthesized and PCR at 30 cycles was performed using the above described cDNA as a template and Platinum Pfx DNA Polymerase (GIBCO Lifetech, U.S.A.), one cycle being a step performed at 94° C. for 20 seconds, at 55° C. for 30 seconds, and 68° C. for one minute.

m782F2: CCGCTCGAGCCACCATGCACTT
GCGACTGATTTC (SEQ ID NO: 43)

m782R2: ATTGAATTCCTAGTGTACAGTGC
TGACTG (SEQ ID NO: 44)

An amplified fragment was digested with restriction enzymes EcoRI and XhoI. After electrophoresis, a DNA fragment was purified using JETSORB (Genomed, Germany). The purified DNA fragment was ligated with pMX-IRES-GFP vector digested with EcoRI and XhoI (gift from Professor T. Kitamura, TOKYO UNIV. INST. OF MEDICAL SCIENCE, Japan). The pMX-IRES-GFP vector was a plasmid in which IRES GFP was inserted into the retrovirus vector pMX. The obtained recombinant vector was transferred into E. coli DH5a, and was seeded on LB agar medium containing 100 mg/ml of ampicillin, so that independent colonies were formed. After the isolated colony was cultured in 100 mL of LB medium containing 100 mg/ml of ampicillin, plasmid was purified using QIAGEN-tip100 (QIAGEN, U.S.A.). The sequence of the inserted gene was determined using conventional method, so that the sequence was confirmed to be identical to the corresponding region in SEQ ID NO: 31.
(2) Transfer of Mouse SCR-1 into Stromal Cell Initially, BOSC23 cells at 2×10$^6$ cells/dish were seeded on a collagen type I coated 60 mm dish (Asahi technoglass), and cultured in DMEM medium containing 10% FCS at 37° C., under an atmosphere of 5% $CO_2$, and at a humidity of 100%. Twelve to 18 hours after the start of the culture, the medium was replaced by two milliliters of OPTI MEM medium (GIBCO BRL).

About 3 µg of plasmid inserted with SCR-1 into the above described pMX-IRES-GFP was added to 18 µL of LIPO-FECTAMINE Reagent (GIBCO BRL) diluted with 100 µL of OPTI MEM medium, and allowed to stand at room temperature for 30 min. The prepared DNA solution was added to the above-prepared BOSC23 cell culture solution. After about five hours, two milliliters of DMEM medium containing 20% FCS (GIBCO BRL) was added.

IRES (Internal Ribosome Entry Site) was determined by an access of the ribosome to the internal site of the mRNA. Therefore, two genes could be expressed from one mRNA caused by ligation of upward and downward genes separated by IRES in one transcription unit during the construction of an expression vector. With respect to the above-described plasmid, cDNA of SCR-1 was inserted in upward site and GFP (Green Fluorescence Protein) was inserted in downward site. Thus, the expression of SCR-1 could be monitored by detecting the expression of GFP using FACS.

After about 24 hours, the medium was replaced by 4 ml of DMEM containing 10% FCS. Further, after about 48 hours, the culture medium was harvested. After the culture medium was filtrated through 0.45 µm filter, the filtrate was centrifuged at 1,200 g for 16 hours and the supernatant was removed, so that the virus precipitation was obtained.

AGM-s3-A7 cells were cultured in one milliliter of MEMα medium containing 10% FCS (GIBCO BRL) on a 24-well culture dish (FALCON) at 1×10$^4$ cells/well. After 12 to 18 hours, the virus precipitation was suspended in one milliliter of MEMα medium containing 10% FCS, so that the stromal cell culture medium and the virus suspension were replaced. Next, POLYBRENE (Sigma, SEQUA-BRENE) was added to be 10 µg/mL. After the culture dish was centrifuged at 700 g for 45 min., the cells were cultured at 37° C., under an atmosphere of 5% $CO_2$, and at a humidity of 100%. After 48 hours, the medium was replaced by one milliliter of MEM medium containing 10% FCS. After 24 hours, the cells were passaged on a 6-well culture dish (FALCON) and cultured in three milliliters of MEM medium containing 10% FCS. Forty-eight hours after the passage, GFP expression in the stromal cells was detected using a cell sorter (FACSVantage, Becton Dickinson), so that it was indirectly confirmed that not less than 80% cells expressed SCR-1.

Example 16

Co-Culture of Stromal Cells in which SCR-1 Gene was Overexpressed with Mouse Hematopoietic Stem Cells AGM-s3-A9 cells, AGM-s3-A7 cells, or AGM-s3-A7 cells, transduced with SCR-1 gene by retrovirus infections, were seeded in a 24-well culture dish at a density of 1×10$^5$ cells/well, and were cultured in MEMα medium containing 10% FCS for one day in order to allow the cells to proliferate to cover the whole bottom surface of the culture dish.

Then, the medium was replaced by 1 ml of fresh medium and thirty cells of the mouse hematopoietic stem cells (derived from C57BL/6-Ly5.1) obtained in Example 9 were sorted on this cell layer to initiate the co-cultures.

After 7 days of culture, all the cells in the co-culture were harvested by trypsinization (0.05% trypsin in PBS containing 0.5 mM EDTA at 37° C. for two to five minutes), and the extent of the expansion of hematopoietic stem and/or progenitor cells was analyzed in the following experiment.

Example 17

Transplantation of Hematopoietic Cells into Irradiated Recipient Mice

Thirty freshly isolated hematopoietic stem cells, obtained from C57BL/6-Ly5.1 mice by the procedure described above (CD 34 negative, Sca-1 positive, c-Kit positive, Lin negative cells, or cells derived from C57BL/6-Ly5.1 pep mouse), or whole the cells harvested on the 7th day of the co-culture, which was initiated with 30 hematopoietic stem cells, were transplanted into the five C57BL/6-Ly5.2 mice (eight weeks age and male, Charles River),which were irradiated with X-ray at 8.5 Gy, through the tail vein together with the 200,000 whole bone marrow cells derived from C57BL/6-Ly5.2 mice (Charles River).

After the transplantation, the peripheral blood cells were collected from the retro-orbital sinus over time, and analyzed for the proportion of the cells that were derived from Ly5.1 hematopoietic cells. The peripheral blood was analyzed according to the usual method (S. Kouzu, Fundamental techniques for immunology, YODOSHA, 1995). In order to lyse erythrocytes, three hundreds and fifty $\mu$L of distilled water was added to 50 $\mu$L of the peripheral blood and 30 seconds after addition of distilled water, the same amount of the twice concentrated PBS and centrifuged, so that white blood cells were recovered. After the cells were washed once using the staining buffer (PBS containing 5% FCS and 0.05% NaN$_3$), they were stained with anti-CD16 antibody, FITC-anti-Ly5.1, PE-anti-myeloid cells (Gr-1 and CD11c) and APC-anti-lymphoid cells (B220 and Thy1)(purchased from Pharmingen) and incubated for 30 min on ice. Stained cells were washed using the staining buffer and FACS analysis was performed.

Expansions in the number of the cells, that were capable of reconstituting hematopoietic cells during the culture of the hematopoietic stem cells were estimated by calculating proportions of Ly5.1 positive cells in the Gr-1 or CD11c positive cells (myeloid cells), or Ly5.1 positive cells in the CD90 or CD45R positive cells (lymphoid cells) in the peripheral blood in the transplanted mice at intervals.

FIG. 7 shows the results. When the cells co-cultured with AGM-s3-A7 cells were transplanted, high chimerism derived from the cultured Ly5.1 hematopoietic cells was not observed. From this result, it was demonstrated that AGM-s3-A7 cells themselves showed low activity to support the hematopoietic stem cells or hemopoietic precursor cells. When cells co-cultured with AGM-s3-A7 cells in which SCR-1 gene was overexpressed were transplanted, a significant high proportion of cells derived from the cultured cells was detected in both myeloid and lymphoid cells in the peripheral blood. Therefore, it was clear that the hematopoietic stem cells and the hemopoietic precursor cells, which could reconstitute the hemopoietic system of the irradiated mice, were supported and amplified on the A7 stromal cells in which SCR-1 gene was overepressed.

As a result, it was evident that SCR-1 had a function to give the stromal cells without an activity to support the survival or the proliferation of the hematopoietic stem cells or the hematopoietic progenitor cells the above described activity. From these results, it was evident that SCR-1 had an activity to effect on support the proliferation or the survival of the hematopoietic stem cells or the hemopoietic precursor cells; or an activity to effect the stromal cells so as to give them an activity to support the hematopoietic stem cells.

Example 18

SCR-1 Transgenic Mice

The activity of mouse and human SCR-1 can be confirmed by establishing genetically modified mice, such as transgenic mice. Appropriate promoters are selected for expression of SEQ ID NOS: 31 and 33 which allows their activity for hematopoietic stem cell growth or survival promotion to be confirmed. GATA-2 promoter drives expression of genes in very early hematopoietic stem or progenitor cell population. Expression of the SCR-1 gene (SEQ ID NOSL 31 or 33) under the regulation of GATA-2 promoter in transgenic mice will cause the hematopoietic stem or progenitor cells to express the SCR-1 gene. This SCR-1 gene expression in hematopoietic stem progenitor cells will lead to expansion of hematopoietic stem or progenitor cells which will result in an increase of hematopoietic cells in embryos, neonates or adult mutant mice. GATA-2 promoters described by Minegishi et al may be used for this purpose (J Biol Chem. 1998 Feb. 6;273(6):3625–34).

The SCR-1 gene (SEQ ID NOS: 31 or 33) may also be expressed under the control of CAG or other promoters that work in ubiquitous tissues (Kiwaki et al. Gene Ther, 1996 May 1;7(7):821–30). This will allow for determination of the effects of SCR-1 gene expression in other tissue cell types together with hematopoietic cells. Transgenic mice can be established accroding to the methods described in "Manipulating the Mouse Embryo" (Brigid Hogan, Rosa Beddington, Frank Costantini, Elizabeth Lacy, 1994, Cold Spring Harbor Laboratory Press).

What is claimed is:

1. An ex vivo method of promoting proliferation of a hematopoietic stem cell cell comprising contacting said cell with an amount of a polypeptide, wherein said polypeptide comprises an amino acid sequence at least 95% identical to the amino acid of SEQ ID NO: 13, 32 or 34 or the mature protein coding portion thereof and exhibits stem cell growth factor activity, and wherein said amount is effective to promote proliferation of said cell.

2. An ex vivo method of promoting proliferation of a hematopoietic stem cell comprising contacting said cell with an amount of a polypeptide, wherein the polypeptide is encoded by a polynucleotide that hybridizes to the complement of the nucleotide sequence of SEQ ID NO: 12, or the mature protein coding portion thereof, under the following stringent conditions: a final wash of 0.1×SSC/0.1% SDS at 68° C., wherein the amount is effective to promote proliferation of said cell.

3. An ex vivo method of maintaining survival of a hemoatropoietic stem cell comprising contacting said cell with an amount of a polypeptide, wherein said polypeptide comprises an amino acid sequence at least 95% identical to the amino acid of SEQ ID NO: 13, 32 or 34 or the mature protein coding portion thereof and exhibits stem cell growth factor activity, and wherein said amount is effective to maintain survival of said cell.

4. An ex vivo method of maintaining survival of a hematopoietic stem cell comprising contacting said cell with an amount of a polypeptide, wherein the polypeptide is encoded by a polynucleotide that hybridizes to the complement of the nucleotide sequence of SEQ ID NO: 12, or the mature protein coding portion thereof, under the following stringent conditions: a final wash of 0.1×SSC/0.1% SDS at 68° C., wherein the amount is effective to maintain survival of said cell.

5. The method of claim 1 or 3, wherein the polypeptide comprises the amino acid sequence of SEQ ID NO: 13, or the mature protein coding portion thereof.

6. The method of claim 1 or 3, wherein the polypeptide comprises the amino acid sequence of SEQ ID NO: 32, or the mature protein coding portion thereof.

7. The method of claim 1 or 3, wherein the polypeptide comprises the amino acid sequence of SEQ ID NO: 34, or the mature protein coding portion thereof.

* * * * *

UNITED STATES PATENT AND TRADEMARK OFFICE
CERTIFICATE OF CORRECTION

PATENT NO. : 6,824,973 B2 Page 1 of 1
DATED : November 30, 2004
INVENTOR(S) : Y. T. Tang et al.

It is certified that error appears in the above-identified patent and that said Letters Patent is hereby corrected as shown below:

<u>Title page,</u>
Item [73], Assignees, delete "Synnyvale" and insert -- Sunnyvale --, <u>Column 161,</u>
Line 38, delete "cell cell" and insert -- cell --,
Line 56, delete "hemoatropoietic" and insert -- hematopoietic --, Signed and Sealed this Third Day of May, 2005

JON W. DUDAS
*Director of the United States Patent and Trademark Office*

SEQUENCE LISTING

<160> NUMBER OF SEQ ID NOS: 48

<210> SEQ ID NO 1
<211> LENGTH: 301
<212> TYPE: DNA
<213> ORGANISM: Homo sapiens

<400> SEQUENCE: 1
gcacgagacg aggaaaaaaa ggaagggaga ggaaaagaaa aaaacctaat aaaggagaaa      60
gtaaagaagc aatacctgac agcaaaagtc tggaatccag caaagaaatc ccagagcaac     120
gagaaaacaa acagcagcag aagaagcgaa aagtccaaga taaacagaaa tcggtatcag     180
tcagcactgt acactagagg gttccatgag attattgtag actcatgatg ctgctatctc     240
aaccagatgc ccaggacagg tgctctagcc attaggacca caaatggaca tgtcagttat     300
t                                                                    301

<210> SEQ ID NO 2
<211> LENGTH: 392
<212> TYPE: DNA
<213> ORGANISM: Homo sapiens

<400> SEQUENCE: 2
tggaactcga tatccagata taaataagcg tacaaaatgc aaagctgact gtgatacctg      60
tttcaacaaa gatttctgca caaaatgtaa aagtggattt tacttacacc ttggaaagtg     120
ccttgacaat tgcccagaag ggttggaagc caacaaccat actatggagt gtgtcagtat     180
tgtgcactgt gaggtcagtg aatggaatcc ttggagtcca tgcacgaaga agggaaaaac     240
atgtggcttc aaaagaggga ctgaaacacg ggtccgagaa ataatacagc atccttcagc     300
aaagggtaac ctatgtcccc caacaaatga gacaagaaag tgtacagtgc aaaggaagaa     360
gtgtcagaag ggagaacgag gaaaataagg ag                                  392

<210> SEQ ID NO 3
<211> LENGTH: 475
<212> TYPE: DNA
<213> ORGANISM: Homo sapiens
<220> FEATURE:
<221> NAME/KEY: misc_feature
<222> LOCATION: (1)..(475)
<223> OTHER INFORMATION: n = A, T, G, or C

<400> SEQUENCE: 3
gtnagtaccc ccagggattt cactgagngc ctggactgag gacccgtcna anngcnngan      60
ccacgcgtnc gcccacgcgt ccggagagga aagaaaaaa acctaattta ggagaaagta     120
aagaagcaat acctgacagc ggaagtctgg aatggagcaa agaaatccca gagcaacgag     180
aaaacaaaca gcagcagaag aagcgaaaag tccaagataa acagaaatcg gtatcagtca     240
gcactgtaca ctagagggtt ccatgagatt attgtagact catgatgctg ctatctcaac     300
cagatgccca ggacaggtgc tctagccatt aggaccacaa atggacatgt cagttattgc     360
tctgtctaaa caacattccc agtagttgct atattcttca tacaagcata gttaacaaca     420
aagagccaaa agatcaaaga agggatactt tcagatggtt gtcttgtgtg cttcn         475

<210> SEQ ID NO 4
<211> LENGTH: 473
<212> TYPE: DNA
<213> ORGANISM: Homo sapiens

```
<220> FEATURE:
<221> NAME/KEY: misc_feature
<222> LOCATION: (1)..(473)
<223> OTHER INFORMATION: n = A, T, G, or C

<400> SEQUENCE: 4
tgggcannnn aaantttttga nattcgatcc gcgctgcagg aattcggcac gagacgagga     60
aaaaaaggaa gggagaggaa aagaaaaaaa cctaataaag gagaaagtaa agaagcaata    120
cctgacagca aaagtctgga atccagcaga gaaatcccag agcaacgaga aaacaaacag    180
cagcagaaga agcgaaaagt ccaagataaa cagaaatcgg tatcagtcag cactgtacac    240
tagagggttc catgagatta ttgtagactc atgatgctgc tatctcaacc agatgcccag    300
gacaggtgct ctagccatta ggaccacaaa tggacatgtc agttattgct ctgtctaaac    360
aacattccca gtagttgcta tattcttcat acaagcatag ttaacaacaa agagccaaaa    420
gatcaaagaa gggatacttt cagatggttg tcttgtgtgc ttctctgcat ttt           473

<210> SEQ ID NO 5
<211> LENGTH: 462
<212> TYPE: DNA
<213> ORGANISM: Homo sapiens
<220> FEATURE:
<221> NAME/KEY: misc_feature
<222> LOCATION: (1)..(462)
<223> OTHER INFORMATION: n = A, T, G, or C

<400> SEQUENCE: 5
tgggagannn ntttgaaact gagatcgtcg canacncnac nangaataaa aggaagggag     60
agggaaagaa aaaaacctaa taaggagaa agtaaagaat caatttctga cagcaaaagt    120
ctggaatcca tcaaagaaat cccatatcaa cgagaaaaca gacagcagca caaaagcga    180 aaagtccaag ataaacagaa atcggtatca gtcagcactg tacactagag ggttccatga    240
gattattgta gactcatgat gctgctatct caaccagatg cccaggacag gtgctctatc    300
cattacgacc acaaatggac atgtcagtta ttgctctgtc taaacaacat tcccagtagt    360
tgctatattc ttcatacaag catagttaac aacaaagagc caaagatcaa agaagggat    420 actttcagat ggttgtcttg tgtgcttctc tgcattttta aa                        462

<210> SEQ ID NO 6
<211> LENGTH: 384
<212> TYPE: DNA
<213> ORGANISM: Homo sapiens

<400> SEQUENCE: 6
aataatgtgt acaaaatgca aagctgactg tgatacctgt ttcaacaaaa atttctgcac     60
aaaatgtaaa agtggatttt acttacacct tggaaagtgc cttgacaatt gcccagaagg    120
gttggaagcc aacaaccata ctatggagtg tgtcagtatt gtgcactgtg aggtcagtga    180
atggaatcct tggagtccat gcacgaagaa gggaaaaaca tgtggcttca aagagggac    240 tgaaacacgg gtccgagaaa taatacagca tccttcagca aagggtaacc tatgtccccc    300
aacaaatgag acaagaaagt gtacagtgca aggaagaag tgtcagaagg gagaacgagg    360
aaaaaaagga agggagagga aaag                                            384

<210> SEQ ID NO 7
<211> LENGTH: 390
<212> TYPE: DNA
<213> ORGANISM: Homo sapiens
<220> FEATURE:
```

<221> NAME/KEY: misc_feature
<222> LOCATION: (1)..(390)
<223> OTHER INFORMATION: n = A, T, G, or C

<400> SEQUENCE: 7

```
cgttgctctg ggatttcttt gctggattcc agacttttgc tgtcaggtat tgcttcttta      60
cttctccctt tattaggttt ttttcttttc ctctcccttc cttttttcc tcgttctccc      120
ttctgacact tcttcctttg cactgtacac tttcttgtct catttgttgg gggacatagg     180
ttacccttg ctgaaggatg ctgtattatt tctcggaccc gtgtttcagt ccctcttttg      240
aagccacatg ttttcccctt cttcgtgcat ggactccaag gattccattc actgacctca    300
cagtgcacaa tactgacaca ctccatagta tggttgttgg cttccaaccc ttctgggcaa    360
ttgtcaaggc actttccaag gtgtaagtan                                      390
```

<210> SEQ ID NO 8
<211> LENGTH: 1345
<212> TYPE: DNA
<213> ORGANISM: Homo sapiens
<220> FEATURE:
<221> NAME/KEY: misc_feature
<222> LOCATION: (321)..(1235)
<223> OTHER INFORMATION: similar to gi4519541 in the genpept database
      release 114, Run with FASTXY3.3t00, default parameter

<400> SEQUENCE: 8

```
gcggccgccc cggcggctcc tggaaccccg gttcgcggcg atgccagcca ccccagcgaa     60
gccgccgcag ttcagtgctt ggataatttg aaagtacaat agttggtttc cctgtccacc    120
cgccccactt cgcttgccat cacagcacgc ctatcggatg tgagaggaga agtcccgctg    180
ctcgggcact gtctatatac gcctaacacc tacatatatt ttaaaaacat taaatataat   240
taacaatcaa agaaagagg agaaggaag ggaagcatta ctgggttact atgcacttgc      300
gactgatttc ttggcttttt atcattttga actttatgga atacatcggc agccaaaacg    360
cctcccgggg aaggcgccag cgaagaatgc atcctaacgt tagtcaaggc tgccaaggag   420
gctgtgcaac atgctcagat tacaatggat gtttgtcatg taagcccaga ctatttttg    480
ctctggaaag aattggcatg aagcagattg gagtatgtct catcttcatg tccaagtgga    540
tattatggaa ctcgatatcc agatataaat aatgtgtaca aaatgcaaag ctgactgtga    600
tacctgtttc aacaaaaatt tctgcacaaa atgtaaaagt ggattttact tacaccttgg   660
aaagtgcctt gacaattgcc cagaagggtt ggaagccaac aaccatacta tggagtgtgt   720
cagtattgtg cactgtgagg tcagtgaatg gaatccttgg agtccatgca cgaagaaggg   780
aaaaacatgt ggcttcaaaa gagggactga aacacgggtc cgagaaataa tacagcatcc   840
ttcagcaaag ggtaacctat gtcccccaac aaatgagaca agaaagtgta cagtgcaaag   900
gaagaagtgt cagaagggag aacgaggaaa aaaggaagg gagaggaaaa gaaaaaaacc    960
taataaagga gaaagtaaag aagcaatacc tgacagcaaa agtctggaat ccagcaaaga   1020
aatcccagag caacgagaaa acaaacagca gcagaagaag cgaaaagtcc aagataaaca    1080
gaaatcggta tcagtcagca ctgtacacta gagggttcca tgagattatt gtagactcat    1140
gatgctgcta tctcaaccag atgcccagga caggtgctct agccattagg accacaaatg   1200
gacatgtcag ttattgctct gtctaaacaa cattcccagt agttgctata ttcttcatac   1260
aagcatagtt aacaacaaag agccaaaaga tcaaagaagg gatactttca gatggttgtc   1320
ttgtgtgctt ctctgcattt ttaaa                                        1345
```

-continued

```
<210> SEQ ID NO 9
<211> LENGTH: 1343
<212> TYPE: DNA
<213> ORGANISM: Homo sapiens
<220> FEATURE:
<221> NAME/KEY: CDS
<222> LOCATION: (291)..(1109)

<400> SEQUENCE: 9
gcggccgccc cggcggctcc tggaacccg gttcgcggcg atgccagcca ccccagcgaa      60
gccgccgcag ttcagtgctt ggataatttg aaagtacaat agttggtttc cctgtccacc    120
cgccccactt cgcttgccat cacagcacgc ctatcggatg tgagaggaga agtcccgctg    180
ctcgggcact gtctatatac gcctaacacc tacatatatt ttaaaaacat taaatataat    240
taacaatcaa agaaagagg agaaaggaag ggaagcatta ctgggttact atg cac        296
                                                       Met His
                                                        1 ttg cga ctg att tct tgg ctt ttt atc att ttg aac ttt atg gaa tac      344
Leu Arg Leu Ile Ser Trp Leu Phe Ile Ile Leu Asn Phe Met Glu Tyr
      5                  10                  15 atc ggc agc caa aac gcc tcc cgg gga agg cgc cag cga aga atg cat      392
Ile Gly Ser Gln Asn Ala Ser Arg Gly Arg Arg Gln Arg Arg Met His
 20                  25                  30 cct aac gtt agt caa ggc tgc caa gga ggc tgt gca aca tgc tca gat      440
Pro Asn Val Ser Gln Gly Cys Gln Gly Gly Cys Ala Thr Cys Ser Asp
 35                  40                  45                  50 tac aat gga tgt ttg tca tgt aag ccc aga cta ttt ttt gct ctg gaa      488
Tyr Asn Gly Cys Leu Ser Cys Lys Pro Arg Leu Phe Phe Ala Leu Glu
                 55                  60                  65 aga att ggc atg aag cag att gga gta tgt ctc tct tca tgt cca agt      536
Arg Ile Gly Met Lys Gln Ile Gly Val Cys Leu Ser Ser Cys Pro Ser
         70                  75                  80 gga tat tat gga act cga tat cca gat ata aat aag tgt aca aaa tgc      584
Gly Tyr Tyr Gly Thr Arg Tyr Pro Asp Ile Asn Lys Cys Thr Lys Cys
     85                  90                  95 aaa gct gac tgt gat acc tgt ttc aac aaa aat ttc tgc aca aaa tgt      632
Lys Ala Asp Cys Asp Thr Cys Phe Asn Lys Asn Phe Cys Thr Lys Cys
100                 105                 110 aaa agt gga ttt tac tta cac ctt gga aag tgc ctt gac aat tgc cca      680
Lys Ser Gly Phe Tyr Leu His Leu Gly Lys Cys Leu Asp Asn Cys Pro
115                 120                 125                 130 gaa ggg ttg gaa gcc aac aac cat act atg gag tgt gtc agt att gtg      728
Glu Gly Leu Glu Ala Asn Asn His Thr Met Glu Cys Val Ser Ile Val
                135                 140                 145 cac tgt gag gtc agt gaa tgg aat cct tgg agt cca tgc acg aag aag      776
His Cys Glu Val Ser Glu Trp Asn Pro Trp Ser Pro Cys Thr Lys Lys
            150                 155                 160 gga aaa aca tgt ggc ttc aaa aga ggg act gaa aca cgg gtc cga gaa      824
Gly Lys Thr Cys Gly Phe Lys Arg Gly Thr Glu Thr Arg Val Arg Glu
        165                 170                 175 ata ata cag cat cct tca gca aag ggt aac cta tgt ccc cca aca aat      872
Ile Ile Gln His Pro Ser Ala Lys Gly Asn Leu Cys Pro Pro Thr Asn
    180                 185                 190 gag aca aga aag tgt aca gtg caa agg aag aag tgt cag aag gga gaa      920
Glu Thr Arg Lys Cys Thr Val Gln Arg Lys Lys Cys Gln Lys Gly Glu
195                 200                 205                 210 cga gga aaa aaa gga agg gag agg aaa aga aaa aaa cct aat aaa gga      968
Arg Gly Lys Lys Gly Arg Glu Arg Lys Arg Lys Lys Pro Asn Lys Gly
                215                 220                 225
```

-continued

```
gaa agt aaa gaa gca ata cct gac agc aaa agt ctg gaa tcc agc aaa    1016
Glu Ser Lys Glu Ala Ile Pro Asp Ser Lys Ser Leu Glu Ser Ser Lys
        230                 235                 240 gaa atc cca gag caa cga gaa aac aaa cag cag cag aag aag cga aaa    1064
Glu Ile Pro Glu Gln Arg Glu Asn Lys Gln Gln Gln Lys Lys Arg Lys
    245                 250                 255 gtc caa gat aaa cag aaa tcg gta tca gtc agc act gta cac tag        1109
Val Gln Asp Lys Gln Lys Ser Val Ser Val Ser Thr Val His
260                 265                 270 agggttccat gagattattg tagactcatg atgctgctat ctcaaccaga tgcccaggac   1169
aggtgctcta gccattagga ccacaaatgg acatgtcagt tattgctctg tctaaacaac   1229
attcccagta gttgctatat tcttcataca agcatagtta acaacaaaga gccaaaagat   1289
caaagaaggg atactttcag atggttgtct tgtgtgcttc tctgcatttt taaa         1343
```

<210> SEQ ID NO 10
<211> LENGTH: 272
<212> TYPE: PRT
<213> ORGANISM: Homo sapiens

<400> SEQUENCE: 10

```
Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Gln Arg Arg
            20                  25                  30

Met His Pro Asn Val Ser Gln Gly Cys Gln Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
    130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
        195                 200                 205

Gly Glu Arg Gly Lys Lys Gly Arg Glu Arg Lys Arg Lys Pro Asn
    210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255

Arg Lys Val Gln Asp Lys Gln Lys Ser Val Ser Val Ser Thr Val His
            260                 265                 270
```

-continued

```
<210> SEQ ID NO 11
<211> LENGTH: 819
<212> TYPE: DNA
<213> ORGANISM: Homo sapiens

<400> SEQUENCE: 11
atgcacttgc gactgatttc ttggcttttt atcattttga actttatgga atacatcggc      60
agccaaaacg cctcccgggg aaggcgccag cgaagaatgc atcctaacgt tagtcaaggc     120
tgccaaggag gctgtgcaac atgctcagat tacaatggat gtttgtcatg taagcccaga     180 ctatttttg ctctggaaag aattggcatg aagcagattg gagtatgtct ctcttcatgt      240
ccaagtggat attatggaac tcgatatcca gatataaata agtgtacaaa atgcaaagct     300
gactgtgata cctgtttcaa caaaaatttc tgcacaaaat gtaaagtgg attttactta      360 caccttggaa agtgccttga caattgccca aagggttgg aagccaacaa ccatactatg      420
gagtgtgtca gtattgtgca ctgtgaggtc agtgaatgga atccttggag tccatgcacg     480
aagaagggaa aaacatgtgg cttcaaaaga gggactgaaa cacgggtccg agaaataata     540
cagcatcctt cagcaaaggg taacctatgt cccccaacaa atgagacaag aaagtgtaca     600
gtgcaaagga agaagtgtca gaagggagaa cgaggaaaaa aaggaaggga gaggaaaaga     660
aaaaaaccta ataaggaga aagtaaagaa gcaatacctg acagcaaaag tctggaatcc      720
agcaaagaaa tcccagagca acgagaaaac aaacagcagc agaagaagcg aaaagtccaa     780
gataaacaga atcggtatc agtcagcact gtacactag                             819

<210> SEQ ID NO 12
<211> LENGTH: 822
<212> TYPE: DNA
<213> ORGANISM: Homo sapiens
<220> FEATURE:
<221> NAME/KEY: CDS
<222> LOCATION: (1)..(822)

<400> SEQUENCE: 12 atg ggt cac ttg cga ctg att tct tgg ctt ttt atc att ttg aac ttt      48
Met Gly His Leu Arg Leu Ile Ser Trp Leu Phe Ile Ile Leu Asn Phe
1               5                   10                  15 atg gaa tac atc ggc agc caa aac gcc tcc cgg gga agg cgc cag cga      96
Met Glu Tyr Ile Gly Ser Gln Asn Ala Ser Arg Gly Arg Arg Gln Arg
            20                  25                  30 aga atg cat cct aac gtt agt caa ggc tgc caa gga ggc tgt gca aca     144
Arg Met His Pro Asn Val Ser Gln Gly Cys Gln Gly Gly Cys Ala Thr
        35                  40                  45 tgc tca gat tac aat gga tgt ttg tca tgt aag ccc aga cta ttt ttt     192
Cys Ser Asp Tyr Asn Gly Cys Leu Ser Cys Lys Pro Arg Leu Phe Phe
    50                  55                  60 gct ctg gaa aga att ggc atg aag cag att gga gta tgt ctc tct tca     240
Ala Leu Glu Arg Ile Gly Met Lys Gln Ile Gly Val Cys Leu Ser Ser
65                  70                  75                  80 tgt cca agt gga tat tat gga act cga tat cca gat ata aat aag tgt     288
Cys Pro Ser Gly Tyr Tyr Gly Thr Arg Tyr Pro Asp Ile Asn Lys Cys
                85                  90                  95 aca aaa tgc aaa gct gac tgt gat acc tgt ttc aac aaa aat ttc tgc     336
Thr Lys Cys Lys Ala Asp Cys Asp Thr Cys Phe Asn Lys Asn Phe Cys
            100                 105                 110 aca aaa tgt aaa gtg gga ttt tac tta cac ctt gga aag tgc ctt gac     384
Thr Lys Cys Lys Ser Gly Phe Tyr Leu His Leu Gly Lys Cys Leu Asp
        115                 120                 125
```

-continued

```
aat tgc cca gaa ggg ttg gaa gcc aac aac cat act atg gag tgt gtc        432
Asn Cys Pro Glu Gly Leu Glu Ala Asn Asn His Thr Met Glu Cys Val
    130                 135                 140 agt att gtg cac tgt gag gtc agt gaa tgg aat cct tgg agt cca tgc        480
Ser Ile Val His Cys Glu Val Ser Glu Trp Asn Pro Trp Ser Pro Cys
145                 150                 155                 160 acg aag aag gga aaa aca tgt ggc ttc aaa aga ggg act gaa aca cgg        528
Thr Lys Lys Gly Lys Thr Cys Gly Phe Lys Arg Gly Thr Glu Thr Arg
                165                 170                 175 gtc cga gaa ata ata cag cat cct tca gca aag ggt aac cta tgt ccc        576
Val Arg Glu Ile Ile Gln His Pro Ser Ala Lys Gly Asn Leu Cys Pro
            180                 185                 190 cca aca aat gag aca aga aag tgt aca gtg caa agg aag aag tgt cag        624
Pro Thr Asn Glu Thr Arg Lys Cys Thr Val Gln Arg Lys Lys Cys Gln
        195                 200                 205 aag gga gaa cga gga aaa aaa gga agg gag agg aaa aga aaa aaa cct        672
Lys Gly Glu Arg Gly Lys Lys Gly Arg Glu Arg Lys Arg Lys Lys Pro
    210                 215                 220 aat aaa gga gaa agt aaa gaa gca ata cct gac agc aaa agt ctg gaa        720
Asn Lys Gly Glu Ser Lys Glu Ala Ile Pro Asp Ser Lys Ser Leu Glu
225                 230                 235                 240 tcc agc aaa gaa atc cca gag caa cga gaa aac aaa cag cag cag aag        768
Ser Ser Lys Glu Ile Pro Glu Gln Arg Glu Asn Lys Gln Gln Gln Lys
                245                 250                 255 aag cga aaa gtc caa gat aaa cag aaa tcg gta tca gtc agc act gta        816
Lys Arg Lys Val Gln Asp Lys Gln Lys Ser Val Ser Val Ser Thr Val
            260                 265                 270 cac tag                                                                822
His
```

<210> SEQ ID NO 13
<211> LENGTH: 273
<212> TYPE: PRT
<213> ORGANISM: Homo sapiens

<400> SEQUENCE: 13

```
Met Gly His Leu Arg Leu Ile Ser Trp Leu Phe Ile Ile Leu Asn Phe
1               5                   10                  15

Met Glu Tyr Ile Gly Ser Gln Asn Ala Ser Arg Gly Arg Arg Gln Arg
            20                  25                  30

Arg Met His Pro Asn Val Ser Gln Gly Cys Gln Gly Cys Ala Thr
        35                  40                  45

Cys Ser Asp Tyr Asn Gly Cys Leu Ser Cys Lys Pro Arg Leu Phe Phe
    50                  55                  60

Ala Leu Glu Arg Ile Gly Met Lys Gln Ile Gly Val Cys Leu Ser Ser
65                  70                  75                  80

Cys Pro Ser Gly Tyr Tyr Gly Thr Arg Tyr Pro Asp Ile Asn Lys Cys
                85                  90                  95

Thr Lys Cys Lys Ala Asp Cys Asp Thr Cys Phe Asn Lys Asn Phe Cys
            100                 105                 110

Thr Lys Cys Lys Ser Gly Phe Tyr Leu His Leu Gly Lys Cys Leu Asp
        115                 120                 125

Asn Cys Pro Glu Gly Leu Glu Ala Asn Asn His Thr Met Glu Cys Val
    130                 135                 140

Ser Ile Val His Cys Glu Val Ser Glu Trp Asn Pro Trp Ser Pro Cys
145                 150                 155                 160

Thr Lys Lys Gly Lys Thr Cys Gly Phe Lys Arg Gly Thr Glu Thr Arg
                165                 170                 175
```

```
Val Arg Glu Ile Ile Gln His Pro Ser Ala Lys Gly Asn Leu Cys Pro
            180                 185                 190

Pro Thr Asn Glu Thr Arg Lys Cys Thr Val Gln Arg Lys Lys Cys Gln
        195                 200                 205

Lys Gly Glu Arg Gly Lys Lys Gly Arg Glu Arg Lys Arg Lys Lys Pro
    210                 215                 220

Asn Lys Gly Glu Ser Lys Glu Ala Ile Pro Asp Ser Lys Ser Leu Glu
225                 230                 235                 240

Ser Ser Lys Glu Ile Pro Glu Gln Arg Glu Asn Lys Gln Gln Gln Lys
                245                 250                 255

Lys Arg Lys Val Gln Asp Lys Gln Lys Ser Val Ser Val Ser Thr Val
                260                 265                 270

His

<210> SEQ ID NO 14
<211> LENGTH: 160
<212> TYPE: PRT
<213> ORGANISM: Homo sapiens

<400> SEQUENCE: 14

Cys Thr Lys Cys Lys Ala Asp Cys Asp Thr Cys Phe Asn Lys Asn Phe
1               5                   10                  15

Cys Thr Lys Cys Lys Ser Gly Phe Tyr Leu His Leu Gly Lys Cys Leu
            20                  25                  30

Asp Asn Cys Pro Glu Gly Leu Glu Ala Asn Asn His Thr Met Glu Cys
        35                  40                  45

Val Ser Ile Val His Cys Glu Val Ser Glu Trp Asn Pro Trp Ser Pro
    50                  55                  60

Cys Thr Lys Lys Gly Lys Thr Cys Gly Phe Lys Arg Gly Thr Glu Thr
65                  70                  75                  80

Arg Val Arg Glu Ile Ile Gln His Pro Ser Ala Lys Gly Asn Leu Cys
                85                  90                  95

Pro Pro Thr Asn Glu Thr Arg Lys Cys Thr Val Gln Arg Lys Lys Cys
            100                 105                 110

Gln Lys Gly Glu Arg Gly Lys Lys Gly Arg Glu Arg Lys Arg Lys Lys
        115                 120                 125

Pro Asn Lys Gly Glu Ser Lys Glu Ala Ile Pro Asp Ser Lys Ser Leu
    130                 135                 140

Glu Ser Ser Lys Glu Ile Pro Glu Gln Arg Glu Asn Lys Gln Gln Gln
145                 150                 155                 160

<210> SEQ ID NO 15
<211> LENGTH: 21
<212> TYPE: PRT
<213> ORGANISM: Homo sapiens

<400> SEQUENCE: 15

Met His Leu Arg Leu Ile Ser Trp Leu Phe Ile Ile Leu Asn Phe Met
1               5                   10                  15

Glu Tyr Ile Gly Ser
            20

<210> SEQ ID NO 16
<211> LENGTH: 251
<212> TYPE: PRT
<213> ORGANISM: Homo sapiens
```

```
<400> SEQUENCE: 16

Gln Asn Ala Ser Arg Gly Arg Arg Gln Arg Met His Pro Asn Val
1               5                   10                  15

Ser Gln Gly Cys Gln Gly Gly Cys Ala Thr Cys Ser Asp Tyr Asn Gly
                20                  25                  30

Cys Leu Ser Cys Lys Pro Arg Leu Phe Phe Ala Leu Glu Arg Ile Gly
            35                  40                  45

Met Lys Gln Ile Gly Val Cys Leu Ser Ser Cys Pro Ser Gly Tyr Tyr
    50                  55                  60

Gly Thr Arg Tyr Pro Asp Ile Asn Lys Cys Thr Lys Cys Lys Ala Asp
65                  70                  75                  80

Cys Asp Thr Cys Phe Asn Lys Asn Phe Cys Thr Lys Cys Lys Ser Gly
                85                  90                  95

Phe Tyr Leu His Leu Gly Lys Cys Leu Asp Asn Cys Pro Glu Gly Leu
                100                 105                 110

Glu Ala Asn Asn His Thr Met Glu Cys Val Ser Ile Val His Cys Glu
            115                 120                 125

Val Ser Glu Trp Asn Pro Trp Ser Pro Cys Thr Lys Lys Gly Lys Thr
130                 135                 140

Cys Gly Phe Lys Arg Gly Thr Glu Thr Arg Val Arg Glu Ile Ile Gln
145                 150                 155                 160

His Pro Ser Ala Lys Gly Asn Leu Cys Pro Pro Thr Asn Glu Thr Arg
                165                 170                 175

Lys Cys Thr Val Gln Arg Lys Lys Cys Gln Lys Gly Glu Arg Gly Lys
            180                 185                 190

Lys Gly Arg Glu Arg Lys Arg Lys Pro Asn Lys Gly Glu Ser Lys
        195                 200                 205

Glu Ala Ile Pro Asp Ser Lys Ser Leu Glu Ser Ser Lys Glu Ile Pro
    210                 215                 220

Glu Gln Arg Glu Asn Lys Gln Gln Lys Lys Arg Lys Val Gln Asp
225                 230                 235                 240

Lys Gln Lys Ser Val Ser Val Ser Thr Val His
                245                 250

<210> SEQ ID NO 17
<211> LENGTH: 23
<212> TYPE: PRT
<213> ORGANISM: Homo sapiens

<400> SEQUENCE: 17

Ala Asp Cys Asp Thr Cys Phe Asn Lys Asn Phe Cys Thr Lys Cys Lys
1               5                   10                  15

Ser Gly Phe Tyr Leu His Leu
            20

<210> SEQ ID NO 18
<211> LENGTH: 46
<212> TYPE: PRT
<213> ORGANISM: Homo sapiens

<400> SEQUENCE: 18

Ile Asn Lys Cys Thr Lys Cys Lys Ala Asp Cys Asp Thr Cys Phe Asn
1               5                   10                  15

Lys Asn Phe Cys Thr Lys Cys Lys Ser Gly Phe Tyr Leu His Leu Gly
                20                  25                  30

Lys Cys Leu Asp Asn Cys Pro Glu Gly Leu Glu Ala Asn Asn
```

<210> SEQ ID NO 19
<211> LENGTH: 20
<212> TYPE: PRT
<213> ORGANISM: Homo sapiens

<400> SEQUENCE: 19

Met His Pro Asn Val Ser Gln Gly Cys Gln Gly Gly Cys Ala Thr Cys
1               5                   10                  15

Ser Asp Tyr Asn
            20

<210> SEQ ID NO 20
<211> LENGTH: 37
<212> TYPE: PRT
<213> ORGANISM: Homo sapiens

<400> SEQUENCE: 20

Ile Val His Cys Glu Val Ser Glu Trp Asn Pro Trp Ser Pro Cys Thr
1               5                   10                  15

Lys Lys Gly Lys Thr Cys Gly Phe Lys Arg Gly Thr Glu Thr Arg Val
            20                  25                  30

Arg Glu Ile Ile Gln
        35

<210> SEQ ID NO 21
<211> LENGTH: 10
<212> TYPE: PRT
<213> ORGANISM: Homo sapiens

<400> SEQUENCE: 21

Lys Lys Gly Arg Glu Arg Lys Arg Lys Lys
1               5                   10

<210> SEQ ID NO 22
<211> LENGTH: 42
<212> TYPE: PRT
<213> ORGANISM: Homo sapiens

<400> SEQUENCE: 22

Lys Cys Thr Val Gln Arg Lys Lys Cys Gln Lys Gly Glu Arg Gly Lys
1               5                   10                  15

Lys Gly Arg Glu Arg Lys Arg Lys Pro Asn Lys Gly Glu Ser Lys
            20                  25                  30

Glu Ala Ile Pro Asp Ser Lys Ser Leu Glu
        35                  40

<210> SEQ ID NO 23
<211> LENGTH: 14
<212> TYPE: PRT
<213> ORGANISM: Homo sapiens

<400> SEQUENCE: 23

Thr Cys Phe Asn Lys Asn Phe Cys Thr Lys Cys Lys Ser Gly
1               5                   10

<210> SEQ ID NO 24
<211> LENGTH: 20
<212> TYPE: PRT
<213> ORGANISM: Homo sapiens

<400> SEQUENCE: 24

-continued

```
Cys Glu Val Ser Glu Trp Asn Pro Trp Ser Pro Cys Thr Lys Gly
1               5                   10                  15

Lys Thr Cys Gly
            20

<210> SEQ ID NO 25
<211> LENGTH: 229
<212> TYPE: PRT
<213> ORGANISM: Mus musculus

<400> SEQUENCE: 25

Val Gly Ser Arg Gly Ile Lys Gly Lys Arg Gln Arg Arg Ile Ser Ala
1               5                   10                  15

Glu Gly Ser Gln Ala Cys Ala Lys Gly Cys Glu Leu Cys Ser Glu Val
                20                  25                  30

Asn Gly Cys Leu Lys Cys Ser Pro Lys Leu Phe Ile Leu Leu Glu Arg
            35                  40                  45

Asn Asp Ile Arg Gln Val Gly Val Cys Leu Pro Ser Cys Pro Pro Gly
    50                  55                  60

Tyr Phe Asp Ala Arg Asn Pro Asp Met Asn Lys Cys Ile Lys Cys Lys
65                  70                  75                  80

Ile Glu His Cys Glu Ala Cys Phe Ser His Asn Phe Cys Thr Lys Cys
                85                  90                  95

Gln Glu Ala Leu Tyr Leu His Lys Gly Arg Cys Tyr Pro Ala Cys Pro
                100                 105                 110

Glu Gly Ser Thr Ala Ala Asn Ser Thr Met Glu Cys Gly Ser Pro Ala
            115                 120                 125

Gln Cys Glu Met Ser Glu Trp Ser Pro Trp Gly Pro Cys Ser Lys Lys
    130                 135                 140

Arg Lys Leu Cys Gly Phe Arg Lys Gly Ser Glu Glu Arg Thr Arg Arg
145                 150                 155                 160

Val Leu His Ala Pro Gly Gly Asp His Thr Thr Cys Ser Asp Thr Lys
                165                 170                 175

Glu Thr Arg Lys Cys Thr Val Arg Thr Pro Cys Pro Glu Gly Gln
                180                 185                 190

Lys Arg Arg Lys Gly Gly Gln Gly Arg Arg Glu Asn Ala Asn Arg His
            195                 200                 205

Pro Ala Arg Lys Asn Ser Lys Glu Pro Arg Ser Asn Ser Arg Arg His
    210                 215                 220

Lys Gly Gln Gln Gln
225

<210> SEQ ID NO 26
<211> LENGTH: 265
<212> TYPE: PRT
<213> ORGANISM: Homo sapiens

<400> SEQUENCE: 26

Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Arg Gln Arg Arg
                20                  25                  30

Met His Pro Asn Val Ser Gln Gly Cys Gln Gly Gly Cys Ala Thr Cys
            35                  40                  45

Ser Asp Tyr Asn Gly Cys Leu Ser Cys Lys Pro Arg Leu Phe Phe Ala
    50                  55                  60
```

-continued

```
Leu Glu Arg Ile Gly Met Lys Gln Ile Gly Val Cys Leu Ser Ser Cys
 65                  70                  75                  80

Pro Ser Gly Tyr Tyr Gly Thr Arg Tyr Pro Asp Ile Asn Lys Cys Thr
                 85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Cys Gln Lys
        195                 200                 205

Gly Glu Arg Gly Lys Gly Arg Glu Arg Lys Arg Lys Lys Pro Asn
210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255

Arg Lys Val Gln Asp Lys Gln Lys Ser
            260                 265

<210> SEQ ID NO 27
<211> LENGTH: 8
<212> TYPE: PRT
<213> ORGANISM: Homo sapiens

<400> SEQUENCE: 27

Ser Val Ser Val Ser Thr Val His
  1               5

<210> SEQ ID NO 28
<211> LENGTH: 7
<212> TYPE: PRT
<213> ORGANISM: Homo sapiens

<400> SEQUENCE: 28

Val Ser Val Ser Thr Val His
  1               5

<210> SEQ ID NO 29
<211> LENGTH: 27
<212> TYPE: PRT
<213> ORGANISM: Homo sapiens

<400> SEQUENCE: 29

Gly Ile Glu Val Thr Leu Ala Glu Gly Leu Thr Ser Val Ser Gln Arg
  1               5                  10                  15

Thr Gln Pro Thr Pro Cys Arg Arg Arg Tyr Leu
                 20                  25

<210> SEQ ID NO 30
<211> LENGTH: 30
```

-continued

```
<212> TYPE: DNA
<213> ORGANISM: Artificial Sequence
<220> FEATURE:
<223> OTHER INFORMATION: Description of Artificial Sequence: PCR primer

<400> SEQUENCE: 30
ctcgggaaga agcgcgccat ttgtgttggt                                         30

<210> SEQ ID NO 31
<211> LENGTH: 2384
<212> TYPE: DNA
<213> ORGANISM: Mus musculus
<220> FEATURE:
<221> NAME/KEY: CDS
<222> LOCATION: (511)..(1347)
<220> FEATURE:
<221> NAME/KEY: misc_feature
<222> LOCATION: (2367)..(2367)
<223> OTHER INFORMATION: n = A, T, G, or C

<400> SEQUENCE: 31
ggagcggctc ctgctcagaa cgccagaagc agctcgggtc tctccagcgc cccttgacca        60
tggctgcggt acccacggcg tccgcttccc tgcgctcccg gggtccctgc acagccgca       120 gccgctgcag cctctgagcc caggggcca ctgctcgcct ggattccgcc cgcagccgcc       180
gctgctgtgc aaccgaggct aacctgcggc cagccaggag gctcctgcaa ccttcgctcg      240
cggcgatgac agccacccca gagcagccgg ctgtgttcgg acaatttgag aatgcaattg      300
ttggtttccc ggtccacccg tcccgcttcg cttgccatca cagcacgcct gttggatctc      360
agtggagaag tcccgctgct ctggtttttc tactcttcgt atagactcgc ctaacaccta      420
catacatatt tttctttaaa aaaaaacatt aaatataact aacagtgaaa agaaaaagga      480
gagaaaaaag ggaaacatta cagggttact atg cac ttg cga ctg att tct tgt      534
                                    Met His Leu Arg Leu Ile Ser Cys
                                     1               5 ttt ttt atc att ttg aac ttt atg gaa tac att ggc agc caa aac gcc       582
Phe Phe Ile Ile Leu Asn Phe Met Glu Tyr Ile Gly Ser Gln Asn Ala
        10                  15                  20 tcc cga gga agg cgc cag cga aga atg cat cct aat gtc agt caa ggc       630
Ser Arg Gly Arg Arg Gln Arg Arg Met His Pro Asn Val Ser Gln Gly
 25                  30                  35                  40 tgc caa gga ggc tgt gca acg tgt tca gat tac aat ggc tgt ttg tca       678
Cys Gln Gly Gly Cys Ala Thr Cys Ser Asp Tyr Asn Gly Cys Leu Ser
                 45                  50                  55 tgt aag ccc aga ctg ttt ttt gtt ctg gaa agg att ggc atg aag cag      726
Cys Lys Pro Arg Leu Phe Phe Val Leu Glu Arg Ile Gly Met Lys Gln
             60                  65                  70 ata gga gtg tgt ctc tct tcg tgt cca agt gga tat tac gga act cga      774
Ile Gly Val Cys Leu Ser Ser Cys Pro Ser Gly Tyr Tyr Gly Thr Arg
         75                  80                  85 tat cca gat ata aat aaa tgt aca aaa tgc aaa gtt gac tgt gat acc      822
Tyr Pro Asp Ile Asn Lys Cys Thr Lys Cys Lys Val Asp Cys Asp Thr
     90                  95                 100 tgt ttc aac aaa aat ttc tgc aca aag tgt aaa agt gga ttt tac tta      870
Cys Phe Asn Lys Asn Phe Cys Thr Lys Cys Lys Ser Gly Phe Tyr Leu
105                 110                 115                 120 cac ctt gga aag tgc ctt gac agt tgc cca gaa ggg tta gaa gcc aac      918
His Leu Gly Lys Cys Leu Asp Ser Cys Pro Glu Gly Leu Glu Ala Asn
                125                 130                 135 aat cat act atg gaa tgt gtc agt att gta cac tgt gag gcc agt gaa      966
Asn His Thr Met Glu Cys Val Ser Ile Val His Cys Glu Ala Ser Glu
            140                 145                 150
```

| | | |
|---|---|---|
| tgg agt cca tgg agt cca tgt atg aag aaa gga aaa aca tgt ggc ttc<br>Trp Ser Pro Trp Ser Pro Cys Met Lys Lys Gly Lys Thr Cys Gly Phe<br>              155                         160                   165 | | 1014 |
| aaa agg ggg act gaa aca cgg gtc cga gat ata cta cag cat cct tca<br>Lys Arg Gly Thr Glu Thr Arg Val Arg Asp Ile Leu Gln His Pro Ser<br>170                        175                        180 | | 1062 |
| gcc aag ggt aag ggt aac ctg tgc ccc cca acc agc gag aca aga act<br>Ala Lys Gly Lys Gly Asn Leu Cys Pro Pro Thr Ser Glu Thr Arg Thr<br>185                      190                    195                   200 | | 1110 |
| tgt ata gta caa aga aag aag tgt tca aag gga gag cga gga aaa aag<br>Cys Ile Val Gln Arg Lys Lys Cys Ser Lys Gly Glu Arg Gly Lys Lys<br>               205                     210                   215 | | 1158 |
| gga aga gag aga aaa cga aaa aaa ctg aat aaa gaa gaa aga aag gaa<br>Gly Arg Glu Arg Lys Arg Lys Lys Leu Asn Lys Glu Glu Arg Lys Glu<br>        220                     225                     230 | | 1206 |
| aca agc tcc tcc tct gac agc aaa ggt ttg gag tcc agc att gag acc<br>Thr Ser Ser Ser Ser Asp Ser Lys Gly Leu Glu Ser Ser Ile Glu Thr<br>           235                     240                   245 | | 1254 |
| cca gac cag cag gaa aac aaa gag agg cag cag cag cag aag aga aga<br>Pro Asp Gln Gln Glu Asn Lys Glu Arg Gln Gln Gln Gln Lys Arg Arg<br>250                        255                    260 | | 1302 |
| gcc cga gac aag caa cag aaa tcg gta tca gtc agc act gta cac<br>Ala Arg Asp Lys Gln Gln Lys Ser Val Ser Val Ser Thr Val His<br>265                        270                    275 | | 1347 |
| tagagggtcc tgcgaggtta ctgtagactc atgatgctgc tatctcaacc agatgtccag | | 1407 |
| gacaggtgtt ctagccatta gaaccacaaa tggacaacac atcagttacc actctgtcta | | 1467 |
| aacaacattc ctaatagttg ctatattctt catacaaaca tagtaaacag caaagagcca | | 1527 |
| aatgttcaaa gaagggatac tttcagatgg ttatcttatg tgcttctgtg tattttaaa | | 1587 |
| agatgagaaa atttgtacat aattatcaat aagctataag atatcctcaa tgtaatgacg | | 1647 |
| acagctggac aagaatcatc ttttctttat aaaaaaatta ttcttcgaat aatttgtcttt | | 1707 |
| aagaagcaaa aggtaattct gcaacttcaa aaatgcagtg tccctcaaaa ccaagatttg | | 1767 |
| tcaggggaga gaatcatggc tccatgtaca gggtggattt gtcccggaga actagtgaat | | 1827 |
| gctcagaatt agggcctggc atttgaatc ctagagttaa tcatcacaga agcaagtggt | | 1887 |
| ttaggattgc ttcggttgcc ctcctctgca agaaactgaa catgcataat agagttaaat | | 1947 |
| atattgtgtg gagttggaat aaggcaagct gtggaagaaa tcatagagct ggagaccatc | | 2007 |
| ttgtgctttc cagaaccgtg aggggttttg gtcacctgga acagggctcc aatctatatt | | 2067 |
| agcactgtgt ggttgatctt ccactactcc ttggtttata taagtctgta aacatgtacc | | 2127 |
| tgtacctttc ttccaaaagt aaaccatac ttactagaag aaaattctaa ctttatggaa | | 2187 |
| aacaaaagtg taagaagaat gtgacatgtt tgcaaagttg agtgttttct ttctgaaatg | | 2247 |
| agggaaaac tatttttatta cctgcctatg ggtccacctg gaactaaagg gatactactt | | 2307 |
| tctaacaagg tgtatctagt aggagagaaa gccaccacaa taaatatatt tgttaatagn | | 2367 |
| taaaaaaaaa aaaaaaa | | 2384 |

<210> SEQ ID NO 32
<211> LENGTH: 279
<212> TYPE: PRT
<213> ORGANISM: Mus musculus

<400> SEQUENCE: 32

Met His Leu Arg Leu Ile Ser Cys Phe Phe Ile Ile Leu Asn Phe Met
1               5                   10                 15

```
Glu Tyr Ile Gly Ser Gln Asn Ala Ser Arg Gly Arg Gln Arg Arg
         20                  25                  30

Met His Pro Asn Val Ser Gln Gly Cys Gln Gly Gly Cys Ala Thr Cys
     35                  40                  45

Ser Asp Tyr Asn Gly Cys Leu Ser Cys Lys Pro Arg Leu Phe Phe Val
     50                  55                  60

Leu Glu Arg Ile Gly Met Lys Gln Ile Gly Val Cys Leu Ser Ser Cys
 65                  70                  75                  80

Pro Ser Gly Tyr Tyr Gly Thr Arg Tyr Pro Asp Ile Asn Lys Cys Thr
                 85                  90                  95

Lys Cys Lys Val Asp Cys Asp Thr Cys Phe Asn Lys Asn Phe Cys Thr
                100                 105                 110

Lys Cys Lys Ser Gly Phe Tyr Leu His Leu Gly Lys Cys Leu Asp Ser
                115                 120                 125

Cys Pro Glu Gly Leu Glu Ala Asn Asn His Thr Met Glu Cys Val Ser
        130                 135                 140

Ile Val His Cys Glu Ala Ser Glu Trp Ser Pro Trp Ser Pro Cys Met
145                 150                 155                 160

Lys Lys Gly Lys Thr Cys Gly Phe Lys Arg Gly Thr Glu Thr Arg Val
                165                 170                 175

Arg Asp Ile Leu Gln His Pro Ser Ala Lys Gly Lys Gly Asn Leu Cys
                180                 185                 190

Pro Pro Thr Ser Glu Thr Arg Thr Cys Ile Val Gln Arg Lys Lys Cys
                195                 200                 205

Ser Lys Gly Glu Arg Gly Lys Lys Gly Arg Glu Arg Lys Arg Lys Lys
        210                 215                 220

Leu Asn Lys Glu Glu Arg Lys Glu Thr Ser Ser Ser Asp Ser Lys
225                 230                 235                 240

Gly Leu Glu Ser Ser Ile Glu Thr Pro Asp Gln Gln Glu Asn Lys Glu
                245                 250                 255

Arg Gln Gln Gln Gln Lys Arg Arg Ala Arg Asp Lys Gln Gln Lys Ser
                260                 265                 270

Val Ser Val Ser Thr Val His
                275

<210> SEQ ID NO 33
<211> LENGTH: 2101
<212> TYPE: DNA
<213> ORGANISM: Homo sapiens
<220> FEATURE:
<221> NAME/KEY: CDS
<222> LOCATION: (259)..(1074)

<400> SEQUENCE: 33
tcgcggcgat gccagccacc ccagcgaagc cgccgcagtt cagtgcttgg ataatttgaa      60
agtacaatag ttggtttccc tgtccacccg ccccacttcg cttgccatca cagcacgcct     120
atcggatgtg agaggagaag tcccgctgct cgggcactgt ctatatacgc ctaacaccta     180
catatatttt aaaaacatta aatataatta acaatcaaaa gaaagaggag aaaggaaggg     240
aagcattact gggttact atg cac ttg cga ctg att tct tgg ctt ttt atc      291
                    Met His Leu Arg Leu Ile Ser Trp Leu Phe Ile
                      1               5                  10 att ttg aac ttt atg gaa tac atc ggc agc caa aac gcc tcc cgg gga      339
Ile Leu Asn Phe Met Glu Tyr Ile Gly Ser Gln Asn Ala Ser Arg Gly
             15                  20                  25
```

-continued

| | | |
|---|---|---|
| agg cgc cag cga aga atg cat cct aac gtt agt caa ggc tgc caa gga<br>Arg Arg Gln Arg Arg Met His Pro Asn Val Ser Gln Gly Cys Gln Gly<br>           30                      35                        40 | | 387 |
| ggc tgt gca aca tgc tca gat tac aat gga tgt ttg tca tgt aag ccc<br>Gly Cys Ala Thr Cys Ser Asp Tyr Asn Gly Cys Leu Ser Cys Lys Pro<br>    45                        50                        55 | | 435 |
| aga cta ttt ttt gct ctg gaa aga att ggc atg aag cag att gga gta<br>Arg Leu Phe Phe Ala Leu Glu Arg Ile Gly Met Lys Gln Ile Gly Val<br>60                        65                        70                        75 | | 483 |
| tgt ctc tct tca tgt cca agt gga tat tat gga act cga tat cca gat<br>Cys Leu Ser Ser Cys Pro Ser Gly Tyr Tyr Gly Thr Arg Tyr Pro Asp<br>                    80                        85                        90 | | 531 |
| ata aat aag tgt aca aaa tgc aaa gct gac tgt gat acc tgt ttc aac<br>Ile Asn Lys Cys Thr Lys Cys Lys Ala Asp Cys Asp Thr Cys Phe Asn<br>                        95                        100                      105 | | 579 |
| aaa aat ttc tgc aca aaa tgt aaa agt gga ttt tac tta cac ctt gga<br>Lys Asn Phe Cys Thr Lys Cys Lys Ser Gly Phe Tyr Leu His Leu Gly<br>          110                      115                      120 | | 627 |
| aag tgc ctt gac aat tgc cca gaa ggg ttg gaa gcc aac aac cat act<br>Lys Cys Leu Asp Asn Cys Pro Glu Gly Leu Glu Ala Asn Asn His Thr<br>125                        130                      135 | | 675 |
| atg gag tgt gtc agt att gtg cac tgt gag gtc agt gaa tgg aat cct<br>Met Glu Cys Val Ser Ile Val His Cys Glu Val Ser Glu Trp Asn Pro<br>140                        145                      150                      155 | | 723 |
| tgg agt cca tgc acg aag aag gga aaa aca tgt ggc ttc aaa aga ggg<br>Trp Ser Pro Cys Thr Lys Lys Gly Lys Thr Cys Gly Phe Lys Arg Gly<br>                    160                      165                      170 | | 771 |
| act gaa aca cgg gtc cga gaa ata ata cag cat cct tca gca aag ggt<br>Thr Glu Thr Arg Val Arg Glu Ile Ile Gln His Pro Ser Ala Lys Gly<br>                175                      180                      185 | | 819 |
| aac cta tgt ccc cca aca aat gag aca aga aag tgt aca gtg caa agg<br>Asn Leu Cys Pro Pro Thr Asn Glu Thr Arg Lys Cys Thr Val Gln Arg<br>          190                      195                      200 | | 867 |
| aag aag tgt cag aag gga gaa cga gga aaa aaa gga agg gag agg aaa<br>Lys Lys Cys Gln Lys Gly Glu Arg Gly Lys Lys Gly Arg Glu Arg Lys<br>205                        210                      215 | | 915 |
| aga aaa aaa cct aat aaa gga gaa agt aaa gaa gca ata cct gac agc<br>Arg Lys Lys Pro Asn Lys Gly Glu Ser Lys Glu Ala Ile Pro Asp Ser<br>220                        225                      230                      235 | | 963 |
| aaa agt ctg gaa tcc agc aaa gaa atc cca gag caa cga gaa aac aaa<br>Lys Ser Leu Glu Ser Ser Lys Glu Ile Pro Glu Gln Arg Glu Asn Lys<br>                240                      245                      250 | | 1011 |
| cag cag cag aag aag cga aaa gtc caa gat aaa cag aaa tcg gta tca<br>Gln Gln Gln Lys Lys Arg Lys Val Gln Asp Lys Gln Lys Ser Val Ser<br>          255                      260                      265 | | 1059 |
| gtc agc act gta cac tagagggttc catgagatta ttgtagactc atgatgctgc<br>Val Ser Thr Val His<br>          270 | | 1114 |
| tatctcaacc agatgcccag dacaggtgct ctagccatta ggaccacaaa tggacatgtc | | 1174 |
| agttattgct ctgtctaaac aacattccca gtagttgcta tattcttcat acaagcatag | | 1234 |
| ttaacaacaa agagccaaaa gatcaaagaa gggatacttt cagatggttg tcttgtgtgc | | 1294 |
| ttctctgcat tttttaaaga caagacattc ttgtacatat tatcaatagg ctataagatg | | 1354 |
| taacaacgaa atgatgacat ctggagaaga aacatctttt ccttataaaa atgtgttttc | | 1414 |
| aagctgttgt tttaagaagc aaaagatagt tctgcaaatt caaagataca gtatcccttc | | 1474 |
| aaaacaaata ggagttcagg gaagagaaac atccttcaaa ggacagtgtt gttttgaccg | | 1534 |
| ggagatctag agagtgctca gaattagggc ctggcatttg gaatcacagg atttatcatc | | 1594 |

```
acagaaacaa ctgttttaag attagttcca tcactctcat cctgtatttt tataagaaac    1654
acaagagtgc ataccagaat tgaatatacc atatgggatt ggagaaagac aaatgtggaa    1714
gaaatcatag agctggagac tactttgtg ctttacaaaa ctgtgaagga ttgtggtcac     1774
ctggaacagg tctccaatct atgttagcac tatgtggctc agcctctgtt accccttgga    1834
ttatatatca acctgtaaac atgtgcctgt aacttacttc caaaaacaaa atcatactta    1894
ttagaagaaa attctgattt tatagaaaaa aaatagagca aggagaatat aacatgtttg    1954
caaagtcatg tgttttcttt ctcaatgagg gaaaaacaat tttattacct gcttaatggt    2014
ccacctggaa ctaaaaggga tactattttc taacaaggta tatctagtag gggagaaagc    2074
caccacaata aatatatttg ttaatag                                        2101
```

<210> SEQ ID NO 34
<211> LENGTH: 272
<212> TYPE: PRT
<213> ORGANISM: Homo sapiens

<400> SEQUENCE: 34

```
Met His Leu Arg Leu Ile Ser Trp Leu Phe Ile Ile Leu Asn Phe Met
 1               5                  10                  15

Glu Tyr Ile Gly Ser Gln Asn Ala Ser Arg Gly Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
    130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Cys Gln Lys
        195                 200                 205

Gly Glu Arg Gly Lys Lys Gly Arg Glu Arg Lys Arg Lys Pro Asn
    210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255

Arg Lys Val Gln Asp Lys Gln Lys Ser Val Ser Val Ser Thr Val His
            260                 265                 270
```

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 35
agtacaaaga aagaagtgtt c                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 36
tgagtctaca gtaacctcgc a                                              21

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 37
taatacgact cactataggg                                                20

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 38
tcgcggcgat gccagccacc ccag                                           24

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 39
agcacgccta tcggatgtga gaggagaagt                                     30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 40
ctattaacaa atatatttat tgtggtggct                                     30

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: PCR primer

```
<400> SEQUENCE: 41
tggtggcttt ctcccctact agatatacct                                30

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 42
gattttaggt gacactatag                                           20

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: PCR primer

<400> SEQUENCE: 43
ccgctcgagc caccatgcac ttgcgactga tttc                           34

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 44
attgaattcc tagtgtacag tgctgactg                                 29

<210> SEQ ID NO 45
<211> LENGTH: 84
<212> TYPE: DNA
<213> ORGANISM: Homo sapiens
<220> FEATURE:
<223> OTHER INFORMATION: Description of Artificial Sequence: PCR primer
<220> FEATURE:
<221> NAME/KEY: CDS
<222> LOCATION: (1)..(81)

<400> SEQUENCE: 45 ggg att gaa gtc acc cta gct gaa ggc ctc acc agt gtt tca cag agg      48
Gly Ile Glu Val Thr Leu Ala Glu Gly Leu Thr Ser Val Ser Gln Arg
 1               5                  10                  15 aca cag ccc acc cct tgc agg agg agg tat ctc tga                      84
Thr Gln Pro Thr Pro Cys Arg Arg Arg Tyr Leu
             20                  25

<210> SEQ ID NO 46
<211> LENGTH: 27
<212> TYPE: PRT
<213> ORGANISM: Homo sapiens

<400> SEQUENCE: 46

Gly Ile Glu Val Thr Leu Ala Glu Gly Leu Thr Ser Val Ser Gln Arg
 1               5                  10                  15

Thr Gln Pro Thr Pro Cys Arg Arg Arg Tyr Leu
             20                  25

<210> SEQ ID NO 47
<211> LENGTH: 1436
<212> TYPE: DNA
```

-continued

<213> ORGANISM: Homo sapiens

<400> SEQUENCE: 47

```
cccggcggct cctggaaccc cggttcgcgg cgatgccagc caccccagcg aagccgccgc      60
agttcagtgc ttggataatt tgaaagtaca atagttggtt tccctgtcca cccgccccac     120
ttcgcttgcc atcacagcac gcctatcgga tgtgagagga gaagtcccgc tgctcgggca     180
ctgtctatat acgcctaaca cctacatata ttttaaaaac attaaatata attaacaatc     240
aaaagaaaga ggagaaagga agggaagcat tactgggtta ctatgcactt gcgactgatt     300
tcttggcttt ttatcatttt gaactttatg aatacatcg gcagccaaaa cgcctcccgg      360
ggaaggcgcc agcgaagaat gcatcctaac gttagtcaag gctgccaagg aggctgtgca     420
acatgctcag attacaatgg atgtttgtca tgtaagccca gactattttt tgctctggaa     480
agaattggca tgaagcagat tggagtatgt ctctcttcat gtccaagtgg atattatgga     540
actcgatatc cagatataaa taagtgtaca aaatgcaaag ctgactgtga tacctgtttc     600
aacaaaaatt tctgcacaaa atgtaaaagt ggattttact tacaccttgg aaagtgcctt     660
gacaattgcc cagaagggtt ggaagccaac aaccatacta tggagtgtgt cagtattgtg     720
cactgtgagg tcagtgaatg gaatccttgg agtccatgca cgaagaaggg aaaaacatgt     780
ggcttcaaaa gagggactga aacacgggtc cgagaaataa tacagcatcc ttcagcaaag     840
ggtaacctgt gtcccccaac aaatgagaca agaaagtgta cagtgcaaag gaagaagtgt     900
cagaagggag aacgaggaaa aaaggaaggg agaggaaaa gaaaaaaacc taataaagga     960
gaaagtaaag aagcaatacc tgacagcaaa agtctggaat ccagcaaaga aatcccagag    1020
caacgagaaa acaaacagca gcagaagaag cgaaaagtcc aagataaaca gaaatcgggg    1080
attgaagtca ccctagctga aggcctcacc agtgtttcac agaggacaca gcccacccct    1140
tgcaggagga ggtatctctg agtgtgcagc acagaatcgc atgacccacc ttaaccttcc    1200
tgttgtcatg gaaggatgca cggctgctct gtccactgtg attcctagcc ctctcaagat    1260
cactgctttc tgaagaattt gcaatgactc tggcttctgg ctgcttatct ctggacaccc    1320
gttctccacc agttgtacag ttcatgtaat ctacttggct taattgattt tccacttctc    1380
tcttcctctt ctaagatata aacattttaa atgatttaaa aaaaaaaaaa aaaaaa        1436
```

<210> SEQ ID NO 48
<211> LENGTH: 292
<212> TYPE: PRT
<213> ORGANISM: Homo sapiens

<400> SEQUENCE: 48

```
Met His Leu Arg Leu Ile Ser Trp Leu Phe Ile Ile Leu Asn Phe Met
  1               5                  10                  15

Glu Tyr Ile Gly Ser Gln Asn Ala Ser Arg Gly Arg Gln Arg Arg
             20                  25                  30

Met His Pro Asn Val Ser Gln Gly Cys Gln Gly Gly Cys Ala Thr Cys
         35                  40                  45

Ser Asp Tyr Asn Gly Cys Leu Ser Cys Lys Pro Arg Leu Phe Phe Ala
     50                  55                  60

Leu Glu Arg Ile Gly Met Lys Gln Ile Gly Val Cys Leu Ser Ser Cys
 65                  70                  75                  80

Pro Ser Gly Tyr Tyr Gly Thr Arg Tyr Pro Asp Ile Asn Lys Cys Thr
                 85                  90                  95

Lys Cys Lys Ala Asp Cys Asp Thr Cys Phe Asn Lys Asn Phe Cys Thr
```

-continued

```
                    100                 105                 110
Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
        130                 135                 140

Ile Val His Cys Glu Val Ser Glu Trp Asn Pro Trp Ser Pro Cys Thr
145                     150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
        195                 200                 205

Gly Glu Arg Gly Lys Lys Gly Arg Glu Arg Lys Arg Lys Lys Pro Asn
    210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255

Arg Lys Val Gln Asp Lys Gln Lys Ser Gly Ile Glu Val Thr Leu Ala
            260                 265                 270

Glu Gly Leu Thr Ser Val Ser Gln Arg Thr Gln Pro Thr Pro Cys Arg
        275                 280                 285

Arg Arg Tyr Leu
    290
```